United States Patent
Bland et al.

(10) Patent No.: US 9,788,744 B2
(45) Date of Patent: Oct. 17, 2017

(54) SYSTEMS FOR MONITORING BRAIN ACTIVITY AND PATIENT ADVISORY DEVICE

(75) Inventors: Michael Bland, Seattle, WA (US); Kent W. Leyde, Sammamish, WA (US); Neil G. McIlvaine, Seattle, WA (US); Shan Gaw, Seattle, WA (US); Peter Weiss, Mercer Island, WA (US); John F. Harris, Bellevue, WA (US)

(73) Assignee: CYBERONICS, INC., Houston, TX (US)

( * ) Notice: Subject to any disclaimer, the term of this patent is extended or adjusted under 35 U.S.C. 154(b) by 1760 days.

(21) Appl. No.: 12/180,996

(22) Filed: Jul. 28, 2008

(65) Prior Publication Data

US 2009/0062682 A1 Mar. 5, 2009

Related U.S. Application Data

(60) Provisional application No. 60/952,463, filed on Jul. 27, 2007.

(51) Int. Cl.
| | |
|---|---|
| A61B 5/04 | (2006.01) |
| A61B 5/0478 | (2006.01) |
| A61B 5/042 | (2006.01) |
| A61B 5/0432 | (2006.01) |
| A61B 5/044 | (2006.01) |
| A61B 5/0448 | (2006.01) |
| A61B 5/0476 | (2006.01) |
| A61B 5/0496 | (2006.01) |
| A61B 5/00 | (2006.01) |

(52) U.S. Cl.
CPC .......... *A61B 5/0476* (2013.01); *A61B 5/0031* (2013.01); *A61B 5/4094* (2013.01)

(58) Field of Classification Search
CPC ......... A61B 5/026; A61B 5/412; A61B 5/418; A61B 5/08; A61B 5/0402; A61B 5/02055; A61B 5/0452; A61B 5/053; A61B 5/00; A61B 5/1116; A61B 5/6887; A61B 2562/0209; A61B 5/0031; A61B 5/4094; A61B 5/0816; A61B 5/02; A61B 5/0205; A61B 5/0245; A61B 5/11; A61B 5/1135; A61B 5/01; A61B 5/0492; A61B 5/1123; A61B 5/1124; A61B 5/4005; A61B 5/4023; A61B 5/486; A61B 5/7225; A61B 5/726; A61B 5/0478; A61B 5/4519; A61B 5/7275; A61N 1/36585; A61N 1/37288; A61N 1/36521; A61N 1/3601; A61N 1/36014; A61N 1/36025; A61N 1/37247; A61N 1/37282; A61N 1/36103; A61N 1/05; A61N 1/37258; A61N 1/36082; A61N 1/3962; A61N 1/36135; A61N 1/362; A61N 1/365; A61N 1/37; A61N 1/36064; G06F 19/345; G06F 19/3418; G06F 19/3406; G06F 3/015; G06F 19/3481; G06F 19/328; G06F 19/3443; G06Q 50/22; A61M 5/1723; A61M 2205/3592

See application file for complete search history.

(56) References Cited

U.S. PATENT DOCUMENTS

| | | |
|---|---|---|
| 3,218,638 A | 11/1965 | Honig |
| 3,498,287 A | 3/1970 | Ertl |
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |

(Continued)

FOREIGN PATENT DOCUMENTS

| | | |
|---|---|---|
| CA | 2251852 | 4/1999 |
| CA | 2423840 | 2/2002 |
| CA | 2428116 | 5/2002 |
| CA | 2428383 | 5/2002 |
| CA | 2425122 | 6/2002 |

(Continued)

OTHER PUBLICATIONS

Leyde et al.; U.S. Appl. No. 12/343,376 entitled "Systems and method for recording clinical manifestations of a seizure," filed Dec. 23, 2008.

Brown et al.; U.S. Appl. No. 12/343,386 entitled "Housing for an implantable medical device," filed Dec. 23, 2008.

(Continued)

*Primary Examiner* — Chang-Yu Wang
(74) *Attorney, Agent, or Firm* — Foley & Lardner LLP

(57) ABSTRACT

A patient advisory device ("PAD") and its methods of use. The PAD may be configured to alert the patient about an estimated brain state of the patient. In preferred embodiments, the PAD is adapted to alert the patient of the patient's brain state, which corresponds to the patient's propensity of transitioning into an ictal brain state, e.g., having a seizure. Based on the specific type of alert, the patient will be made aware whether they are highly unlikely to have a seizure for a given period of time, an elevated propensity of having a seizure, a seizure is occurring or imminent, or the patient's brain state is unknown.

19 Claims, 38 Drawing Sheets

(56) References Cited

U.S. PATENT DOCUMENTS

| | | |
|---|---|---|
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkam |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,867,164 A | 9/1989 | Zabara |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,934,372 A | 6/1990 | Corenman et al. |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 5,010,891 A | 4/1991 | Chamoun |
| 5,016,635 A | 5/1991 | Graupe |
| 5,025,807 A | 6/1991 | Zabara |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varrichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deCoriolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,517,115 A | 5/1996 | Prammer |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |
| 5,700,282 A | 12/1997 | Zabara |
| 5,704,352 A | 1/1998 | Tremblay et al. |
| 5,707,400 A | 1/1998 | Terry |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,782,891 A | 7/1998 | Hassler et al. |
| 5,792,186 A | 8/1998 | Rise |
| 5,800,474 A | 9/1998 | Bernabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A | 1/1999 | Besson et al. |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |
| 5,931,791 A | 8/1999 | Saltzstein et al. |
| 5,938,689 A | 8/1999 | Fischell et al. |
| 5,941,906 A | 8/1999 | Barreras et al. |
| 5,950,632 A | 9/1999 | Reber et al. |
| 5,957,861 A | 9/1999 | Combs et al. |

(56) References Cited

U.S. PATENT DOCUMENTS

| | | |
|---|---|---|
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,163 A | 5/2000 | John |
| 6,081,744 A | 6/2000 | Loos |
| 6,094,598 A | 7/2000 | Elsberry et al. |
| 6,108,571 A * | 8/2000 | Minoz et al. ............... 600/361 |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,208,893 B1 | 3/2001 | Hofmann |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,854 B1 | 6/2002 | Tziviskos et al. |
| 6,427,086 B1 | 7/2002 | Fischell et al. |
| 6,434,419 B1 | 8/2002 | Gevins et al. |
| 6,442,421 B1 | 8/2002 | Quyen et al. |
| 6,443,891 B1 | 9/2002 | Grevious |
| 6,453,198 B1 | 9/2002 | Torgerson |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,505,077 B1 | 1/2003 | Kast et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 | 4/2003 | Osorio et al. |
| 6,553,262 B1 | 4/2003 | Lang et al. |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,594,524 B2 * | 7/2003 | Esteller et al. ............... 607/45 |
| 6,597,954 B1 | 7/2003 | Pless et al. |
| 6,600,956 B2 | 7/2003 | Maschino et al. |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,658,287 B1 | 12/2003 | Litt et al. |
| 6,665,562 B2 | 12/2003 | Gluckman et al. |
| 6,668,191 B1 | 12/2003 | Boveja |
| 6,671,555 B2 | 12/2003 | Gielen |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,879,859 B1 | 4/2005 | Boveja |
| 6,893,395 B1 | 5/2005 | Kraus et al. |
| 6,901,294 B1 | 5/2005 | Whitehurst et al. |
| 6,901,296 B1 | 5/2005 | Whitehurst |
| 6,912,419 B2 | 6/2005 | Hill et al. |
| 6,921,538 B2 | 7/2005 | Donovan |
| 6,921,541 B2 | 7/2005 | Chasin et al. |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |
| 6,944,501 B1 | 9/2005 | Pless |
| 6,950,706 B2 | 9/2005 | Rodriquez |
| 6,973,342 B1 | 12/2005 | Swanson |
| 6,990,372 B2 | 1/2006 | Perron et al. |
| 7,010,351 B2 | 3/2006 | Firlik et al. |
| 7,089,059 B1 | 8/2006 | Pless |
| 7,117,108 B2 | 10/2006 | Rapp et al. |
| 7,136,695 B2 * | 11/2006 | Pless et al. ............... 600/544 |
| 7,174,212 B1 | 2/2007 | Klehn et al. |
| 7,177,674 B2 * | 2/2007 | Echauz et al. ............... 600/544 |
| 7,177,701 B1 | 2/2007 | Pianca |
| 7,212,851 B2 | 5/2007 | Donoghue et al. |
| 7,231,254 B2 | 6/2007 | DiLorenzo |
| 7,324,851 B1 | 1/2008 | DiLorenzo |
| 7,373,198 B2 | 5/2008 | Bibian et al. |
| 7,463,917 B2 | 12/2008 | Martinez |
| 7,631,015 B2 | 12/2009 | Gupta et al. |
| 7,676,263 B2 * | 3/2010 | Harris et al. ............... 600/544 |
| 7,787,945 B2 * | 8/2010 | Greene ............... 600/544 |
| 7,805,196 B2 * | 9/2010 | Miesel et al. ............... 607/45 |
| 7,881,798 B2 * | 2/2011 | Miesel et al. ............... 607/48 |
| 8,036,736 B2 * | 10/2011 | Snyder et al. ............... 600/544 |
| 8,055,348 B2 * | 11/2011 | Heruth et al. ............... 607/45 |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1 * | 8/2002 | Echauz et al. ............... 607/9 |
| 2002/0109621 A1 | 8/2002 | Khair et al. |

(56) References Cited

U.S. PATENT DOCUMENTS

| | | |
|---|---|---|
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Pless et al. |
| 2002/0177882 A1 | 11/2002 | DiLorenzo |
| 2002/0188330 A1 | 12/2002 | Gielen et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1* | 4/2003 | Echauz et al. ............... 600/510 |
| 2003/0074033 A1* | 4/2003 | Pless et al. ..................... 607/48 |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010113 A1 | 1/2005 | Hall et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021108 A1 | 1/2005 | Klosterman et al. |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0119703 A1 | 6/2005 | DiLorenzo |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad et al. |
| 2005/0197590 A1 | 9/2005 | Osorio et al. |
| 2005/0203366 A1 | 9/2005 | Donoghue et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |
| 2006/0224191 A1 | 10/2006 | Dilorenzo |
| 2006/0253096 A1 | 11/2006 | Blakley et al. |
| 2006/0293578 A1 | 12/2006 | Rennaker, II |
| 2006/0293720 A1 | 12/2006 | DiLorenzo et al. |
| 2007/0027367 A1 | 2/2007 | Oliver et al. |
| 2007/0027514 A1 | 2/2007 | Gerber |
| 2007/0035910 A1 | 2/2007 | Stevenson |
| 2007/0043459 A1 | 2/2007 | Abbott, III et al. |
| 2007/0055320 A1 | 3/2007 | Weinand |
| 2007/0060973 A1 | 3/2007 | Ludvig et al. |
| 2007/0073355 A1 | 3/2007 | DiLorenzo |
| 2007/0073357 A1 | 3/2007 | Rooney et al. |
| 2007/0100398 A1 | 5/2007 | Sloan |
| 2007/0142862 A1 | 6/2007 | DiLorenzo |
| 2007/0149952 A1 | 6/2007 | Bland et al. |
| 2007/0150024 A1* | 6/2007 | Leyde et al. ..................... 607/45 |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0185890 A1 | 8/2007 | VanEpps et al. |
| 2007/0197878 A1 | 8/2007 | Shklarski |
| 2007/0213629 A1* | 9/2007 | Greene ......................... 600/544 |

(56) References Cited

U.S. PATENT DOCUMENTS

| | | | |
|---|---|---|---|
| 2007/0213785 A1 | 9/2007 | Osorio et al. | |
| 2007/0217121 A1 | 9/2007 | Fu et al. | |
| 2007/0238939 A1 | 10/2007 | Giftakis et al. | |
| 2007/0244407 A1 | 10/2007 | Osorio | |
| 2007/0250077 A1 | 10/2007 | Skakoon et al. | |
| 2007/0287931 A1 | 12/2007 | DiLorenzo | |
| 2008/0021341 A1 | 1/2008 | Harris et al. | |
| 2008/0027347 A1 | 1/2008 | Harris et al. | |
| 2008/0027348 A1 | 1/2008 | Harris et al. | |
| 2008/0027515 A1* | 1/2008 | Harris et al. | 607/62 |
| 2008/0033502 A1 | 2/2008 | Harris et al. | |
| 2008/0082019 A1 | 4/2008 | Ludving et al. | |
| 2008/0091090 A1 | 4/2008 | Guillory et al. | |
| 2008/0103556 A1 | 5/2008 | Li et al. | |
| 2008/0114417 A1* | 5/2008 | Leyde | 607/60 |
| 2008/0119900 A1 | 5/2008 | DiLorenzo | |
| 2008/0161712 A1 | 7/2008 | Leyde | |
| 2008/0161713 A1 | 7/2008 | Leyde et al. | |
| 2008/0183096 A1* | 7/2008 | Snyder et al. | 600/545 |
| 2008/0183097 A1* | 7/2008 | Leyde et al. | 600/545 |
| 2008/0208074 A1* | 8/2008 | Snyder et al. | 600/545 |
| 2008/0221876 A1 | 9/2008 | Holdrich | |
| 2008/0255582 A1* | 10/2008 | Harris | 606/129 |
| 2008/0273287 A1 | 11/2008 | Iyer et al. | |
| 2008/0319281 A1 | 12/2008 | Aarts | |
| 2009/0062696 A1 | 3/2009 | Nathan et al. | |
| 2009/0171168 A1* | 7/2009 | Leyde et al. | 600/301 |
| 2009/0264952 A1 | 10/2009 | Jassemidis et al. | |
| 2010/0023089 A1 | 1/2010 | DiLorenzo | |
| 2010/0292602 A1 | 11/2010 | Worrell et al. | |
| 2011/0166430 A1* | 7/2011 | Harris et al. | 600/301 |
| 2011/0172554 A1* | 7/2011 | Leyde et al. | 600/544 |
| 2011/0201944 A1* | 8/2011 | Higgins et al. | 600/483 |
| 2011/0213222 A1* | 9/2011 | Leyde et al. | 600/301 |
| 2011/0260855 A1 | 10/2011 | John et al. | |
| 2011/0319785 A1* | 12/2011 | Snyder et al. | 600/544 |
| 2012/0203131 A1 | 8/2012 | DiLorenzo et al. | |
| 2012/0257339 A1 | 10/2012 | Leyde et al. | |

FOREIGN PATENT DOCUMENTS

| | | |
|---|---|---|
| CA | 2425004 | 8/2002 |
| CA | 2456443 | 1/2003 |
| CA | 2491987 | 1/2004 |
| DE | 69832022 | 12/2005 |
| EP | 0124663 A1 | 11/1984 |
| EP | 0898460 | 3/1999 |
| EP | 1017313 | 7/2000 |
| EP | 1107693 | 6/2001 |
| EP | 1145735 A2 | 10/2001 |
| EP | 1145736 A2 | 10/2001 |
| EP | 1292900 | 3/2003 |
| EP | 1307260 | 5/2003 |
| EP | 1331967 | 8/2003 |
| EP | 1335668 | 8/2003 |
| EP | 1341580 | 9/2003 |
| EP | 1404216 | 4/2004 |
| EP | 1333753 | 9/2004 |
| EP | 1525551 | 4/2005 |
| EP | 1558121 | 8/2005 |
| EP | 1558128 | 8/2005 |
| EP | 1558130 | 8/2005 |
| EP | 1558131 | 8/2005 |
| EP | 1558132 | 8/2005 |
| EP | 1558330 | 8/2005 |
| EP | 1558334 | 8/2005 |
| EP | 1562674 | 8/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/009610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A1 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 2004/008373 A2 | 1/2004 |
| WO | WO 2004/032720 A2 | 4/2004 |
| WO | WO 2004/034231 A2 | 4/2004 |
| WO | WO 2004/034879 A2 | 4/2004 |
| WO | WO 2004/034880 A2 | 4/2004 |
| WO | WO 2004/034881 A2 | 4/2004 |
| WO | WO 2004/034882 A2 | 4/2004 |
| WO | WO 2004/034883 A2 | 4/2004 |
| WO | WO 2004/034885 A2 | 4/2004 |
| WO | WO 2004/034982 A2 | 4/2004 |
| WO | WO 2004/034997 A2 | 4/2004 |
| WO | WO 2004/034998 A2 | 4/2004 |
| WO | WO 2004/035130 A2 | 4/2004 |
| WO | WO 2004/036370 A2 | 4/2004 |
| WO | WO 2004/036372 A2 | 4/2004 |
| WO | WO 2004/036376 A2 | 4/2004 |
| WO | WO 2004/036377 A2 | 4/2004 |
| WO | WO 2004/037342 A2 | 5/2004 |
| WO | WO 2004/043536 A1 | 5/2004 |
| WO | WO 2004/091718 A1 | 10/2004 |
| WO | WO 2005/007236 A2 | 1/2005 |
| WO | WO 2005/028026 A1 | 3/2005 |
| WO | WO 2005/028028 A1 | 3/2005 |
| WO | WO 2005/031630 A2 | 4/2005 |
| WO | WO 2005/051167 A1 | 6/2005 |
| WO | WO 2005/051306 A2 | 6/2005 |
| WO | WO 2005/117693 A1 | 12/2005 |
| WO | WO 2006/014971 A2 | 2/2006 |
| WO | WO 2006/014972 A2 | 2/2006 |
| WO | WO 2006/020794 A2 | 2/2006 |
| WO | WO2006035392 | 4/2006 |
| WO | WO 2007/150003 A2 | 12/2007 |

OTHER PUBLICATIONS

Himes, David M.; U.S. Appl. No. 12/630,300 entitled "Universal Electrode Array for Monitoring Brain Activity," filed Dec. 3, 2009.

Himes et al.; U.S. Appl. No. 12/646,783 entitled "Brain State Analysis Based on Select Seizure Onset Characteristics and Clinical Manifestations," filed Dec. 23, 2009.

Echauz et al.; U.S. Appl. No. 12/649,098 entitled "Processing for Multi-Channel Signals," filed Dec. 29, 2009.

Floyd et al.; U.S. Appl. No. 12/685,543 entitled "Medical Lead Termination Sleeve for Implantable Medical Devices," filed Jan. 11, 2010.

Harris et al.; U.S. Appl. No. 12/691,650 entitled "Minimally invasive system for selecting patient-specific therapy parameters," filed Jan. 21, 2010.

(56) References Cited

OTHER PUBLICATIONS

Rimes et al.; U.S. Appl. No. 12/716,132 entitled "Displaying and Manipulating Brain Function Data Including Enhanced Data Scrolling Functionality," filed Mar. 2, 2010.
Himes et al.; U.S. Appl. No. 12/716,147 entitled "Displaying and Manipulating Brain Function Data Including Filtering of Annotations," filed Mar. 2, 2010.
Rothman et al.; Local Cooling: a therapy for intractable neocortical epilepsy; Epilepsy Currents; vol. 3; No. 5; pp. 153-156; Sep./Oct. 2003.
Higgins et al.; U.S. Appl. No. 13/026,961 entitled "Neurological monitoring and alerts," filed Feb. 14, 2011.
Harris et al.; U.S. Appl. No. 13/050,839 entitled "System and methods for analyzing seizure activity," filed Mar. 17, 2011.
Leyde et al.; U.S. Appl. No. 13/070,333 entitled "Communication Error Alerting in an Epilepsy Monitoring System," filed Mar. 23, 2011.
Leyde et al.; U.S. Appl. No. 13/070,357 entitled "Patient Entry Recording in an Epilepsy Monitoring System," filed Mar. 23, 2011.
DiLorenzo, Daniel; U.S. Appl. No. 12/774,550 entitled "Systems for Monitoring a Patient's Neurological Disease State," filed May 5, 2010.
Echauz et al.; U.S. Appl. No. 12/792,582 entitled "Processing for Multi-Channel Signals," filed Jun. 2, 2010.
Adjouadi, et al. A new mathematical approach based on orthogonal operators for the detection of interictal spikes in epileptogenic data. Biomed. Sci. Instrum. 2004; 40: 175-80.
Adjouadi, et al. Detection of interictal spikes and artifactual data through orthogonal transformations. J. Clin. Neurophysiol. 2005; 22(1):53-64.
Adjouadi, et al. Interictal spike detection using the Walsh transform. IEEE Trans. Biomed. Eng. 2004; 51(5): 868-72.
Aksenova, et al. Nonparametric on-line detection of changes in signal spectral characteristics for early prediction of epilepsy seizure onset. J. Automation and Information Sciences. 2004; 36(8): 35-45.
Aksenova, et al. On-line disharmony detection for early prediction of epilepsy seizure onset. 5th International Workshop Neural Coding 2003. Aulla (Italy) Sep. 20-25, 2003. (Abstract).
Andrzejak, et al. Bivariate surrogate techniques: necessity, strengths, and caveats. Physical Review E. 2003; 68: 066202-1-066202-15.
Andrzejak, et al. Testing the null hypothesis of the nonexistence of a preseizure state. Physical Review E. 2003; 67: 010901-1-010901-4.
Aschenbrenner-Scheibe, et al. How well can epileptic seizures be predicted? An evaluation of a nonlinear method. Brain. 2003; 126: 2616-26.
Bangham et al. Diffusion of univalent ions across the lamellae of swollen phospholipids. 1965. J Mol. Biol. 13: 238-252.
Baruchi, et al. Functional holography of complex networks activity—From cultures to the human brain. Complexity. 2005; 10(3): 38 R 51.
Baruchi, et al. Functional holography of recorded neuronal networks activity. Neuroinformatics. 2004; 2(3): 333-51.
Ben-Hur, et al. Detecting stable clusters using principal component analysis. Methods Mol. Biol. 2003; 224: 159-82.
Bergey, et al. Epileptic seizures are characterized by changing signal complexity. Clin. Neurophysiol. 2001; 112(2): 241-9.
Betterton, et al. Determining State of Consciousness from the Intracranial Electroencephalogram (IEEG) for Seizure Prediction. From Proceeding (377) Modeling, Identification, and Control. 2003; 377-201: 313-317.
Bhattacharya, et al. Enhanced phase synchrony in the electroencephalograph gamma band for musicians while listening to music. Phys. Rev. E. 2001; 64:012902-1-4.
Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.
Cao, et al. Detecting dynamical changes in time series using the permutation entropy. Physical Review E. 2004; 70:046217-1-046217-7.
Carretero-Gonzalez, et al. Scaling and interleaving of subsystem Lyapunov exponents for spatio-temporal systems. Chaos. 1999; 9(2): 466-482.
Casdagli, et al. Characterizing nonlinearity in invasive EEG recordings from temporal lobe epilepsy. Physica D. 1996; 99 (2/3): 381-399.
Casdagli, et al. Nonlinear Analysis of Mesial Temporal Lobe Seizures Using a Surrogate Data Technique. Epilepsia. 1995; 36, suppl. 4, pp. 142.
Casdagli, et al. Non-linearity in invasive EEG recordings from patients with temporal lobe epilepsy. Electroencephalogr. Clin. Neurophysiol. 1997; 102(2): 98-105.
Cerf, et al. Criticality and synchrony of fluctuations in rhythmical brain activity: pretransitional effects in epileptic patients. Biol. Cybern. 2004; 90(4): 239-55.
Chaovalitwongse, et al. EEG Classification in Epilepsy. Annals. 2004; 2(37): 1-31.
Chaovalitwongse, et al. Performance of a seizure warning algorithm based on the dynamics of intracranial EEG. Epilepsy Res. 2005; 64(3): 93-113.
Chavez, et al. Spatio-temporal dynamics prior to neocortical seizures: amplitude versphase couplings. IEEE Trans. Biomed. Eng. 2003; 50(5):571-83.
Crichton, Michael, "Terminal Man", 1972, Ballantine Books, NY, NY, pp. 21-24, 32-33, 70-71, and 74-81.
D'Alessandro, et al. Epileptic seizure prediction using hybrid feature selection over multiple intracranial EEG electrode contacts: a report of four patients. IEEE Trans. Biomed. Eng. 2003; 50(5): 603-15.
D'Alessandro, et al. A multi-feature and multi-channel univariate selection process for seizure prediction. Clin. Neurophysiol. 2005; 116(3): 506-16.
Drury, et al. Seizure prediction using scalp electroencephalogram. Exp. Neurol. 2003; 184 Suppl 1: S9-18.
Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.
Ebersole, J. S. In search of seizure prediction: a critique. Clin. Neurophysiol. 2005; 116(3): 489-92.
Elbert et al. Chaos and Physiology: Deterministic Chaos in Excitable Cell Assemblies. Physiological Reviews. 1994; 74(1):1-47.
Elger, et al. Nonlinear EEG analysis and its potential role in epileptology. Epilepsia. 2000; 41 Suppl 3: S34-8.
Elger, et al. Seizure prediction by non-linear time series analysis of brain electrical activity. Eur. J. Neurosci. 1998; 10(2): 786-789.
Esteller, et al. A Comparison of Waveform Fractal Dimension Algorithms. IEEE Transactions on Circuits and Systems. 2001; vol. 48(2): 177-183.
Esteller, et al. Continuoenergy variation during the seizure cycle: towards an on-line accumulated energy. Clin. Neurophysiol. 2005; 116(3): 517-26.
Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.
Faul, et al. An evaluation of automated neonatal seizure detection methods. Clin. Neurophysiol. 2005; 116(7): 1533-41.
Fein, et al. Common reference coherence data are confounded by power and phase effects. Electroencephalogr. Clin. Neurophysiol. 1988; 69:581-584.
Fell, et al. Linear inverse filtering improves spatial separation of nonlinear brain dynamics: a simulation study. J. Neurosci. Methods. 2000; 98(1): 49-56.

(56) References Cited

OTHER PUBLICATIONS

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.
Fisher et al. 1999. Reassessment: Vagnerve stimulation for epilepsy, A report of the therapeutics and technology assessment subcommittee of the American Academy of Neurology. Neurology.53: 666-669.
Gardner, A. B. A Novelty Detection Approach to Seizure Analysis from Intracranial EEG. Georgia Institute of Technology. Apr. 2004. A dissertation available at http://etd.gatech.edu/theses / available/ etd-04122004-132404/unrestricted/gardner_andrew_b_200405_ phd.pdf. Accessed Feb. 28, 2006.
Geva, et al. Forecasting generalized epileptic seizures from the EEG signal by wavelet analysis and dynamic unsupervised fuzzy clustering. IEEE Trans. Biomed. Eng. 1998; 45(10): 1205-16.
Gigola, et al. Prediction of epileptic seizures using accumulated energy in a multiresolution framework. J. Neurosci. Methods. 2004; 138(1-2): 107-111.
Guyon, I. An introduction to variable and feature selection. Journal of Machine Learning Research. 2003; 3:1157-1182.
Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.
Harrison, et al. Accumulated energy revised. Clin. Neurophysiol. 2005; 116(3):527-31.
Harrison, et al. Correlation dimension and integral do not predict epileptic seizures. Chaos. 2005; 15(3): 33106-1-15.
Hearst M. Trends & Controversies: Support Vector Machines. IEEE Intelligent Systems. 1998; 13: 18-28.
Hively, et al. Channel-consistent forewarning of epileptic events from scalp EEG. IEEE Trans. Biomed. Eng. 2003; 50(5): 584-93.
Hively, et al. Detecting dynamical changes in nonlinear time series. Physics Letters A. 1999; 258: 103-114.
Hively, et al. Epileptic Seizure Forewarning by Nonlinear Techniques. ORNL/TM-2000/333 Oak Ridge National Laboratory. Nov. 2000. Available at http://computing.oml.gov/cse_home/staff/ hively/NBICradaAnnualRpt FY00.pdf. Accessed Feb. 28, 2006.
Hjorth, B. Source derivation simplifies topographical EEG interpretation. Am. J. EEG Technol. 1980; 20: 121-132.
Hsu, et al. A practical guide to support vector classification. Technical report, Department of Computer Science and Information Technology, National Taiwan University, 2003. Available at http:// www.csie.ntu.edu.tw/~cjlin/papers/guide/guide.pdf. Accessed Feb. 28, 2006.
Huynh, J. A. Evaluation of Gene Selection Using Support Vector Machine Recursive Feature Elimination. Arizona State University. May 26, 2004. (28 pages).
Huynh, J. A. Evaluation of Gene Selection Using Support Vector Machine Recursive Feature Elimination. Presentation slides. (41 pages) (May 26, 2004).
Iasemidis, et al. Adaptive epileptic seizure prediction system. IEEE Trans. Biomed. Eng. 2003; 50(5):616-27.
Iasemidis, et al. Automated Seizure Prediction Paradigm. Epilepsia. 1998; vol. 39, pp. 56.
Iasemidis, et al. Chaos Theory and Epilepsy. The Neuroscientist. 1996; 2:118-126.
Iasemidis, et al. Comment on "Inability of Lyapunov exponents to predict epileptic seizures." Physical Review Letters. 2005; 94(1):019801-1.
Iasemidis, et al. Detection of the Preictal Transition State in Scalp-Sphenoidal EEG Recordings. American Clinical Neurophysiology Society Annual Meeting, Sep. 1996. pp. C206.
Iasemidis, et al. Dynamical Interaction of the Epileptogenic Focwith Extrafocal Sites in Temporal Lobe Epilepsy (TLE). Ann. Neurol. 1997; 42, pp. 429. pp. M146.
Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.
Iasemidis, et al. Localizing Preictal Temporal Lobe Spike Foci Using Phase Space Analysis. Electroencephalography and Clinical Neurophysiology. 1990; 75, pp. S63-S64.
Iasemidis, et al. Long-term prospective on-line real-time seizure prediction. Clin. Neurophysiol. 2005; 116 (3):532-44.
Iasemidis, et al. Long-Time-Scale Temporo-spatial Patterns of Entrainment of Preictal Electrocorticographic Data in Human Temporal Lobe Epilepsy. Epilepsia. 1990; 31(5):621.
Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.
Iasemidis, et al. Modelling of ECoG in temporal lobe epilepsy. Biomed. Sci. Instrum. 1988; 24: 187-93.
Iasemidis, et al. Nonlinear Dynamics of EcoG Data in Temporal Lobe Epilepsy. Electroencephalography and Clinical Neurophysiology. 1998; 5, pp. 339.
Iasemidis, et al. Phase space topography and the Lyapunov exponent of electrocorticograms in partial seizures. Brain Topogr. 1990; 2(3): 187-201.
Iasemidis, et al. Preictal Entrainment of a Critical Cortical Mass is a Necessary Condition for Seizure Occurrence. Epilepsia. 1996; 37, suppl. 5. pp. 90.
Iasemidis, et al. Preictal-Postictal Versus Postictal Analysis for Epileptogenic Focus Localization. J. Clin. Neurophysiol. 1997; 14, pp. 144.
Iasemidis, et al. Quadratic binary programming and dynamic system approach to determine the predictability of epileptic seizures. Journal of Combinatorial Optimization. 2001; 5: 9-26.
Iasemidis, et al. Quantification of Hidden Time Dependencies in the EEG within the Framework of Non-Linear Dynamics. World Scientific. 1993; pp. 30-47.
Iasemidis, et al. Spatiotemporal dynamics of human epileptic seizures. World Scientific. 1996; pp. 26-30.
Iasemidis, et al. Spatiotemporal Evolution of Dynamical Measures Precedes Onset of Mesial Temporal Lobe Seizures. Epilepsia. 1994; 358, pp. 133.
Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artificial Systems. Ohmsha IOS Press. 1997; 37, pp. 81-88.).
Iasemidis, et al. The evolution with time of the spatial distribution of the largest Lyapunov exponent on the human epileptic cortex. World Scientific. 1991; pp. 49-82.
Iasemidis, et al. The Use of Dynamical Analysis of EEG Frequency Content in Seizure Prediction. American Electroencephalographic Society Annual Meeting, Oct. 1993.
Iasemidis, et al. Time Dependencies in Partial Epilepsy. 1993; 34, pp. 130-131.
Iasemidis, et al. Time dependencies in the occurrences of epileptic seizures. Epilepsy Res. 1994; 17(1): 81-94.
Iasemidis, L. D. Epileptic seizure prediction and control. IEEE Trans. Biomed. Eng. 2003; 50(5):549-58.
Jerger, et al. Early seizure detection. Journal of Clin. Neurophysiol. 2001; 18(3):259-68.
Jerger, et al. Multivariate linear discrimination of seizures. Clin. Neurophysiol. 2005; 116(3):545-51.
Jouny, et al. Characterization of epileptic seizure dynamics using Gabor atom density. Clin. Neurophysiol. 2003; 114(3):426-37.
Jouny, et al. Signal complexity and synchrony of epileptic seizures: is there an identifiable preictal period? Clin. Neurophysiol. 2005; 116(3):552-8.
Kapiris, et al. Similarities in precursory features in seismic shocks and epileptic seizures. Europhys. Lett. 2005; 69(4):657-663.
Katz, et al. Does interictal spiking change prior to seizures? Electroencephalogr. Clin. Neurophysiol. 1991; 79 (2):153-6.
Kerem, et al. Forecasting epilepsy from the heart rate signal. Med. Biol. Eng. Comput. 2005; 43(2):230-9.
Khalilov, et al. Epileptogenic actions of GABA and fast oscillations in the developing hippocampus. Neuron. 2005; 48(5):787-96.
Korn, et al. Is there chaos in the brain? II. Experimental evidence and related models. C. R. Biol. 2003; 326 (9):787-840.

(56) References Cited

OTHER PUBLICATIONS

Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006 (106 pp).
Kreuz, et al. Measure profile surrogates: a method to validate the performance of epileptic seizure prediction algorithms. Phys. Rev. E. 2004; 69(6 Pt 1):061915-1-9.
Lachaux, et al. Measuring phase synchrony in brain signals. Hum. Brain Mapp. 1999; 8(4):194-208.
Lai, et al. Controlled test for predictive power of Lyapunov exponents: their inability to predict epileptic seizures. Chaos. 2004; 14(3):630-42.
Lai, et al. Inability of Lyapunov exponents to predict epileptic seizures. Phys. Rev. Lett. 2003; 91(6):068102-1-4.
Latka, et al. Wavelet analysis of epileptic spikes. Phys. Rev. E. 2003; 67(5 Pt 1):052902 (6 pages).
Le Van Quyen, et al. Anticipating epileptic seizures in real time by a non-linear analysis of similarity between EEG recordings. Neuroreport. 1999; 10(10):2149-55.
Le Van Quyen, et al. Author's second reply. The Lancet. 2003; 361:971.
Le Van Quyen, et al. Comparison of Hilbert transform and wavelet methods for the analysis of neuronal synchrony. J. Neurosci. Methods. 2001; 111(2):83-98.
Le Van Quyen, et al. Nonlinear analyses of interictal EEG map the brain interdependences in human focal epilepsy. Physica D. 1999; 127:250-266.
Le Van Quyen, et al. Preictal state identification by synchronization changes in long-term intracranial EEG recordings. Clin. Neurophysiol. 2005; 116(3):559-68.
Le Van Quyen, M. Anticipating epileptic seizures: from mathematics to clinical applications. C. R. Biol. 2005; 328(2):187-98.
Lehnertz, et al. Nonlinear EEG analysis in epilepsy: its possible use for interictal focus localization, seizure anticipation, and prevention. J. Clin. Neurophysiol. 2001; 18(3):209-22.
Lehnertz, et al. Seizure prediction by nonlinear EEG analysis. IEEE Eng. Med. Biol. Mag. 2003; 22(1):57-63.
Lehnertz, et al. The First International Collaborative Workshop on Seizure Prediction: summary and data description. Clin. Neurophysiol. 2005; 116(3):493-505.
Lehnertz, K. Non-linear time series analysis of intracranial EEG recordings in patients with epilepsy—an overview. Int. J. Psychophysiol. 1999; 34(1):45-52.
Lemos, et al. The weighted average reference montage. Electroencephalogr. Clin. Neurophysiol. 1991; 79(5):361-70.
Li, et al. Fractal spectral analysis of pre-epileptic seizures in terms of criticality. J. Neural Eng. 2005; 2(2):11-16.
Li, et al. Linear and nonlinear measures and seizure anticipation in temporal lobe epilepsy. J. Comput. Neurosci. 2003; 15(3):335-45.
Li, et al. Non-linear, non-invasive method for seizure anticipation in focal epilepsy. Math. Biosci. 2003; 186(1):63-77.
Litt, et al. Prediction of epileptic seizures. Lancet Neurol. 2002; 1(1):22-30.
Litt, et al. Seizure prediction and the preseizure period. Curr. Opin. Neurol. 2002; 15(2):173-7.
Maiwald, et al. Comparison of three nonlinear seizure prediction methods by means of the seizure prediction characteristic. Physica D. 2004; 194:357-368.
Mangasarian, et al. Lagrangian Support Vector Machines. Journal of Machine Learning Research. 2001; 1:161-177.
Martinerie, et al. Epileptic seizures can be anticipated by non-linear analysis. Nat. Med. 1998; 4(10):1173-6.
McSharry, et al. Comparison of predictability of epileptic seizures by a linear and a nonlinear method. IEEE Trans. Biomed. Eng. 2003; 50(5):628-33.
McSharry, et al. Linear and non-linear methods for automatic seizure detection in scalp electro-encephalogram recordings. Med. Biol. Eng. Comput. 2002; 40(4):447-61.
McSharry, P. E. Detection of dynamical transitions in biomedical signals using nonlinear methods. Lecture Notes in Computer Science 2004; 3215:483-490.
Meng, et al. Gaussian mixture models of ECoG signal features for improved detection of epileptic seizures. Med. Eng. Phys. 2004; 26(5):379-93.
Mizuno-Matsumoto, et al. Wavelet-crosscorrelation analysis can help predict whether bursts of pulse stimulation will terminate after discharges. Clin. Neurophysiol. 2002; 113(1):33-42.
Mormann, et al. Automated detection of a preseizure state based on a decrease in synchronization in intracranial electroencephalogram recordings from epilepsy patients. Phys. Rev. E. 2003; 67(2 Pt 1):021912-1-10.
Mormann, et al. Epileptic seizures are preceded by a decrease in synchronization. Epilepsy Res. 2003; 53(3):173-85.
Mormann, et al. Mean phase coherence as a measure for phase synchronization and its application to the EEG of epilepsy patients. Physica D. 2000; 144:358-369.
Mormann, et al. On the predictability of epileptic seizures. Clin. Neurophysiol. 2005; 116(3):569-87.
Mormann, et al. Seizure anticipation: from algorithms to clinical practice. Curr. Opin. Neurol. 2006; 19(2):187-93.
Navarro, et al. Seizure anticipation in human neocortical partial epilepsy. Brain. 2002; 125:640-55.
Navarro, et al. Seizure anticipation: do mathematical measures correlate with video-EEG evaluation? Epilepsia. 2005; 46(3):385-96.
Niederhauser, et al. Detection of seizure precursors from depth-EEG using a sign periodogram transform. IEEE Trans. Biomed. Eng. 2003; 50(4):449-58.
Nigam, et al. A neural-network-based detection of epilepsy. Neurological Research. 2004; 26(1):55-60.
Osorio, et al. Automated seizure abatement in humans using electrical stimulation. Anna Neurol. 2005; 57(2):258-68.
Osorio, et al. Performance reassessment of a real-time seizure-detection algorithm on long ECoG series. Epilepsia. 2002; 43(12):1522-35.
Osorio, et al. Real-time automated detection and quantitative analysis of seizures and short-term prediction of clinical onset. Epilepsia. 1998; 39(6):615-27.
Ossadtchi, et al. Hidden Markov modelling of spike propagation from interictal MEG data. Phys. Med. Biol. 2005; 50(14):3447-69.
Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.
Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.
Platt, et al. Large Margin DAGs for Multiclass Classification. S.A. Solla. T.K. Leen adn K. R. Muller (eds.). 2000; pp. 547-553.
Platt, J. C. Using Analytic QP and Sparseness to Speed Training of Support Vector Machines. Advances in Neural Information Processing Systems. 1999; 11:557-563.
Protopopescu, et al. Epileptic event forewarning from scalp EEG. J. Clin. Neurophysiol. 2001; 18(3):223-45.
Rahimi, et al. On the Effectiveness of Aluminum Foil Helmets: An Empirical Study. Available at http://people.csail.mit.edu/rahimi/helmet/. Accessed Mar. 2, 2006.
Robinson, et al. Steady States and Global Dynamics of Electrical Activity in the Cerebral Cortex. Phys. Rev. E. 1998; (58):3557-3571.
Rudrauf, et al. Frequency flows and the time-frequency dynamics of multivariate phase synchronization in brain signals. NeuroImage. 2005. (19 pages).
Saab, et al. A system to detect the onset of epileptic seizures in scalp EEG. Clin. Neurophysiol, 2005; 116:427-442.
Sackellares et al. Computer-Assisted Seizure Detection Based on Quantitative Dynamical Measures. American Electroencephalographic Society Annual Meeting, Sep. 1994.
Sackellares et al. Dynamical Studies of Human Hippocampin Limbic Epilepsy. Neurology. 1995; 45, Suppl. 4, pp. A 404.

(56) References Cited

OTHER PUBLICATIONS

Sackellares et al. Epileptic Seizures as Neural Resetting Mechanisms. Epilepsia. 1997; vol. 38, Sup. 3.
Sackellares et al. Measurement of Chaos to Localize Seizure Onset. Epilepsia. 1989; 30(5):663.
Sackellares et al. Relationship Between Hippocampal Atrophy and Dynamical Measures of EEG in Depth Electrode Recordings. American Electroencephalographic Society Annual Meeting, Sep. 1995. pp. A105.
Sackellares, J. C. Epilepsy—when chaos fails. In: chaos in the brain? Eds. K. Lehnertz & C.E. Elger. World Scientific. 2000 (22 pages).
Salant, et al. Prediction of epileptic seizures from two-channel EEG. Med. Biol. Eng. Comput. 1998; 36 (5):549-56.
Schelter, et al. Testing for directed influences among neural signals using partial directed coherence. J. Neurosci. Methods. 2006; 152(1-2):210-9.
Schindler, et al. EEG analysis with simulated neuronal cell models helps to detect pre-seizure changes. Clin. Neurophysiol. 2002; 113(4):604-14.
Schwartzkroin, P. Origins of the Epileptic State. Epilepsia. 1997; 38, supply. 8, pp. 853-858.
Sheridan, T. Humans and Automation. NY: John Wiley. 2002.
Shoeb et al. Patient-specific seizure detection. MIT Computer Science and Artificial Intelligence Laboratory. 2004; pp. 193-194.
Staba, et al. Quantitative analysis of high-frequency oscillations (80-500 Hz) recorded in human epileptic hippocampand entorhinal cortex. J. Neurophysiol. 2002; 88(4):1743-52.
Stefanski, et al. Using chaos synchronization to estimate the largest Lyapunov exponent of nonsmooth systems. Discrete Dynamics in Nature and Society. 2000; 4:207-215.
Subasi, et al. Classification of EEG signals using neural network and logistic regression. Computer Methods Programs Biomed. 2005; 78(2):87-99.
Szoka et al. Procedure for preparation of liposomes with large internal aqueospace and high capture volume by reverse phase evaporation. 1978. Proc. Natl Acad. Sci. USA. 75: 4194-4198.
Tass, et al. Detection of n: m Phase Locking from Noisy Data: Application to Magnetoencephalography. Physical Review Letters. 1998; 81(15):3291-3294.
Terry, et al. An improved algorithm for the detection of dynamical interdependence in bivariate time-series. Biol. Cybern. 2003; 88(2):129-36.
Tetzlaff, et al. Cellular neural networks (CNN) with linear weight functions for a prediction of epileptic seizures. Int'l. J. of Neural Systems. 2003; 13(6):489-498.
Theiler, et al. Testing for non-linearity in time series: the method of surrogate data. Physica D. 1992; 58:77-94.
Tsakalis, K. S. Prediction and control of epileptic seizures: Coupled oscillator models. Arizona State University. (Slide: 53 pages) (No date).
Van Drongelen, et al. Seizure anticipation in pediatric epilepsy: use of Kolmogorov entropy. Pediatr. Neurol. 2003; 29(3): 207-13.
Van Putten, M. Nearest neighbor phase synchronization as a measure to detect seizure activity from scalp EEG recordings. J. Clin. Neurophysiol. 2003; 20(5):320-5.
Venugopal, et al. A new approach towards predictability of epileptic seizures: KLT dimension. Biomed Sci. Instrum. 2003; 39:123-8.
Vonck, et al. Long-term amygdalohippocampal stimulation for refractory temporal lobe epilepsy. Ann. Neurol. 2002; 52(5):556-65.
Vonck, et al. Long-term deep brain stimulation for refractory temporal lobe epilepsy. Epilepsia. 2005; 46(Suppl 5):98-9.
Vonck, et al. Neurostimulation for refractory epilepsy. Acta. Neurol. Belg. 2003; 103(4):213-7.
Weiss, P. Seizure prelude found by chaos calculation. Science News. 1998; 153(20):326.
Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.
Widman, et al. Reduced signal complexity of intracellular recordings: a precursor for epileptiform activity? Brain Res. 1999; 836(1-2):156-63.
Winterhalder, et al. Sensitivity and specificity of coherence and phase synchronization analysis. (In Press) Phys. Lett. A. 2006.
Winterhalder, et al. The seizure prediction characteristic: a general framework to assess and compare seizure prediction methods. Epilepsy Behav. 2003; 4(3):318-25.
Yang, et al. A supervised feature subset selection technique for multivariate time series. Available at http://infolab.usc.edu/DocsDemos/fsdm05.pdf. Accessed Mar. 2, 2006.
Yang, et al. CLe Ver: A feature subset selection technique for multivariate time series. T. B. Ho, D. Cheung, and H. Liu (Eds.): PAKDD. 2005; LNAI 3518: 516-522.
Yang, et al. Relation between Responsiveness to Neurotransmitters and Complexity of Epileptiform Activity in Rat Hippocampal CA1 Neurons. Epilepsia. 2002; 43(11):1330-1336.
Yatsenko, et al. Geometric Models, Fiber Bundles, and Biomedical Applications. Proceedings of Institute of Mathematics of NAS of Ukraine. 2004; 50 (Part 3):1518R1525.
Zaveri et al. Time-Frequency Analyses of Nonstationary Brain Signals. Electroencephalography and Clinical Neurophysiology. 1991; 79, pp. 28P-29P.
Zhang, et al. High-resolution EEG: cortical potential imaging of interictal spikes. Clin. Neurophysiol. 2003; 114(10):1963-73.
DiLorenzo, Daniel, U.S. Appl. No. 11/743,607, entitled "Controlling a Subject's Susceptibility to a Seizure," filed May 2, 2007.
DiLorenzo, Daniel, U.S. Appl. No. 11/282,317 entitled "Closed-loop vagus nerve stimulation," filed Nov. 17, 2005.
Harris, John, U.S. Appl. No. 11/734,190, entitled "Methods and Template Assembly for Implanting an Electrode Array in a Patient," filed Apr. 11, 2007.
Leyde et al.; U.S. Appl. No. 12/020,507 entitled "Methods and systems for measuring a subject's susceptibility to a seizure," filed Jan. 25, 2008.
Snyder et al.; U.S. Appl. No. 12/020,450 entitled "Systems and methods for identifying a contra-ictal condition in a subject," filed Jan. 25, 2008.
Snyder et al.; U.S. Appl. No. 12/035,335 entitled "Methods and systems for characterizing and generating a patient-specific seizure prediction system," filed Feb. 21, 2008.
Snyder et al.; U.S. Appl. No. 12/053,312 entitled "Implantable systems and methods for identifying a contra-ictal condition in a subject," filed Mar. 21, 2008.
DiLorenzo, Daniel; U.S. Appl. No. 12/177,060 entitled "Closed-loop feedback-driven neuromodulation," filed Jul. 21, 2008.
Chen et al.; Clinical utility of video-EEG monitoring; Perdiatric Neurology; vol. 12; No. 3; pp. 220-224; 1995.
Snyder et al; The statistics of a practical seizure warning system; Journal of Neural Engineering; vol. 5; pp. 392-401; 2008.
Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.
Franaszczuk et al.; An autoregressive method for the measurement of synchronization of interictal and ictal EEG signals; Biological Cybernetics, vol. 81; No. 1; pp. 3-9; 1999.
Mormann et al.; Seizure prediction: the long and winding road; Brain; vol. 130; No. 2; pp. 314-333; Sep. 28, 2006.
Sackellares et al.; Predictability analysis for an automated seizure prediction algorithm; Journal of Clinical Neurophysiology; vol. 23; No. 6; pp. 509-520; Dec. 2006.
Schelter et al.; Testing statistical significance of multivariate time series analysis techniques for epileptic seizure prediction; Chaos: An Interdisciplinary Journal of Nonlinear Science; vol. 16; No. 013108; pp. 1-10; Jan. 2006.
Wong et al.; A stochastic framework for evaluating seizure prediction algorithms using hiden markov models; Journal of Neurophysiology; vol. 97, No. 3; pp. 2525-2532; Oct. 4, 2006.
Yang et al.; Testing whether a prediction scheme is better than guess; Ch. 14 in Quantitative Neuroscience: Models, Algorithms, Diagnostics, and Therapeutic Applications; pp. 252-262; 2004.

(56) References Cited

OTHER PUBLICATIONS

Spector et al., "High and Low Perceived Self-Control of Epileptic Seizures", Epilepsia, vol. 42 (4). pp. 556-564, (Apr. 2001).
Non-Final Office Action dated Jun. 12, 2013 in U.S. Appl. No. 12/020,450, filed Jan. 25, 2008.
Final Office Action dated Mar. 13, 2014 in U.S. Appl. No. 12/020,450, filed Jan. 25, 2008.

* cited by examiner

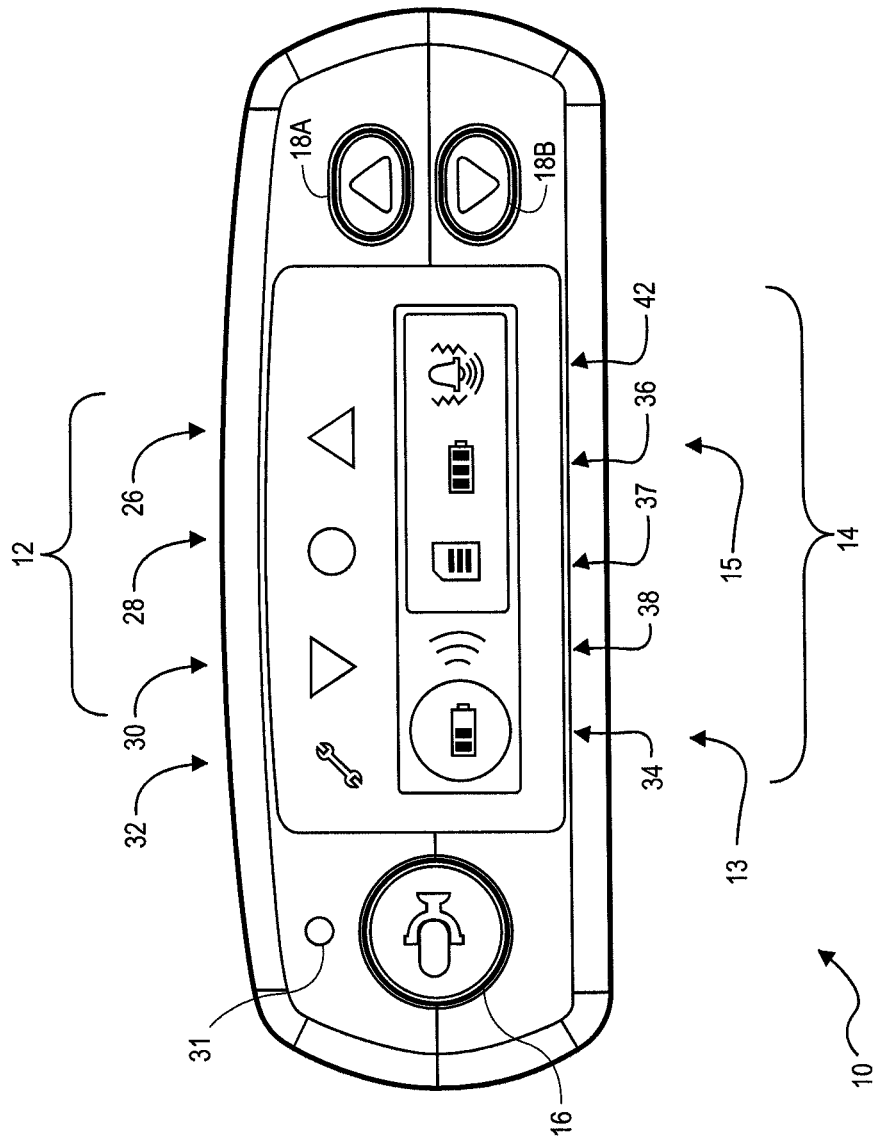

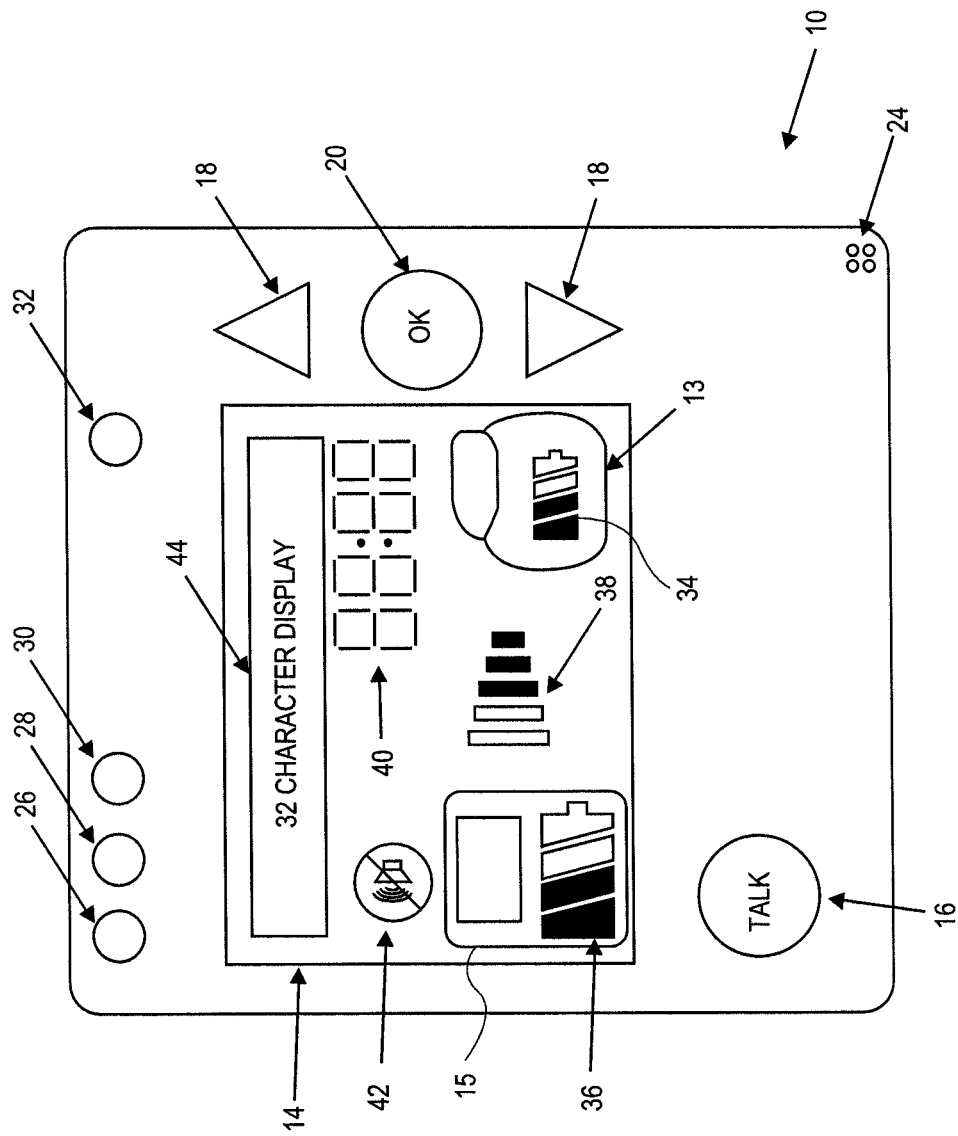

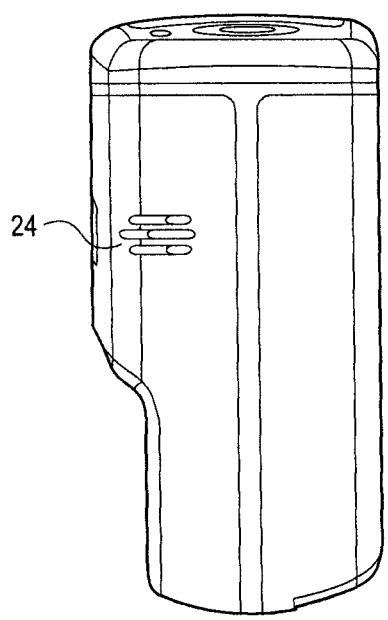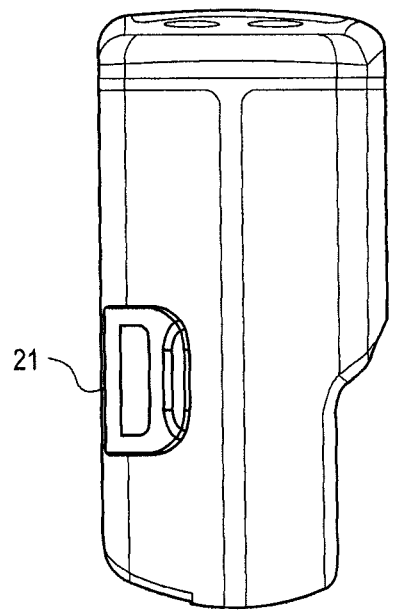
FIG. 3E  FIG. 3F
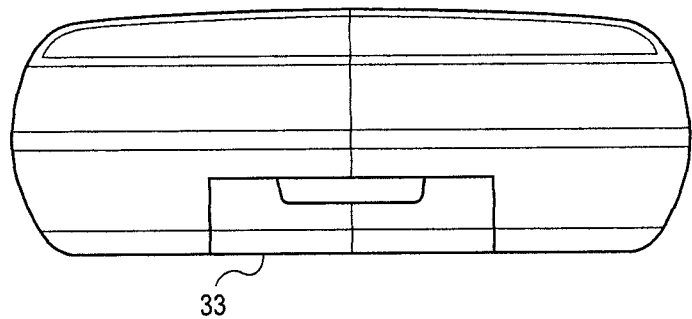
FIG. 3G

SAFE

PREDICTION

DETECTION

Data card full
Time 12:30 AM
Notification Tone OFF
Refer to User Instructions

ITU OK
ITU battery level 1/3 capacity
ITU battery is charging
Signal strength excellent
PAD OK
PAD battery level 2/3 capacity Text Messages:
Data Card Reminder/Full/Error <CHECK DATA CARD>
Reference to Instruction Manual <SEE USER MANUAL>

| | Prediction algorithm output - Detection algorithm output | | | |
|---|---|---|---|---|
| Safety algorithm output | 00 | 01 | 11 | 10 |
| 0 | Unknown "Yellow" | Seizure detected "Red flashing" | Seizure detected "Red flashing" | Seizure predicted "Red blinking" |
| 1 | Safe "Green" | Seizure detected "Red flashing" | Seizure detected "Red flashing" | Seizure predicted "Red blinking" |

FIG. 17

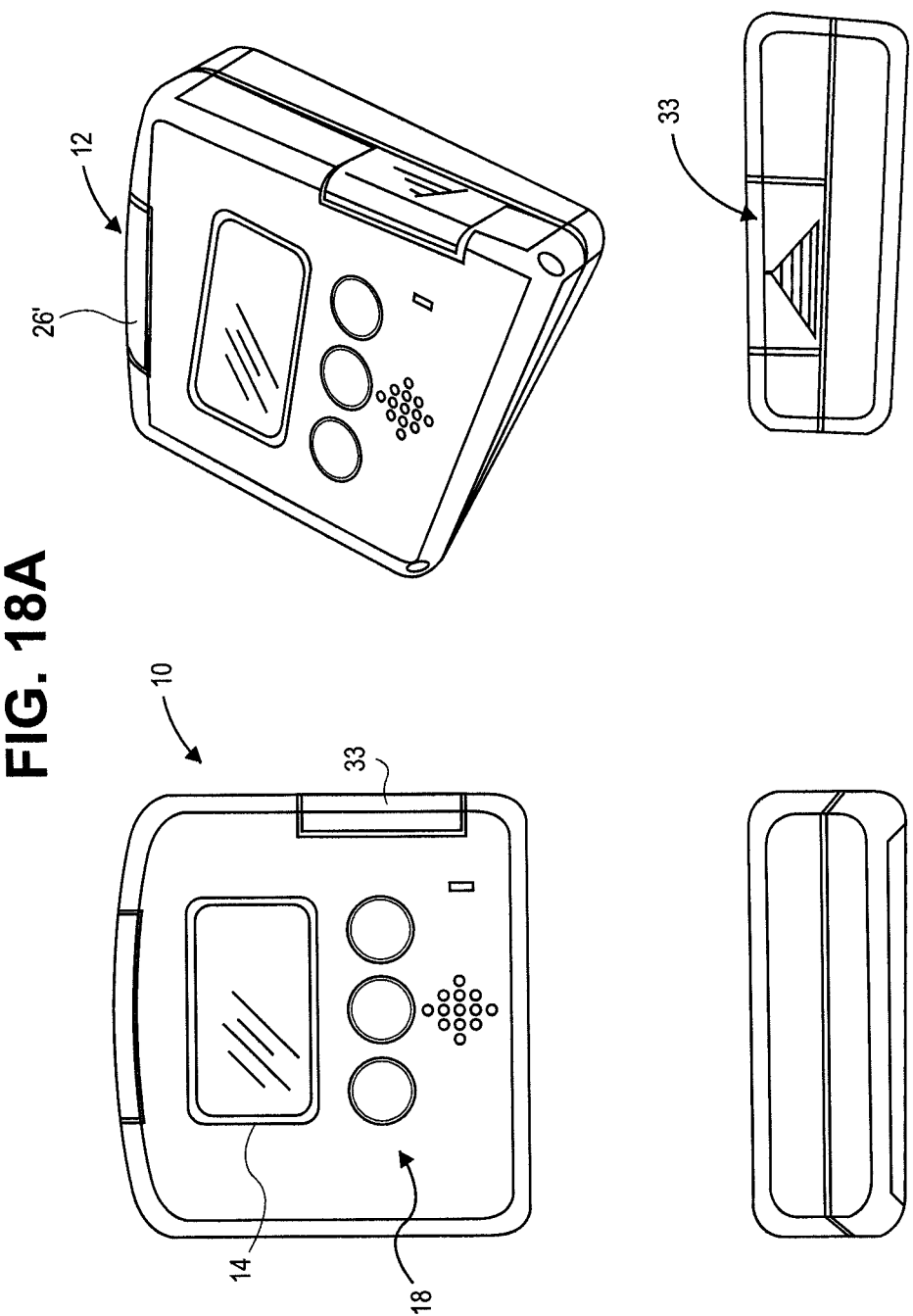

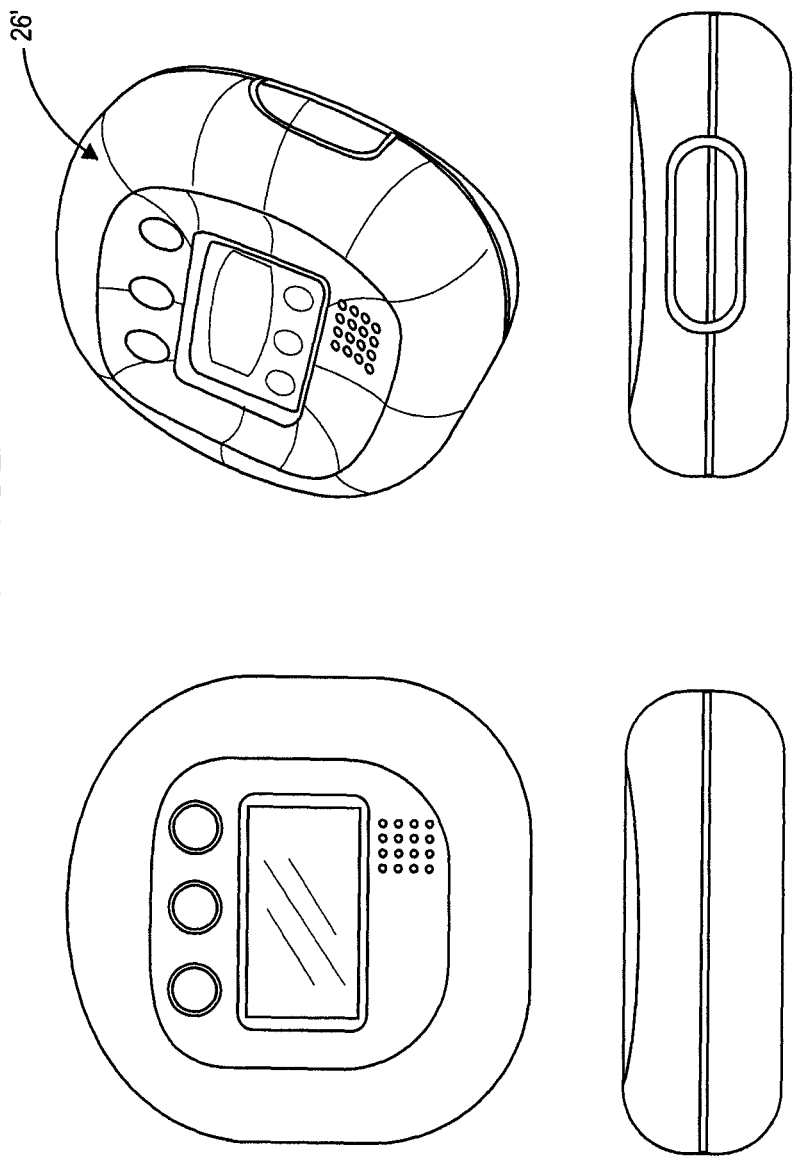

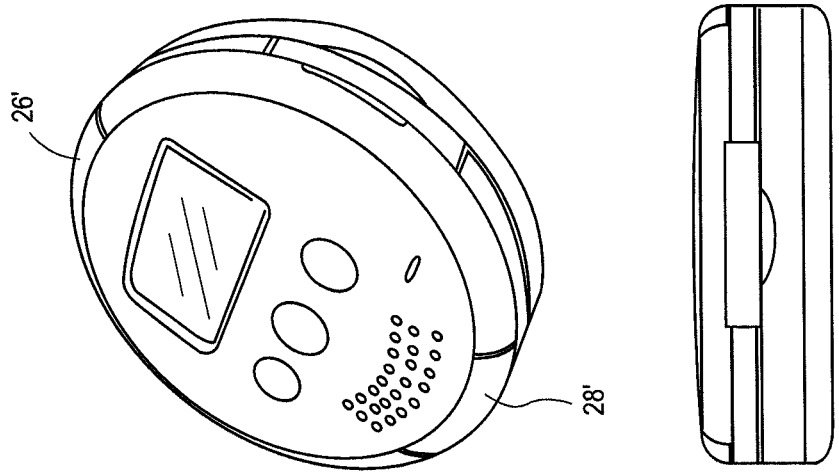
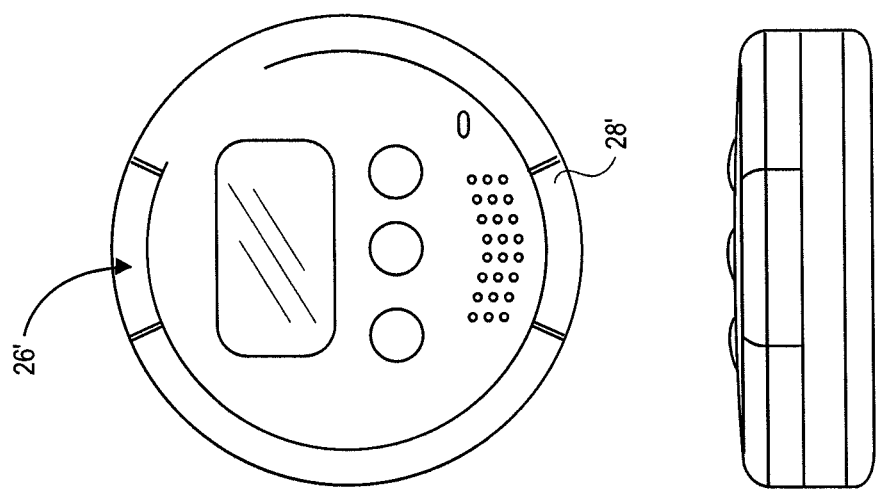
FIG. 18E

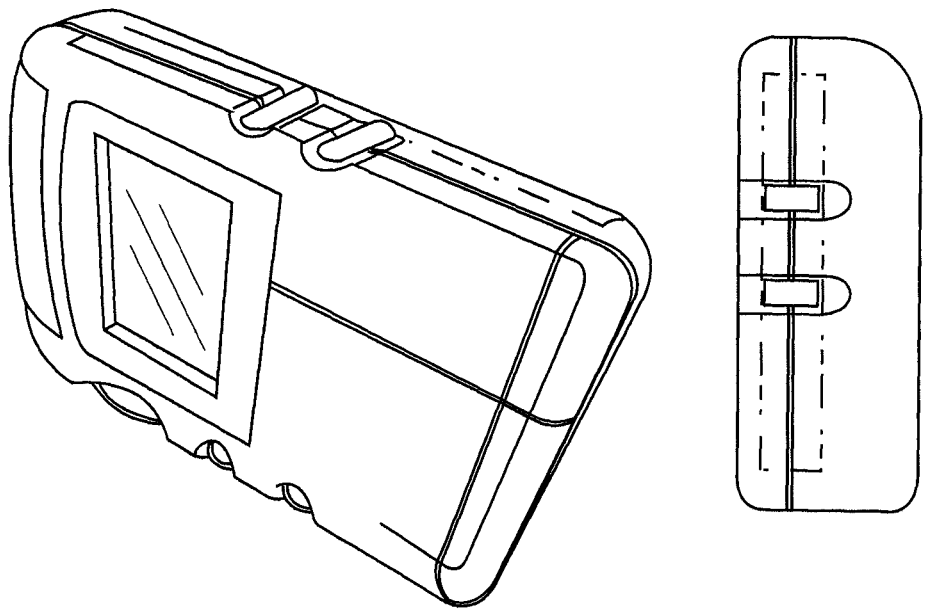
FIG. 18F
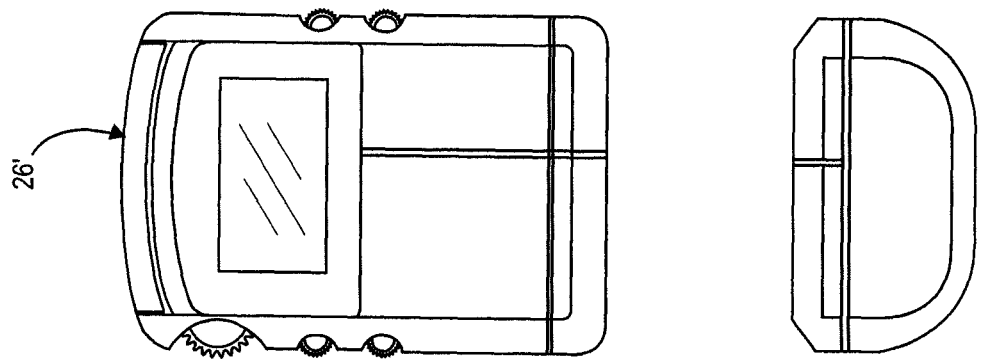

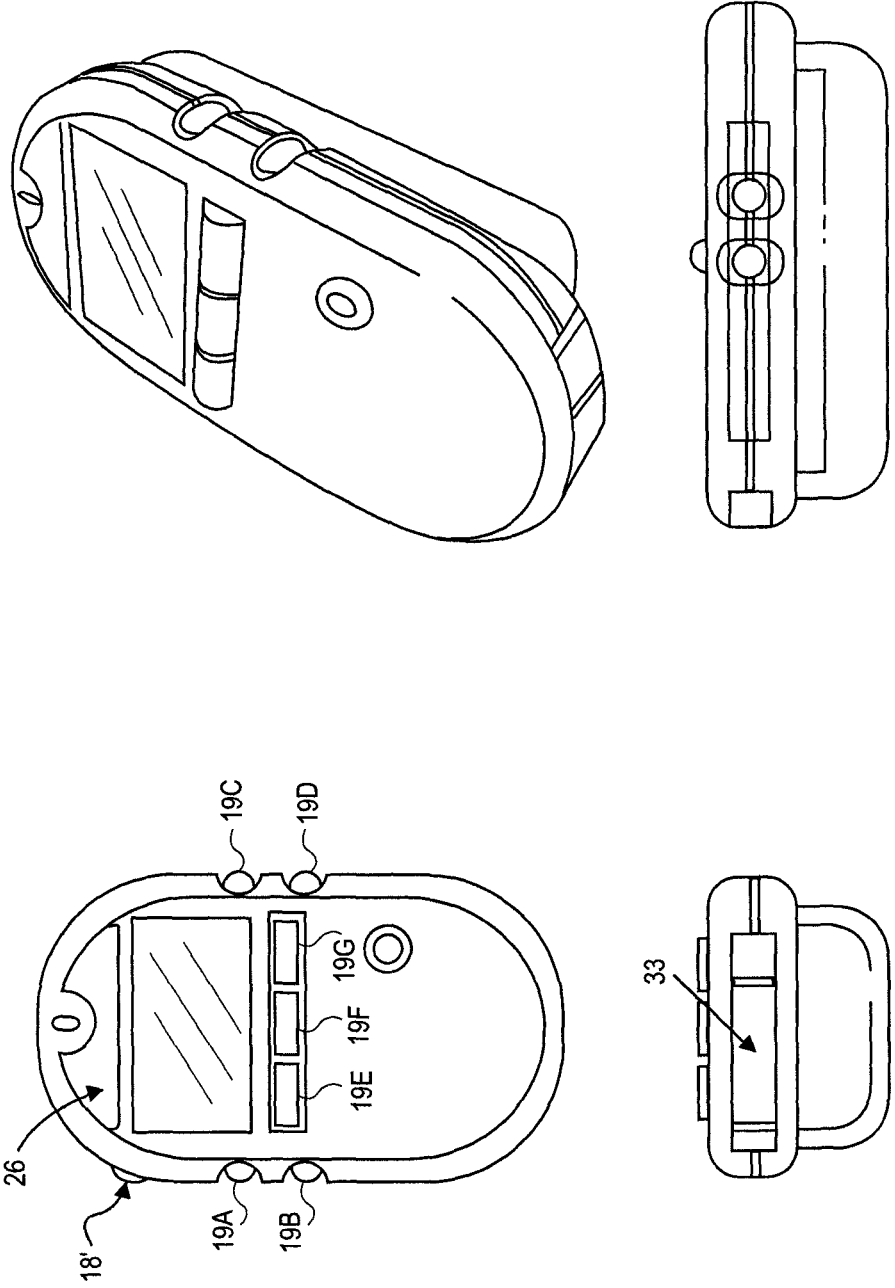

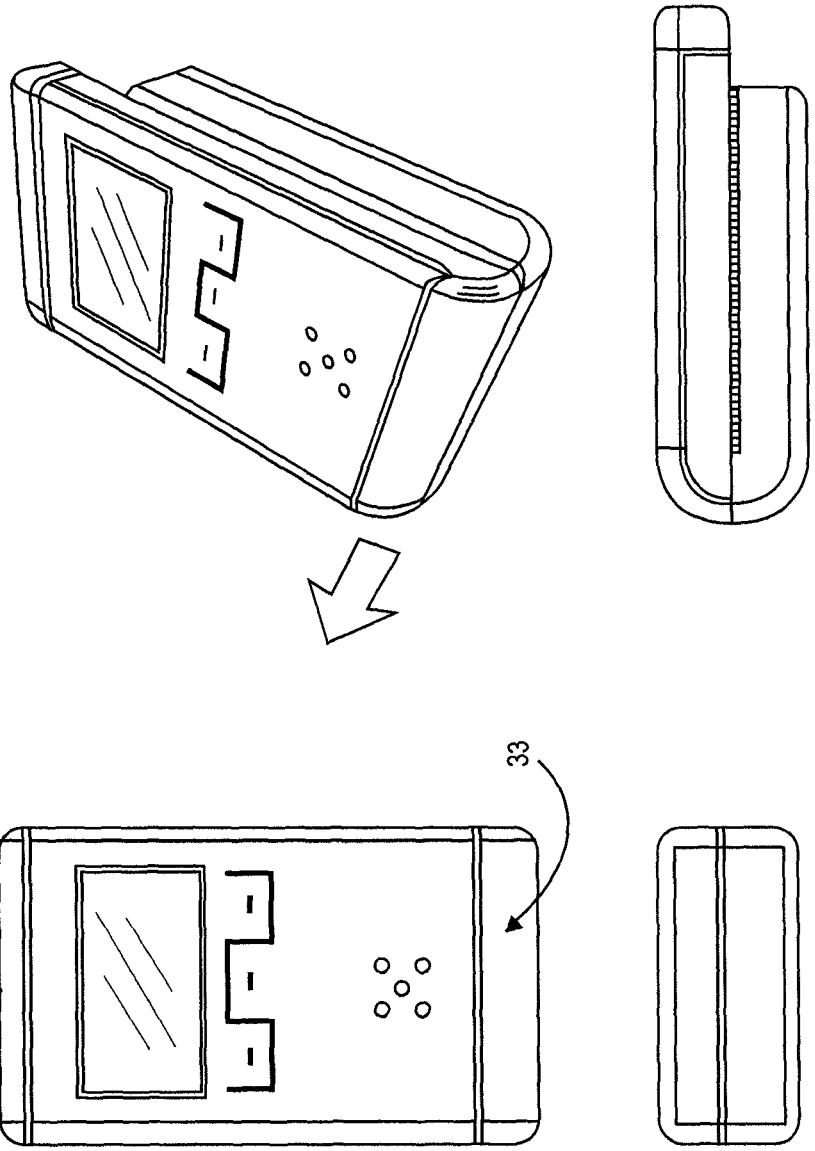

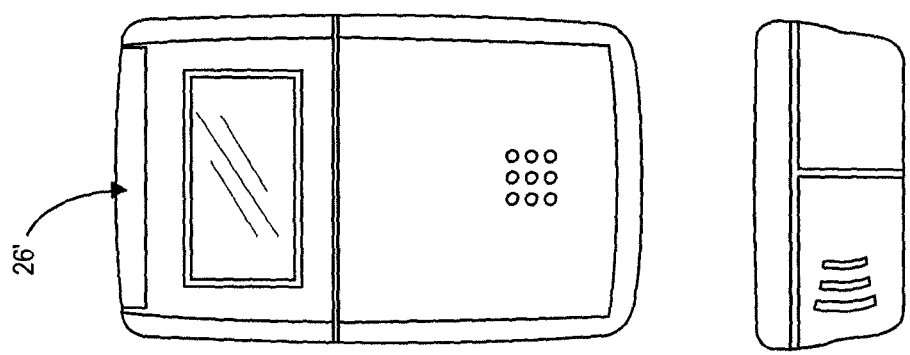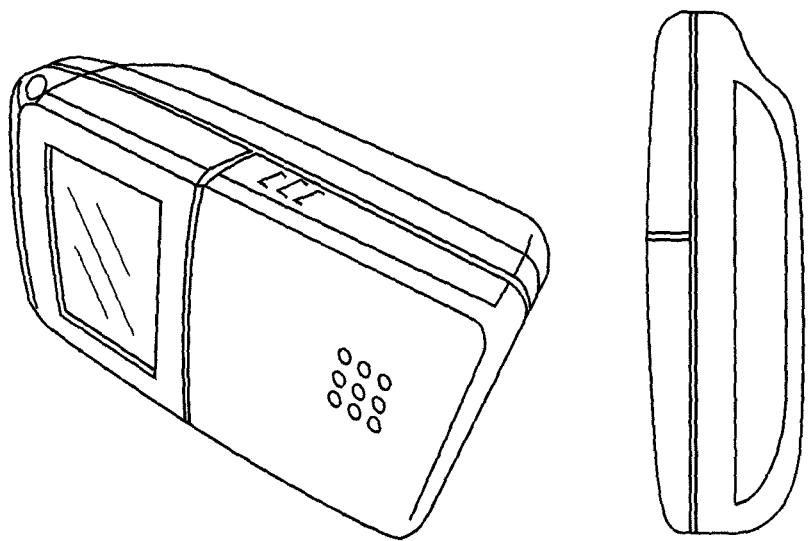
FIG. 18I

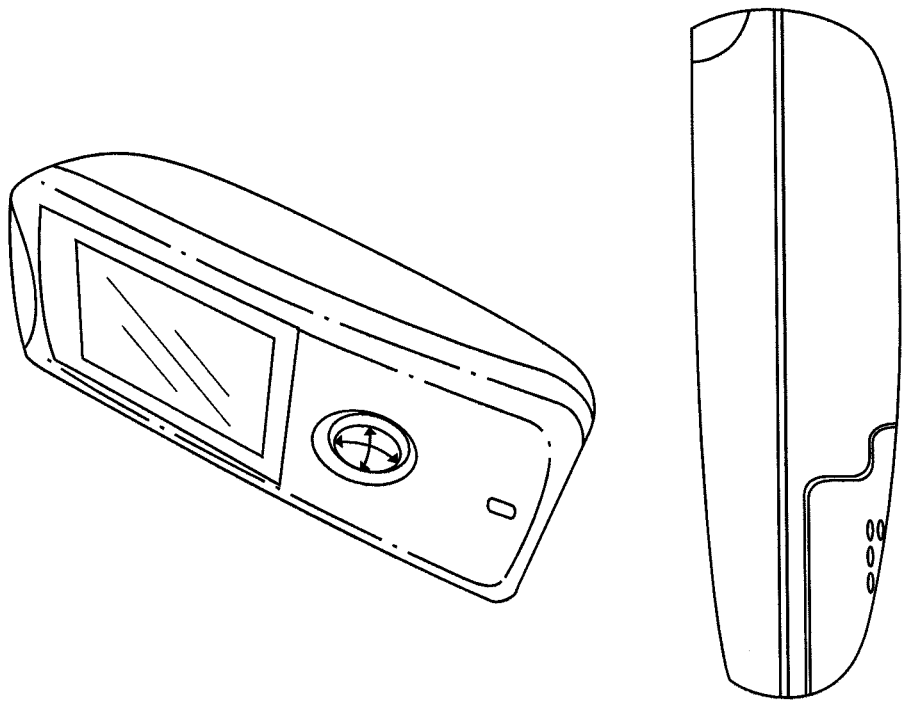
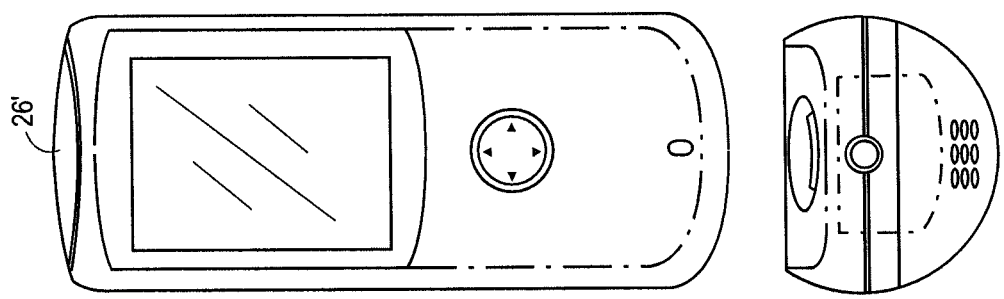
FIG. 18J

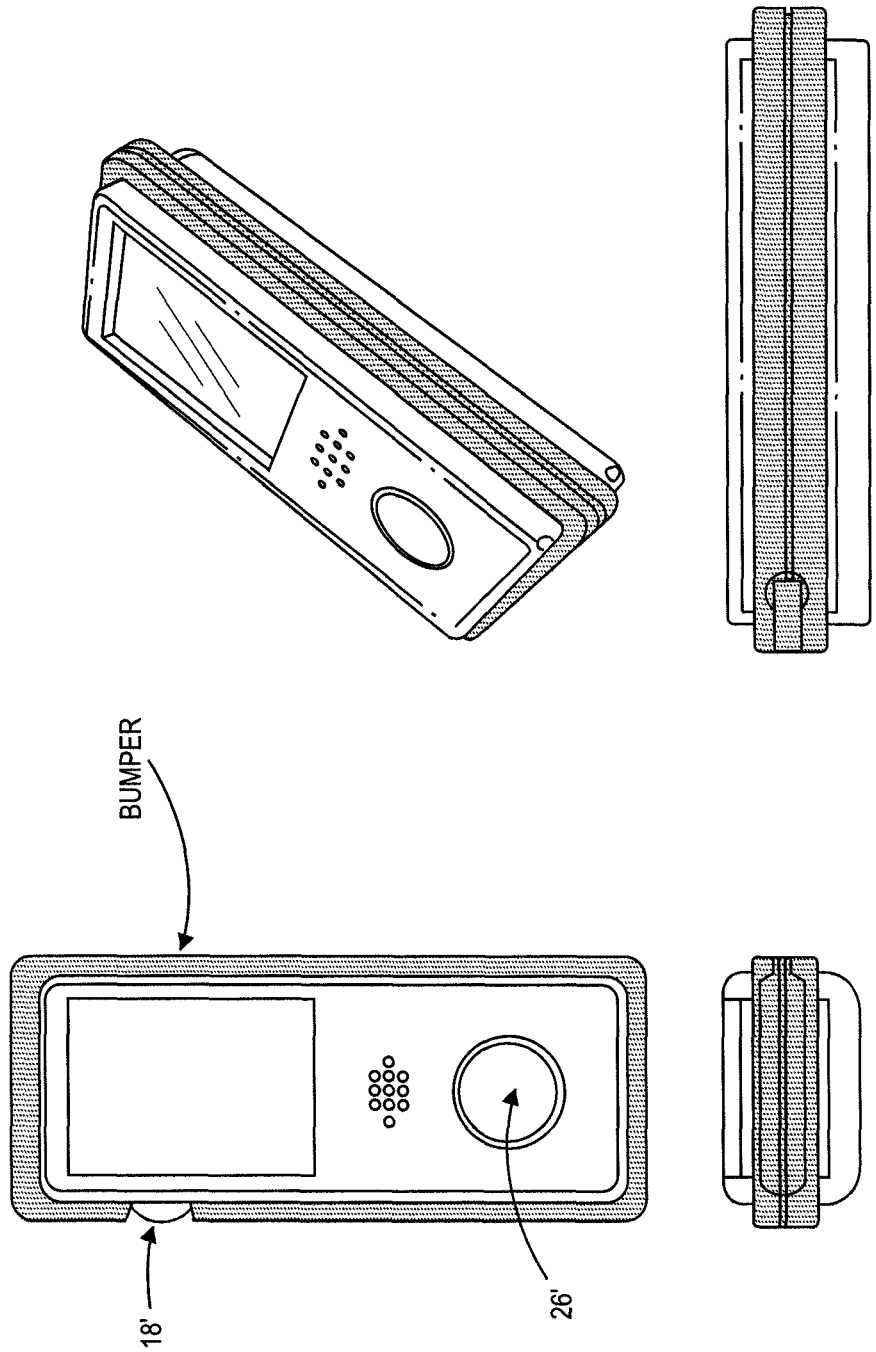

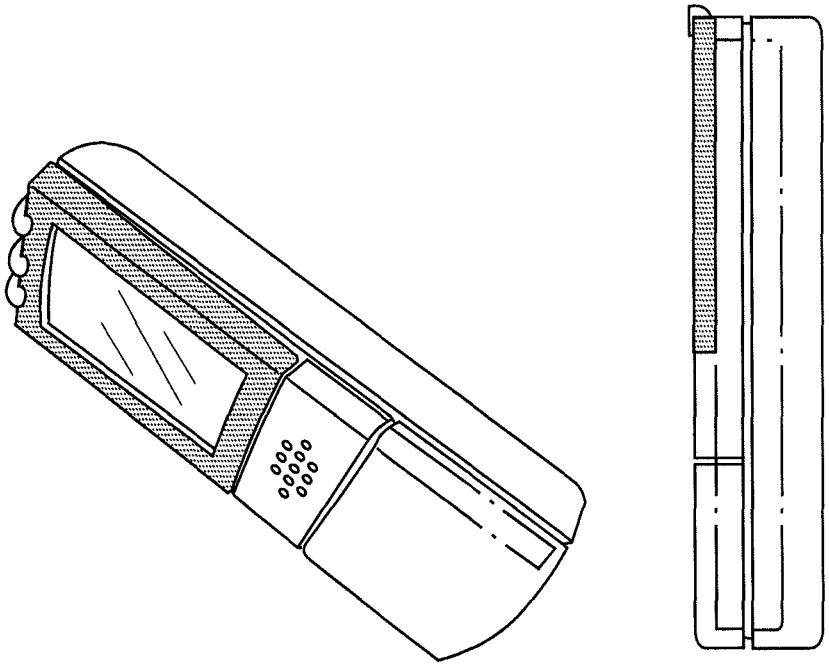
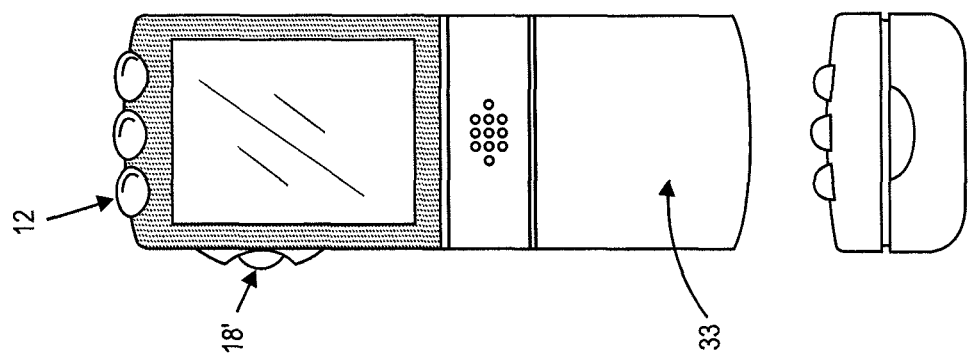
FIG. 18N

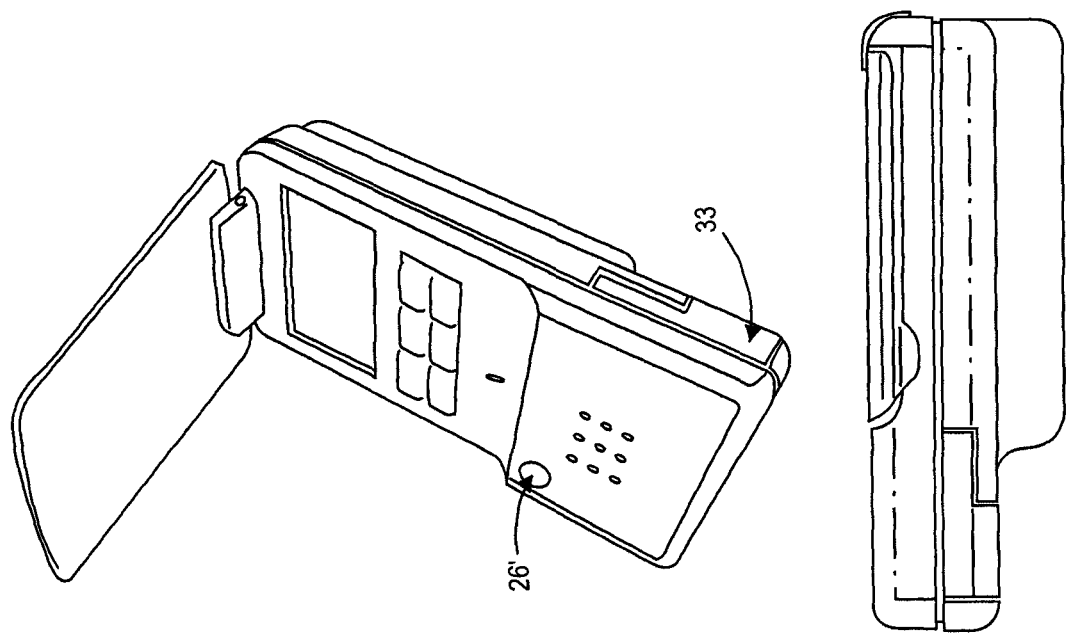
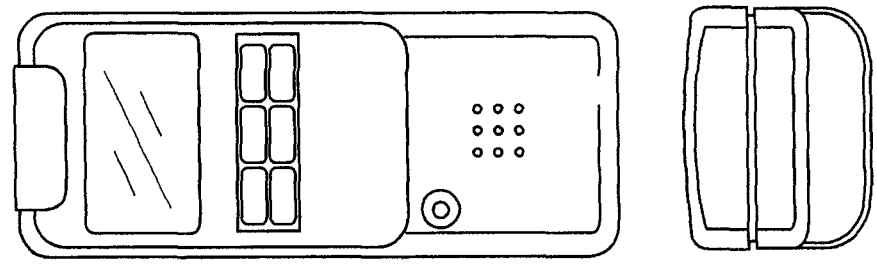
FIG. 18O

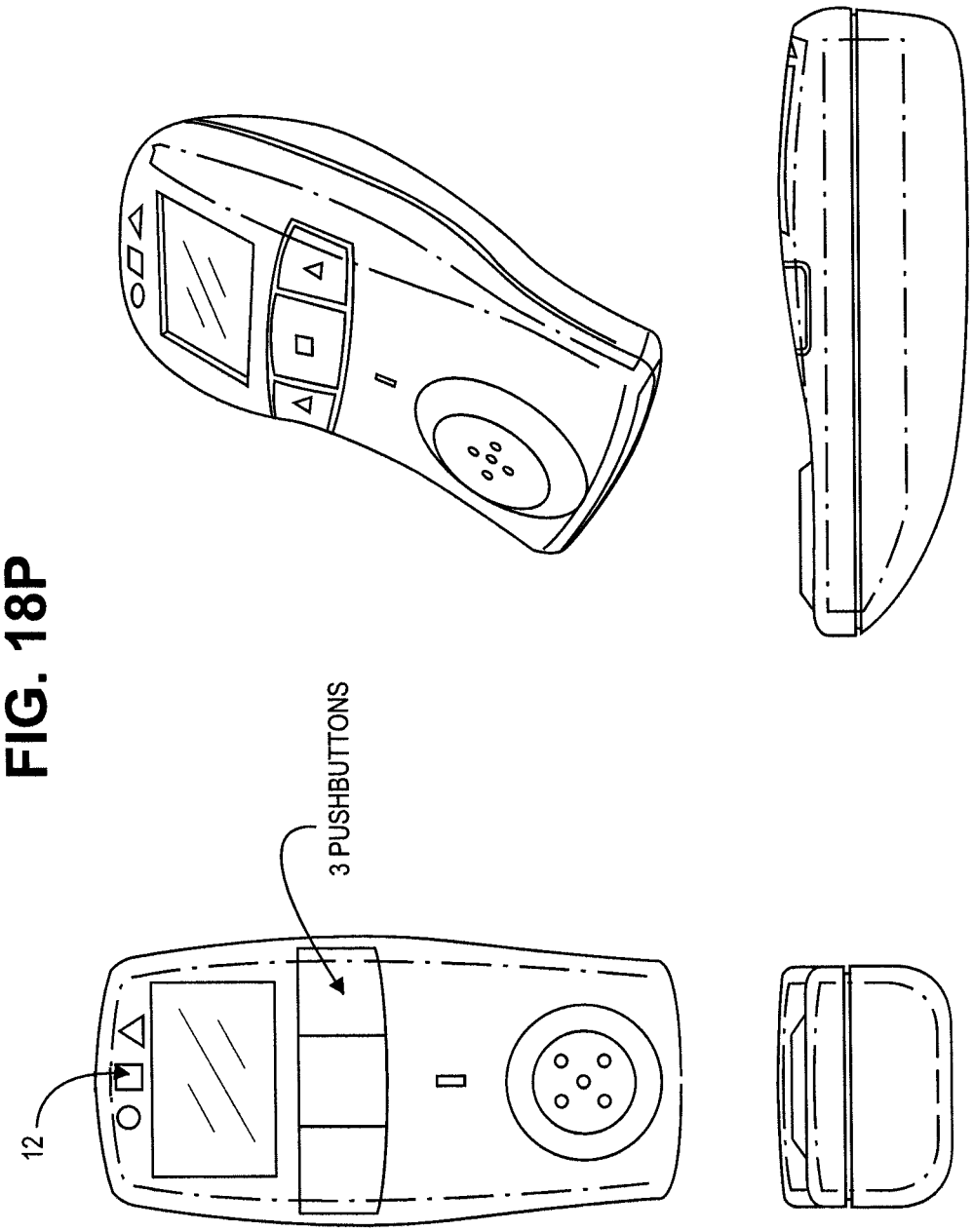

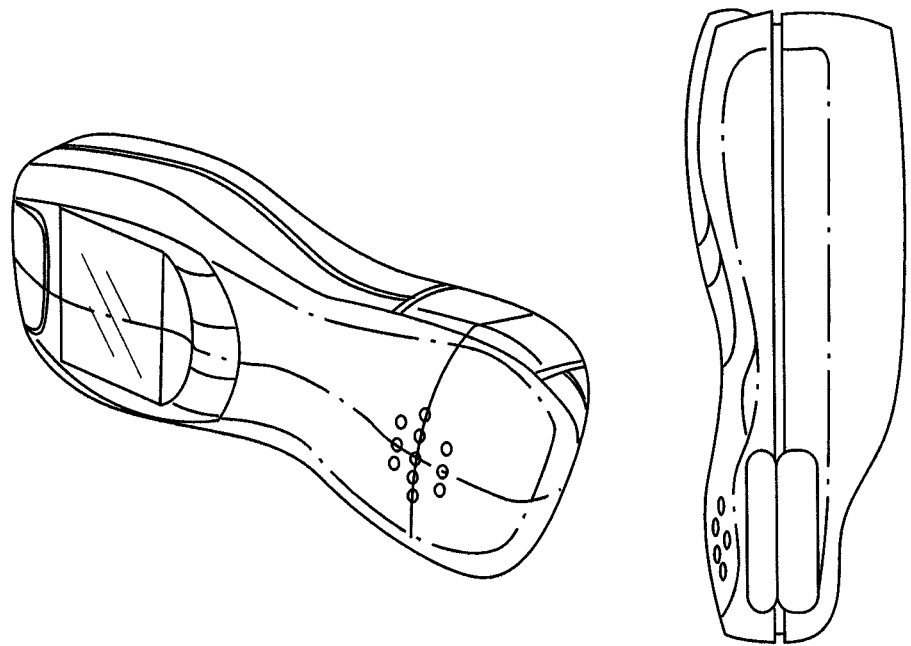
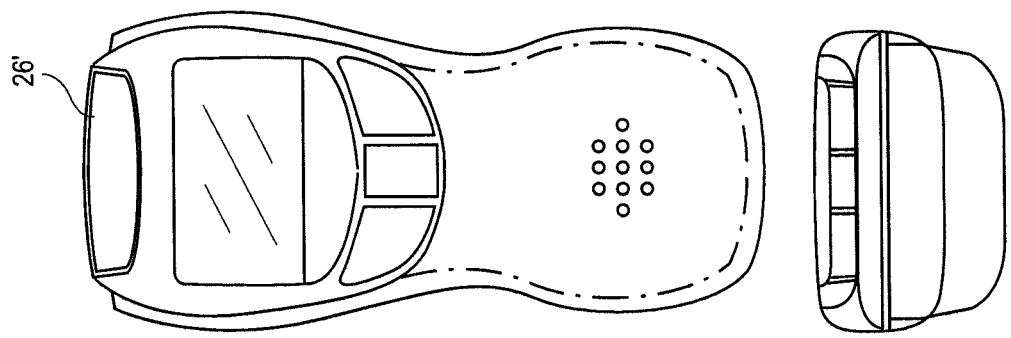
FIG. 18Q

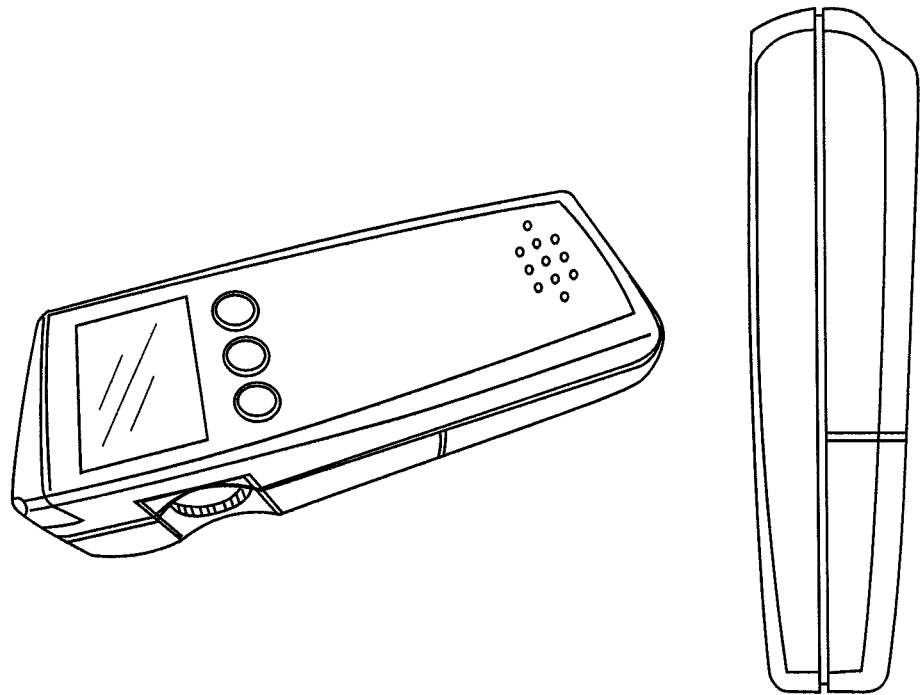
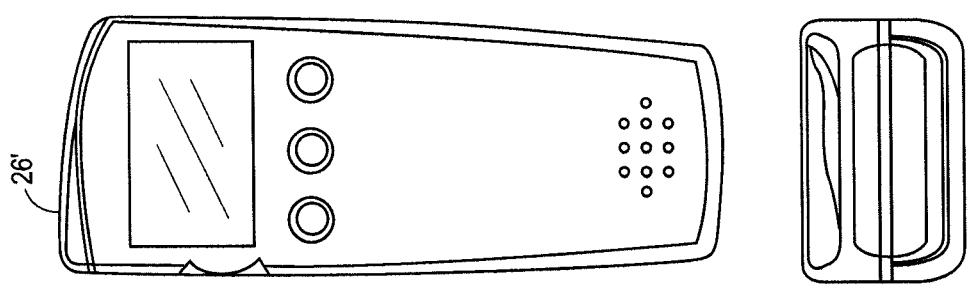
FIG. 18R

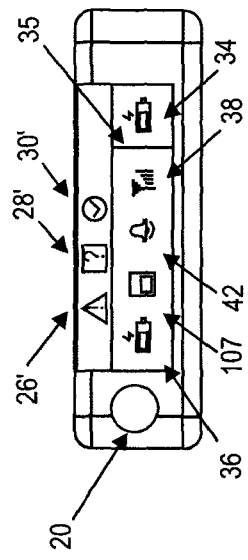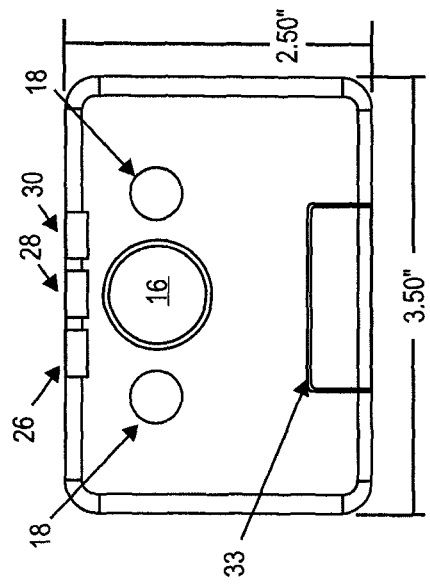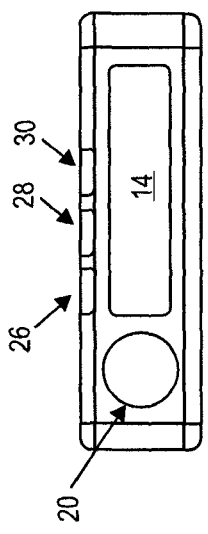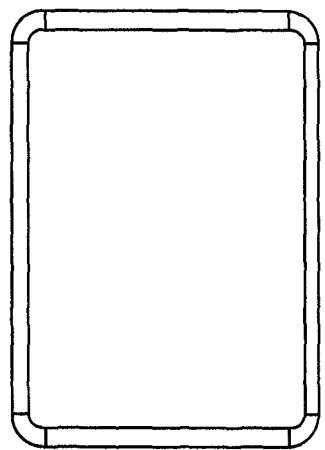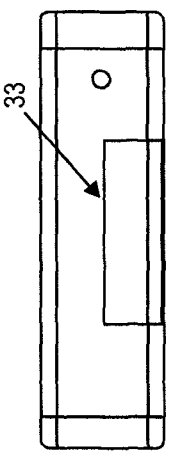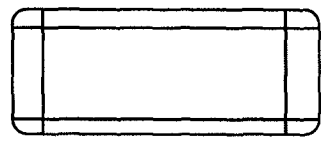

SYSTEMS FOR MONITORING BRAIN ACTIVITY AND PATIENT ADVISORY DEVICE

CROSS-REFERENCE TO RELATED APPLICATIONS

The present application claims the benefit of U.S. Provisional Appiication No. 60/952,463, filed Jul. 27, 2007, the complete disclosure of which is incorporated herein by reference. The present application is related to U.S. patent application Ser. No. 12/020,507, filed Jan, 25, 2008, published as U.S. Patent Publication No. 2008/0183097, abandoned; U.S. patent application Ser. No. 12/020,450, filed Jan. 25, 2008, published as U.S. Patent Publication No, 2008/0183096, pending; and U.S. patent application Ser. No. 12/035,335, filed Feb, 21, 2008, published as U.S. Patent Publication No. 2008/0208074, abandoned, the complete disclosures of which are also incorporated herein by reference.

BACKGROUND OF THE INVENTION

The present invention relates generally to handheld or portable devices. More specifically, the present invention relates to handheld, patient advisory devices that facilitate monitoring of a patient's brain state.

Handheld devices have become an increasingly popular method for an individual to receive and/or transmit information with other individuals or other devices. Cellular phones, personal digital assistants, MP3 players, etc. are common examples of handheld devices being used today. Handheld devices allow for input from the user and output to the user. Input from the user can be in the form of button activations, text typed on a keyboard or a recorded voice memo, and outputs can include audio from an incoming phone call, an email alert, a notification that the device's battery power is low, etc.

Implantable medical devices can be used to monitor biological signals from a patient and transmit the signals to a device external to the patient. For example, both U.S. Pat. No. 3,863,625 to Viglione et al. and U.S. Pat. No. 4,566,464 to Piccone et al. describe epileptic seizure warning system which purportedly provide a warning to the patient of an imminent seizure. Both Viglione and Piccone refer to a two-state system in which the output to the patient is either a "warning" state or a "no warning" state. When simple warning systems such as those described in Viglione and Piccone are not sending a warning to the patient ("no warning"), the patient has no idea for how long the "no warning" period will continue, nor does the patient know if the system is receiving signals that are of a known class. In fact, a "warning" could occur at any time, at which point the patient would have to quickly respond, if the patient has a sufficient amount of time to do so. Neither Viglione nor Piccone describe a system that can provide information to patients about when they are not likely to have a seizure (as opposed to when they are likely to have a seizure)—which is an invaluable type of information.

What is needed is a mobile device adapted to alert the patient of their brain state so as to be able to indicate an occurring or impending neurological event, as well as to be able to alert the patient when such an event is unlikely to occur or will not occur. In addition, the alerts should be easy to understand so that a patient can decipher if immediate precautionary action must be taken.

As the device should be adapted to continuously alert the patient of their neurological status, the device should also continuously monitor system components and alert the patient of the status of system components.

SUMMARY OF THE INVENTION

The present invention provides methods, systems, and portable devices that may be used to monitor and provide an indication to the patient of their estimated brain state.

In one aspect, the present invention provides a method of monitoring a patient's brain activity and providing an indication to the patient regarding the patient's brain state within the disease condition. A brain activity signal is sampled from the patient using one or more electrodes that are anywhere in or on the patient. A data signal encoded with data that is indicative of the sampled brain activity signal may then be wirelessly transmitted in substantially real-time from the patient's body to a portable patient advisory device (PAD) that is external to the patient's body. The wireless transmission of the encoded data signal can be performed substantially continuously, periodically, or discontinuously.

The real-time data signal is processed with brain activity algorithm(s) to assess the patient's propensity for a seizure. A first indication may be provided that is indicative of the patient's propensity for the seizure. The first indication can be provided by a plurality of discrete brain state indicators on the PAD, such as light emitting diodes. The plurality of brain state indicators may indicate to patients that they are in a contra-ictal state, an unknown brain state, a pro-ictal state, or an ictal state.

A second indication may be provided to the patient, via the PAD, to indicate the status of at least one component of the system. For example, the second indication may indicate when there is a problem in the wireless transmission of the data signal to the PAD. In some instances the second indication indicates that the external device is out of communication range with a device implanted in the patient's body, or that the substantially real-time data signal is not being received by the external device. Additionally, the second indication may indicate battery strength of the implanted device and/or PAD.

At least one of the first and second indications is delivered by an output assembly in the external device. When the wireless transmission of the encoded data signal is performed substantially continuously, the second output communication can be provided when there is an unexpected discontinuity in the substantially continuous receipt of the data signal in the external device.

In another aspect, the present invention provides a PAD that is configured to provide an output to the patient regarding a patient's brain state within a disease condition. In preferred embodiments the disease condition is epilepsy and the output is indicative of the patient's propensity for a seizure. The PAD may include a housing and a user interface on the housing. The user interface includes a first portion configured to provide system status information to the patient and a second portion that includes at least one brain state indicator that indicates the patient's propensity for a seizure. The brain state indicator may comprise a plurality of discrete brain state indicators that are spaced and separate from the first portion of the user interface. The brain state indicators may differentiate between a contra-ictal state, a pro-ictal state, and an ictal state. Optionally, the brain state indicator may indicate that the patient is in an unknown state or in a state that is not contra-ictal, pro-ictal, or ictal.

A communication assembly housed within the PAD is configured to wirelessly receive the transmitted data signal from the implanted device. A signal processor also housed within the PAD can execute the brain activity algorithm(s) on the transmitted data signal to estimate the subject's brain state. The algorithms can include a seizure detection algorithm, a seizure prediction algorithm, and a safety algorithm (referred to herein collectively as "brain state algorithms").

The brain state indicators, such as a plurality of differently colored light emitting diodes (LED's), corresponding to the estimated brain state are configured to be activated or deactivated to inform the patient of their estimated brain state. In one embodiment the different colored lights include a first colored LED (e.g., green) that indicates that the patient is in a brain state that has a low propensity to having a seizure, a second colored LED (e.g., red) that indicates that the patient is in a brain state that has an increased propensity to having a seizure or that the patient is in an ictal state, and a third colored LED (e.g., yellow, blue, etc.) that indicates that the patient is in an unknown brain state or that the patient is not in a brain state that has a low-propensity or high propensity to having a seizure. In some embodiments, it may be desirable to only include the green light and red light (or their equivalents).

The PAD also includes an output assembly adapted to provide an output when there is a problem with one of the components of the system or if there is a problem with the transmission of the data signal from the implanted communication assembly or receipt of the data signal in the PAD. The output assembly can provide an indication when the PAD is out of communication range with the implanted assembly or when the data is not being received by the PAD.

In other aspects of the invention, the PAD is part of a system for monitoring a patient's brain activity and informing the patient of the patient's brain state. The system includes at least one electrode, which may be placed anywhere in or on the patient, configured to sample brain activity signals from the patient. The electrode is coupled to an implanted communication assembly which is configured to wirelessly transmit, substantially continuously in some embodiments, the encoded data signal to the PAD, which is configured to receive the wireless data signal. The PAD may also include a memory assembly for storing the received data signal.

The communication assembly in the implanted device may also include a therapy assembly that is adapted to automatically initiate therapy to the patient when the patient has an elevated propensity to a seizure. The communication assembly may further include an encryption assembly adapted to encrypt the brain activity signals from the patient before they are transmitted to the PAD. The PAD may optionally comprise a decryption assembly that decrypts the encrypted data signal from the implanted communication assembly, but preferably stores the brain activity signals in an encrypted format.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-2B show examples of patient advisory devices that comprise brain state indicators and system state indicators.

FIGS. 3A-3G illustrate an exemplary patient advisory device in accordance with the present invention.

FIG. 17 illustrates a table that may be used to determine the brain state indication to the patient.

DETAILED DESCRIPTION OF THE INVENTION

Figure 1:
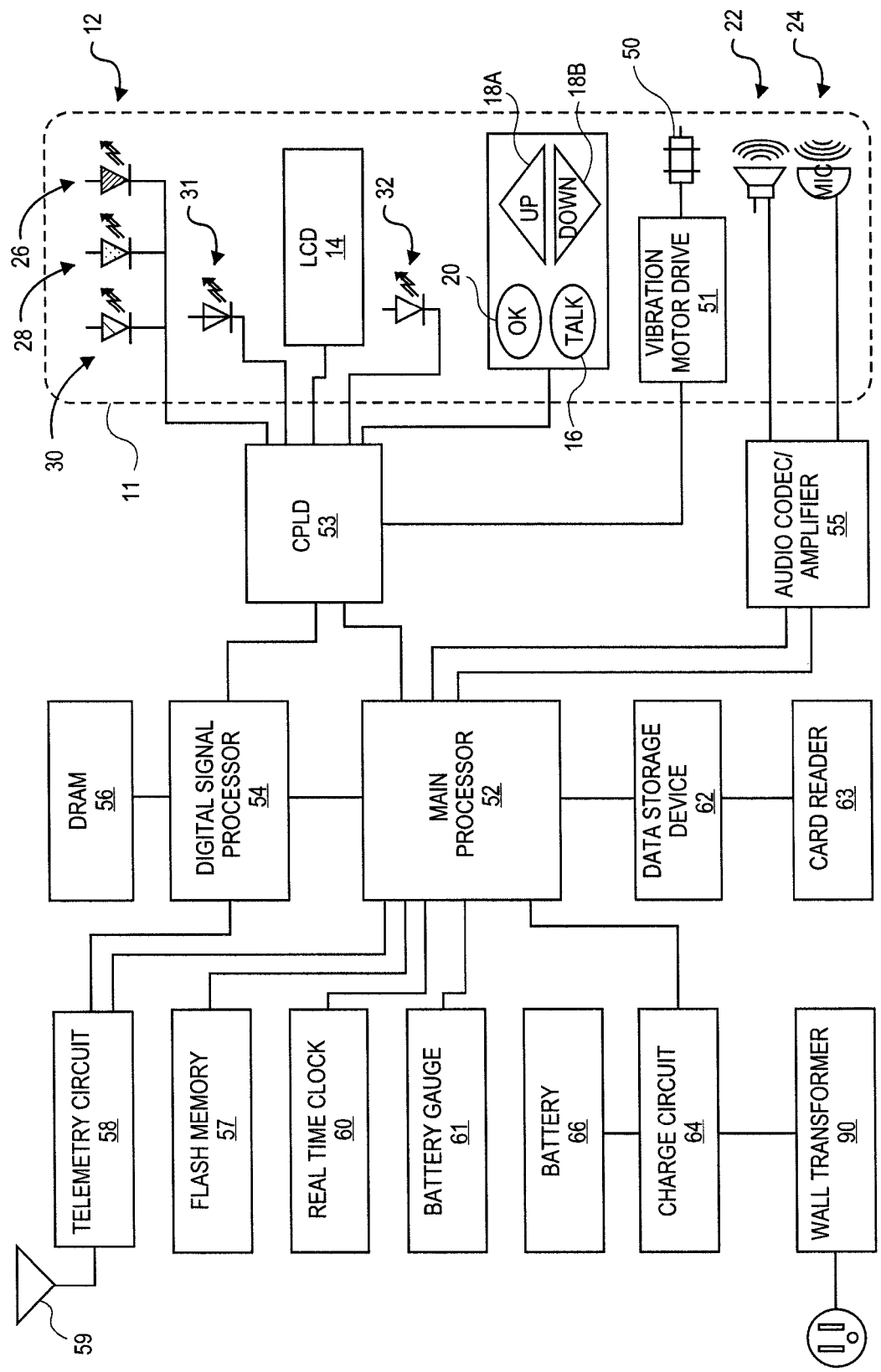
FIG. 1 shows a block diagram of a patient advisory device (PAD).

Certain specific details are set forth in the following description and figures to provide an understanding of various embodiments of the invention. Certain well-known details, associated electronics and medical device components are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

In accordance with the present invention, a patient advisory device ("PAD"), systems that comprise the PAD, and methods of using the PAD are provided. The systems embodied by the present invention may comprise the PAD and an implanted device that is in communication with the PAD. The implanted device may include, or be in communication with, one or more electrodes that sample one or more physiological signals (e.g., brain activity signals) from the patient. The implanted device may be configured to sample and pre-process the sampled signals from the patient and wirelessly communicate a data signal to the PAD. The data signal may be indicative of the physiological signals, but such data signal may also be indicative of the output that should be provided to the patient. At least one of the implanted device and the PAD comprise one or more algorithms (or portions thereof) that are configured to analyze the sampled signals to estimate the patient's brain state. Exemplary systems are described in greater detail below with respect to FIG. 15.

The term "condition" is used herein to generally refer to the patient's underlying disease or disorder—such as epilepsy, depression, Parkinson's disease, headache disorder, etc. The term "state" is used herein to generally refer to calculation results or indices that are reflective a categorical approximation of a point (or group of points) along a single or multi-variable state space continuum. The estimation of the patient's state does not necessarily constitute a complete or comprehensive accounting of the patient's total situation. As used in the context of the present invention, state typically refers to the patient's state within their neurological condition. For example, for a patient suffering from an epilepsy condition, at any point in time the patient may be in one of several different state along the continuum, such as an ictal state (a state in which a neurological event, such as a seizure, is occurring), a pre-ictal state (a neurological state that immediately precedes the ictal state), a pro-ictal state (a state in which the patient has an increased risk of transitioning to the ictal state), an inter-ictal state (a state in between ictal states), a contra-ictal state (a protected state in which the patient has a low risk of transitioning to the ictal state within a calculated or predetermined time period), or the like. A pro-ictal state may transition to either an ictal or inter-ictal state. A pro-ictal state that transitions to an ictal state may also be referred to herein as a "pre-ictal state."

The estimation and characterization of "state" may be based on one or more patient dependent parameters from the a portion of the patient's body, such as electrical signals from the brain, including but not limited to electroencephalogram signals "EEG" and electrocorticogram signals "ECoG" or intracranial EEG (referred to herein collectively as "EEG"), brain temperature, blood flow in the brain, concentration of AEDs in the brain or blood, etc.). While parameters that are extracted from brain-based signals are preferred, the present invention may also extract parameters from other physiological signals of the body, such as the heart rate, respiratory rate, chemical concentrations, etc.

An "event" is used herein to refer to a specific event in the patient's condition. Examples of such events include transition from one state to another state, e.g., an electrographic onset of seizure, end of seizure, or the like. For conditions other than epilepsy, the event could be an onset of a migraine headache, a tremor, or the like.

The occurrence of a seizure may be referred to as a number of different things. For example, when a seizure occurs, the patient is considered to have exited a "pre-ictal state" or "pro-ictal state" and has transitioned into the "ictal state". However, the electrographic onset of the seizure (one event) and/or the clinical onset of the seizure (another event) have also occurred during the transition of states.

A patient's "propensity" for a seizure is a measure of the likelihood of transitioning into the ictal state. The patient's propensity for seizure may be estimated by determining which "state" the patient is currently in. As noted above, the patient is deemed to have an increased propensity for transitioning into the ictal state (e.g., have a seizure) when the patient is determined to be in a pro-ictal state. Likewise, the patient may be deemed to have a low propensity for transitioning into the ictal state for a time period when it is determined that the patient is in a contra-ictal state.

The PAD may be used to provide one or more indications to the patient. The indications generally include a notification to the patient of the patient's substantially real-time brain state (and/or change in brain state), a status of the PAD, and a status of the implanted device (and/or a change in status of the PAD and implanted device). Some examples of the communications regarding the status of the PAD include the PAD's remaining power, hardware status of the PAD, etc., a status of the implanted device including remaining power, function errors, etc., and status of the communication link between the implanted device and the PAD, and the like.

In addition to providing communications to the patient, the PAD may also be adapted to receive inputs from the patient. Such inputs can include recording diary inputs, such as voice audio and/or keypress activity, acknowledgment of alerts from the PAD, adjustment of the types and characteristics of the alerts, such as from tactile alerts to audio alerts, and from soft audio alerts to loud audio alerts, and the like.

In one specific use, the PAD is part of a system used in estimating brain states of patients who are or might be at risk of having a seizure and alerting the patient of the estimated brain state within their epilepsy condition. As such, the brain state indicators may indicate the patient's propensity for having a seizure. While most of the discussion below focuses on measuring EEG signals (monitored extracranial and/or intracranial) of patients for advising the patient of their propensity for epileptic seizures, it should be appreciated that the invention is not limited to measuring EEG signals for epileptic seizures. For example, the invention could also be used in systems that measure one or more of a magnetoencephalograpic (MEG) signal, blood pressure, blood oxygenation via pulse oximetry, temperature of the brain or of portions of the subject, blood flow measurements, ECG/EKG, heart rate signals, respiratory signals, chemical concentrations of neurotransmitters, chemical concentrations of medications, pH in the blood, or other physiological or biochemical parameters of a subject.

Furthermore, the PAD and related devices may be used in monitoring Alzheimer's, migraine headaches, sleep apnea and other sleep disorders, depression, obesity, Parkinson's disease, dementia, attention deficit disorder, eating disorders, and other neurological or psychiatric disorders, cardiac signals (monitoring, for example, ECG signals), respiratory signals (e.g., asthma), glucose levels, or the like.

Exemplary electrode arrays and implantable devices that may be used with the PAD are described in commonly owned U.S. Pat. No. 6,366,813, issued Apr. 2, 2002; U.S. Pat No. 7,209,787, issued Apr. 27, 2007; U.S. patent application Ser. No. 11/766,742, filed Jun. 21, 2007, published as U.S. Patent Publication No. 2008/0027515, abandoned; and U.S. patent application Ser. No. 12/020,507, filed Jan. 25, 2008, published as U.S. Patent Publication No. 2008/0183097, abandoned, the disclosures of which are incorporated by reference herein in their entireties.

Exemplary algorithms that can be used in the analysis of the monitored signals are described in U.S. Pat. No. 6,366, 813, issued Apr. 2, 2002; U.S. Pat. No. 7,209,787, issued Apr. 27, 2007; U.S. patent application Ser. No, 12/020,450, filed Jan. 25, 2008, published as U.S. Patent Publication No. 2008/0183096, pending; and U.S. patent application Ser.

No. 12/035,335, flied Feb. 21, 2008, published as U.S. Patent Publication No. 2008/0208074, abandoned.

FIG. 1 shows a simplified block diagram of one embodiment of a PAD 10 in accordance with embodiments of the present invention. The illustrated PAD 10 shows a user interface 11 that includes a variety of indicators for providing system status and alerts to the patient. User interface 11 may include one or more indicators 12 that indicate the patient's state (e.g., the patient's brain state). In the illustrated embodiment, the patient state indicators 12 may comprise light indicators (for example, LEDs) that comprise one or more (e.g., preferably two or more) discrete outputs that differentiate between a variety of different brain states. In the illustrated embodiment, the patient state indicators 12 include three icons 26, 28, 30 that may be illuminated to indicate the patient's different brain states (described more fully below). In one embodiment, the patient state indicators 12 include a red light 26, a yellow light 28, and a green light 30. In another embodiment, the patient state indicators 12 include a red light 26, a white light 28, and a blue light 30. In some configurations the patient state indicators 12 may be illuminated in accordance with different illumination sequences (e.g., off, solid on, continuous blinking, varied blinking patterns) to indicate different brain states.

The PAD 10 may also include a system state display 14 for communicating information regarding the state of the system to the patient. The system state display 14 may display information regarding the status of the system components and may also display prompts for the patient.

FIGS. 2A-2B illustrate exemplary user interfaces 11 that may be used in accordance with the present invention. For example, as shown in FIG. 2A, the system state display 14 comprises a liquid crystal display ("LCD") and the patient state display 12 comprises three LEDs. The system state display 14 can include multiple indicators in the form of text or icons. The system state display 14 may indicate a variety of information, such as, for example, the battery strength of the implanted device (implanted battery strength icon 34), the battery strength of the PAD (PAD battery strength icon 36), the strength of the wireless communication signal between the implanted device and the PAD 10 (signal strength indicator 38), status of a data storage device (storage status indicator 37), and audio status of the PAD (alert mode indicator 42). The alert mode indicator 42 may include multiple segments that can be separately activated to indicate an output volume level of the PAD and/or activation of a vibration output of the PAD, as is similarly used in mobile telephones and pager devices. The system state display 14 may be graphically divided into separate sections for indicating status information regarding the various components of the system (e.g., implanted device status section 13 and PAD status section 15).

If desired, a separate "alert" or "information" light 32 may be used to provide notice to the patient of some event. It may be desirable for the alert light 32 to be separate from the patient state indicators 12 so as to minimize the potential confusion by the patient. In other embodiments, the alert light 32 may be omitted and the PAD 10 may communicate alert information to the patient by using one or more of the patient state indicators 12 (e.g., by flashing one or more of the brain state indicators 26, 28, 30). In the embodiment shown in FIG. 2A, the system state display 14 includes an alert light 32 comprising an icon shaped like a wrench and illuminated by an LED. The alert light 32 is used in this embodiment to indicate that a failure has occurred with either the PAD or implanted device hardware. The patient may be instructed to attempt to clear this alert by power cycling the PAD 10. If the alert light 32 remains persistent, the patient is instructed to return the PAD 10 for repair. If a failure occurs in the implanted device, the implanted device can send a message with a description of the failure to the PAD 10. This failure can be stored on the data storage device 62 for analysis by a technician.

The output of the system state display 14 is preferably continuous, but in some embodiments may appear only upon the occurrence of an event or change of the system status and/or the LCD may enter a sleep mode until the patient activates a user input.

The embodiment shown in FIG. 2B includes additional indicators that may be used. For example, the system state display 14 in FIG. 2B also includes a time display 40, and a character display 44 for providing visual text alerts to the patient—such as an estimated time to seizure or an estimated "safe" time. In yet other embodiments, the LCD 14 may also indicate the amount of free memory remaining on the internal storage device of the PAD.

In the embodiments shown in FIG. 2A-2B, the patient state display 12 is provided using different color LEDs and the system state display 14 is provided using an LCD. The use of two different display types for the patient state display 12 and the system state display 14 may be helpful to improve communication to the patient. For example, the more prominent or easily viewable display type may be used for the patient state display 12, in order to urgently draw the patient's attention to the brain state information. At the same time, more detailed system state information may be provided using less prominent display technologies, e.g., an LCD. In other embodiments, both the patient state display 14 and the system state display 14 may be provided by a single LCD screen or other graphical display device. Accordingly, the LCD screen may be used to display system status outputs and to also display the algorithm output (e.g., brain state indication), and the separate LEDs may be omitted. In the illustrated embodiments, the system state display 14 comprises a common-plane-type LCD, which may be desirable for visual clarity and power conservation. In other embodiments, more sophisticated display technology may be used to display more complex graphical images.

Referring again to FIG. 1, PAD 10 may also include a speaker 22 and an audio codec and amplifier module 55 for generating audio outputs to the patient (e.g., beeps, tones, music, recorded voice alerts, etc.). These audio outputs may be used to indicate brain state or system status to the patient. User interface 11 may also include a vibratory output device 50 and a vibration motor drive 51 to provide a tactile alert to the patient, which may be used separately from or in conjunction with the visual and audio outputs provided to the patient. The vibratory output device 50 is generally disposed within PAD 10, and is described in more detail below. Depending on the desired configuration any of the aforementioned outputs may be combined to provide information to the patient.

The PAD 10 preferably comprises one or more patient inputs that allow the patient to provide inputs to the PAD. In the illustrated embodiment, the inputs comprise one or more physical inputs (e.g., buttons 16, 18a-18b, 20) and an audio input (in the form of a microphone 24 and a pre-amp circuit).

Similar to conventional cellular phones, the inputs 16, 18a-18b, 20 may be used to toggle between the different types of outputs provided by the PAD. For example, the patient can use directional buttons 18a-18b to select from several alert modes, such as a vibration alert rather than audio alerts (if, for example, a patient is in a movie theater). Or the patient may wish to turn the alerts off altogether (if, for example, the patient is going to sleep). In addition to choosing the type of alert, the patient can choose the characteristics of the type of alert. For example, the patient can set the audio tone alerts to a low volume, medium volume, or to a high volume.

Some embodiments of the PAD 10 will allow for recording audio, such as voice data. A dedicated voice recording user input 16 may be activated to allow for voice recording. After the user input 16 is pressed, a recording notice light 31 may be illuminated when the PAD 10 is actively recording audio with the microphone 24 in order to provide the user with a visual feedback confirming recording. In preferred embodiments, the voice recording may be used as an audio patient seizure diary. Such a diary may be used by the patient to contemporaneously record when a seizure has occurred, when an aura or prodrome has occurred, when a medication has been taken, to record patient's sleep state, stress level, etc. Such voice recordings may be time stamped and stored in a removable data storage device 62 of the PAD and may be transferred along with recorded EEG signals to the physician's computer. Such voice recordings may thereafter be overlaid over the EEG signals and used to interpret the patient's EEG signals and improve the training of the patient's customized algorithm, if desired.

In some embodiments, the audio recording using the microphone 24 may be initiated automatically by the PAD 10 in response to a predetermined event. For example, the audio recording may automatically begin after a certain brain state has been detected (e.g., after an ictal state is detected, after a pre-ictal state is detected, and/or after a pro-ictal state is detected). It may be helpful for physicians to later review the audio recording corresponding to the time period during which a seizure is believed to have occurred. In some embodiments, for privacy reasons, it may be desirable to permit the patient or physician to selectively enable or disable the automatic audio recording.

The one or more inputs may also be used to acknowledge system status alerts and/or brain state alerts. For example, if the PAD 10 provides an output that indicates a change in brain state, one or more of the LEDs 12 may blink, the vibratory output may be produced, and/or an audio alert may be generated. In order to ensure that the patient is made aware of the alert, it may be desirable for the alert to continue until the patient acknowledges the alert using one of the user inputs. For example, in order to turn off the audio alert, turn off the vibratory alert, and/or to stop the LEDs from blinking, the patient may be required to acknowledge receiving the alert by actuating one of the user inputs (e.g., pushing acknowledgement button 20).

While the PAD 10 is shown having inputs 16, 18a-18b, 20, any number of inputs may be provided on the PAD 10. For example, in one alternate embodiment, the PAD 10 may comprise only two input buttons. The first input button may be a universal button that may be used to scroll through output mode options. A second input button may be dedicated to voice recording. When an alert is generated by the PAD 10, either of the two buttons may be used to acknowledge and deactivate the alert. In other embodiments, however, there may be a dedicated user input for acknowledging the alerts.

As shown in FIG. 1, the PAD 10 may comprise a main processor 52 and a complex programmable logic device (CPLD) 53 that control much of the functionality of the PAD 10. In the illustrated configuration, the main processor 52 and/or CPLD 53 control the outputs displayed on the system state display 14, generates the control signals delivered to the vibration motor drive 51 and audio codec and amplifier module 55, and receives and processes the signals from buttons 16, 18a-18b, 20, microphone 24, and a real-time clock 60. The real-time clock 60 may generate the timing signals that are used with the various components of the system.

The main processor 52 may also manage a data storage device 62, provide redundancy for a digital signal processor 54 ("DSP"), and manage the telemetry circuit 58 and a charge circuit 64 for a power source, such as a battery 66. A separate non-volatile memory module such as flash memory 57 may be used, if desired, such as when using a main processor 52 that does not include onboard non-volatile memory.

While main processor 52 is illustrated as a single processor, the main processor 52 may comprise a plurality of separate microprocessors, application specific integrated circuits (ASIC), or the like. Furthermore, one or more of the microprocessors 52 may include multiple cores for concurrently processing a plurality of data streams.

The CPLD 53 may act as a watchdog to the main processor 52 and the DSP 54 and may flash the system state display 14 and patient state indicators 12 if an error is detected in the DSP 54 or main processor 52. Finally, the CPLD 53 controls the reset lines for the main microprocessor 52 and DSP 54.

A telemetry circuit 58 and antenna 59 may be disposed in the PAD 10 to facilitate one-way or two-way data communication with the implanted device. The telemetry circuit 58 may be an off the shelf circuit or a custom manufactured circuit. Data signals received from the implanted device by the telemetry circuit 58 may thereafter be transmitted to at least one of the DSP 54 and the main processor 52 for further processing.

The DSP 54 and DRAM 56 receive the incoming data stream from the telemetry circuit 58 and/or the incoming data stream from the main processor 52. The brain state algorithms are used to process the data (for example, EEG data) and estimate the patient's brain state, and are preferably executed by the DSP 54 in the PAD 10. In other embodiments, however, the brain state algorithms may be implemented in the implanted device, and the DSP 54 (or other processor) may be used to generate the communication to the patient based on the data signal from the algorithms in the implanted device.

The main processor 52 is also in communication with the removable data storage device 62. The data storage device 62 preferably has at least about 7 GB of memory so as to be able to store EEG data from about 8 channels at a sampling rate of between about 200 Hz and about 1000 Hz. With such parameters, it is estimated that the 7 GB of memory will be able to store at least about 1 week of patient data. Of course, as the parameters (e.g., number of channels, sampling rate, etc.) of the data monitoring change, so will the length of recording that may be achieved by the data storage device 62. Furthermore, as memory technology improves the availability capacity in small form factor storage devices, it is contemplated that larger data storage devices may be used (e.g., 10 GB or more, 20 GB or more, 50 GB or more, 100 GB or more, etc.). Examples of some useful types of data storage device include a removable secure digital card or a USB flash key, preferably with a secure data format.

"Patient data" may include one or more of raw analog or digital EEG signals, compressed and/or encrypted EEG signals or other physiological signals, extracted features from the signals, classification outputs from the algorithms, etc. The data storage device 62 can be removed when full and read by a card reader 63 associated with the patient's computer and/or the physician's computer. If the data storage device 62 is full and additional patient data is received, the PAD 10 may be configured to either: (1) overwrite the earliest stored data with the most recent data; or (2) process the subsequent data using the DSP 54 to estimate the patient's brain state and display this information using the patient state indicators 12 without storing the data on the data storage device 62. While preferred embodiments of the data storage device 62 are removable, other embodiments of the data storage device may comprise a non-removable memory, such as FLASH memory, a hard drive, a microdrive, or other conventional or proprietary memory technology. Data retrieval from such non-removable data storage devices 62 may be carried out using conventional wired or wireless data transfer methods.

The power source used by the PAD 10 may comprise any type of conventional or proprietary power source, such as a non-rechargeable or rechargeable battery 66. If a rechargeable battery is used, the battery may be a medical grade battery of chemistries such as a lithium polymer (LiPo), lithium ion (Li-Ion), or the like. The rechargeable battery 66 will be used to provide the power to the various components of the PAD 10 through a power bus (not shown). The main processor 52 may be configured to control the charge circuit 64 that controls recharging of the battery 66. A battery gauge circuit 61 may be used to detect the available capacity of the battery 66. In order to recharge the PAD 10, the PAD 10 may be connected to a power source via a power jack located behind power jack door 21.

In addition to being able to communicate with the implanted device, the PAD 10 may have the ability to communicate wirelessly with a remote device—such as a server, database, physician's computer, manufacturer's computer, or a caregiver advisory device (CAD). In the exemplary embodiment, the PAD may comprise a communication assembly (not shown) in communication with the main processor 52 that facilitates the wireless communication with the remote device. The communication assembly may be a conventional component that is able to access a wireless cellular network, pager network, wifi network, or the like, so as to be able to communicate with the remote device.

In one particular embodiment, the PAD 10 is able to deliver a signal through the communication assembly that is received by the CAD so as to inform the caregiver of the patient's brain state or change in brain state. The CAD would allow the caregiver to be away from the patient (and give the patient independence), while still allowing the caregiver to monitor the subject's brain state and propensity for seizure. Thus, if the patient's brain state indicates a high propensity for a seizure or the occurrence of a seizure, the caregiver would be notified via the CAD, and the caregiver could facilitate an appropriate treatment to the patient (e.g., small dosage of an antiepileptic drug, make the patient safe, etc.). A signal may be provided to the caregiver only if the patient has a high propensity for a seizure or if a seizure is detected, or it may provide the same indications that are provided to the patient.

In other embodiments, the communication assembly could be used to facilitate either real-time or non-real time data transfer to the remote server or database. If there is real time transfer of data, such a configuration could allow for remote monitoring of the patient's brain state and/or EEG signals. Non-real time transfer of data could expedite transfer and analysis of the patient's recorded EEG data, extracted features, or the like. Thus, instead of waiting to upload the brain activity data from the patient's data storage device, when the patient visits their physician, the physician may have already had the opportunity to review and analyze the patient's transferred brain activity data prior to the patient's visit.

The PAD 10 may be configured to perform a hardware/software self test to detect system errors such as power failures, software failures, impedance change, battery health of the implanted device, battery health of the PAD 10, internal clock and voltage reference, hardware (processors, memory, and firmware) checks, or the like. The self test may be performed periodically, upon initial startup, upon a system reset, or some combination thereof. The system preferably runs a self-test on the PAD, implanted device, electrode array and the communication links. The PAD may emit a tone and/or display information on the LCD at the initiation of the self-test(s). If the PAD, implanted device, electrode array and/or communication link pass the self-test, the patient may be notified with an alert indicating the respective devices passed the self-test. If any of the components do not pass the self-test, the patient can be alerted with an output that indicates which component did not pass (for example, an icon on the LCD representing the component which did not pass the test flashes). There may also be an audio alert, such as a voice alert, that one or some of the devices failed the test. The PAD may also indicate these failures with alert light 32. The system may then wait for input from the patient to acknowledge the system failure(s) by depressing a button on the PAD (such as the acknowledgement button 20), which indicates the user is aware of the alert. Additionally or alternatively, there may be a text display on the LCD notifying the patient to contact the manufacturer or physician to receive further instructions.

The PAD may be configured to be toggled between two or more different modes of operation. In one embodiment, the physician may toggle the PAD between three different modes of operations. Of course, it should be appreciated that the PAD may have as little as one mode of operation, or more than three different modes of operations.

In one example, a first mode of operation of the PAD may be merely data collection, in which data signals from the implanted device are stored in the data storage device 62 of the PAD 10. In such a mode, the user interface 11 may be modified to only provide system status indications to the patient via the system state display 14, and the patient state indicators 12 may be temporarily disabled.

In a second mode of operation, after the brain state algorithms have been trained on the patient's data that was collected during the first mode of operation, the brain state algorithms may be implemented to process substantially real-time data signals and the patient state indicators 12 may be enabled so as to inform the patient of their substantially real-time brain state.

In a third mode of operation, it may be desirable to only receive and process the data signals from the implanted device, but no longer store the substantially continuous data signals in a memory of the PAD. For example, if the brain state algorithms are performing as desired, the brain data signals from the implanted device will not have to be stored and analyzed. Consequently, the patient would not have to periodically replace the data card as frequently. However, it may still be desirable to store the data signals that immediately precede and follow any detected seizure. Consequently, in the third mode such seizure data signals may optionally be stored.

As noted above, the PAD 10 may implement one or more brain state algorithms. In one embodiment, the brain state algorithms embodied in the present invention will generally characterize the patient's brain state into one of a plurality of brain states, e.g., "Safe or Low Propensity," "Unknown," "Prediction or Elevated Propensity," or "Detection." It is intended that these are meant to be exemplary categories and are in no way to be limiting and additional brain states or fewer brain state indicators may be provided. There may be different types of algorithms which are configured to characterize the brain state into more or less discrete states.

The "Safe" state can be defined to mean that brain activity indicates that the patient is in a contra-ictal state and has a low susceptibility to transition to an ictal state for an upcoming period of time (for example, 60 minutes to 90 minutes). This is considered positive information and no user lifestyle action is required. A "prediction" state can be defined to mean that the algorithm(s) in the PAD have determined that the patient is in a pro-ictal state and has an elevated propensity for a seizure (possibly within a specified time period). A "detection" state can be defined to mean that brain activity indicates that the patient has already transitioned into an ictal state (e.g., occurrence of an electrographic seizure) or that there is an imminent clinical seizure. User actions should be focused on safety and comfort. An "unknown" state can be defined to mean that the current type of brain activity being monitored does not fit within the known boundaries of the algorithms and/or that the brain activity does not fit within the contra-ictal state, pro-ictal state, or ictal state. Therefore no evaluation can be reliably made. "Unknown" can also indicate there has been a change in the status of the brain activity and while the patient does not have an elevated propensity and no seizure has been detected, it is not possible to reliably inform the patient that he or she is substantially safe from transitioning into an ictal state for a period of time. This state is considered cautionary and requires some cautionary action such as limiting exposure to risk. "Unknown" may also be used to indicate that there has been some sort of system failure preventing reliable characterization of brain state. This may occur, for example, if there is a communication failure between the PAD and the implanted device, thereby preventing the PAD from receiving a sufficient amount of data signals to processing. Such a communication failure may occur intentionally, e.g., if the user manually powers down the PAD (such as when flying on an aircraft), or accidentally, e.g., if the PAD travels beyond the transmission range of the implanted device. The different types of "unknown" may have separate brain state indicators, or they may be combined into a single brain state indicator, or the user interface may not provide the "unknown" state to the patient at all.

The form of the brain state indicators on the PAD may take a variety of different forms and provide a variety of different types of information to the patient. In one embodiment, the patient brain states can be divided into discrete states. For example, the patient can be notified of brain states that are either determined to be "safe or low propensity," "unknown," "prediction or elevated propensity" and "detection." The alerts can also be set up to be discrete outputs, for example, four separate LED lights. In some embodiments, it may be desirable to use a single output to indicate both the "prediction or elevated propensity" and "detection" states, since the recommended patient response may be the same in either case. For example, the patient state indicators 12 may include a red light 26 to indicate both the "prediction or elevated propensity" and "detection" states, a yellow light 28 to indicate the "unknown" state, and a green light 30 to indicate the "safe or low propensity" state. The lights 26, 28, 30 may be used to illuminate different icons, which may be helpful to assist in providing alerts to colorblind patients.

In some embodiments, different illumination sequences for the patient state indicators 12 may be used to communicate with the patient. In one embodiment, the red light 26 may be maintained in an illuminated state to indicate the "prediction or elevated propensity" state and the red light 26 may be flashed to indicate the "detection" state.

In other embodiments, however, it may be desirable to output the patient's estimated brain state as a point on a continuum (e.g., like the mercury in a thermometer) and possibly have discrete indicators marking the boundaries between "low propensity," "unknown," "high propensity," and "detection." In this way, more detailed information on the patient's brain state could be provided to the patient as biofeedback, as they could watch their brain state over an infinite number of states and not simply be notified if they are in one of four discrete states. Such biofeedback may also allow the patient to affect their brain state (e.g., through relaxation techniques, etc.) and move their propensity from elevated to low. While the preferred embodiments of the present invention provide four states (safe, unknown, prediction, detection), it should be appreciated that the present invention is not limited to such a combination of states, and that the PAD may have fewer (e.g., safe and prediction) or additional states that are estimated and thereafter communicated to the patient.

In some embodiments, the PAD may be configured to respond to failures (e.g., communication failures, hardware failures, software failures, etc.) in various ways. In some embodiments, the implanted device may only be provided with a small amount of memory in order to reduce size, complexity, power consumption, or cost of the implanted device. Accordingly, if there is a communication failure between the implanted device and the PAD, it may not be possible for the implanted device to resend the data if the data has already been overwritten by new data. In this case, the PAD may be configured to automatically switch to a higher level of alert after a failure is detected. Thus, if a communication failure is detected while the PAD is showing a green light (e.g., a brain state that has a low propensity to having a seizure), the PAD will automatically switch to a white light indicating that the patient is in an unknown brain state or that the patient is not in a brain state that has a low-propensity or high propensity to having a seizure. Similarly, if a communication failure is detected while the PAD is showing a white light, the PAD will automatically switch to a red light (e.g., indicating that the patient is in a brain state that has an increased propensity to having a seizure). If the failure is detected while the PAD is showing a red light, the PAD may be configured to maintain the red light for an extended period of time.

Figure 3A:
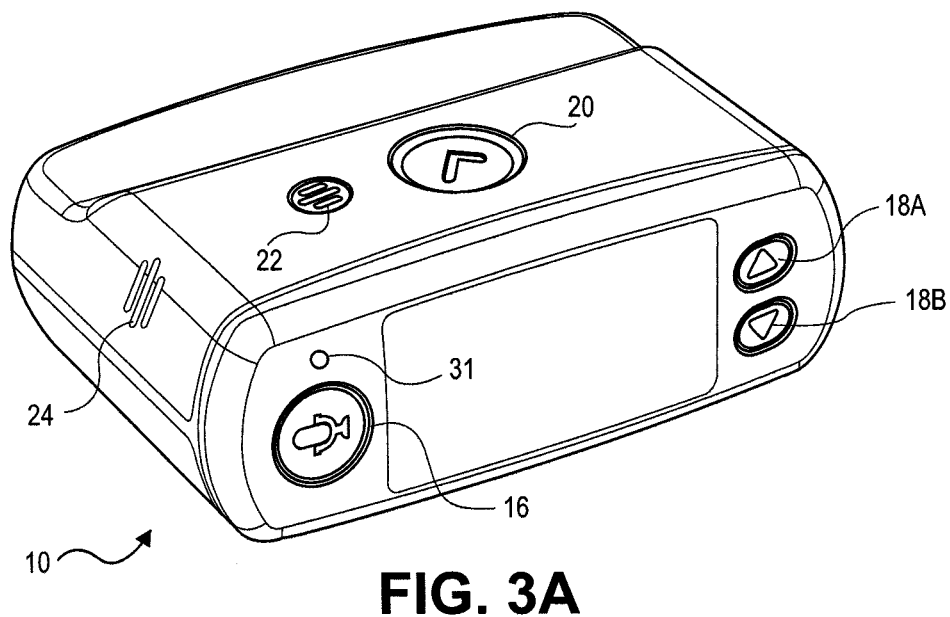
Figure 3B:
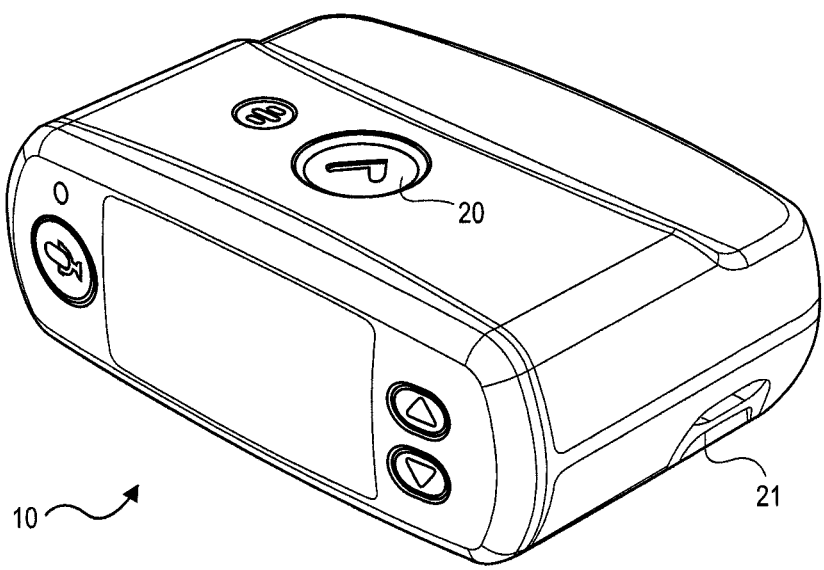
Figure 3C:
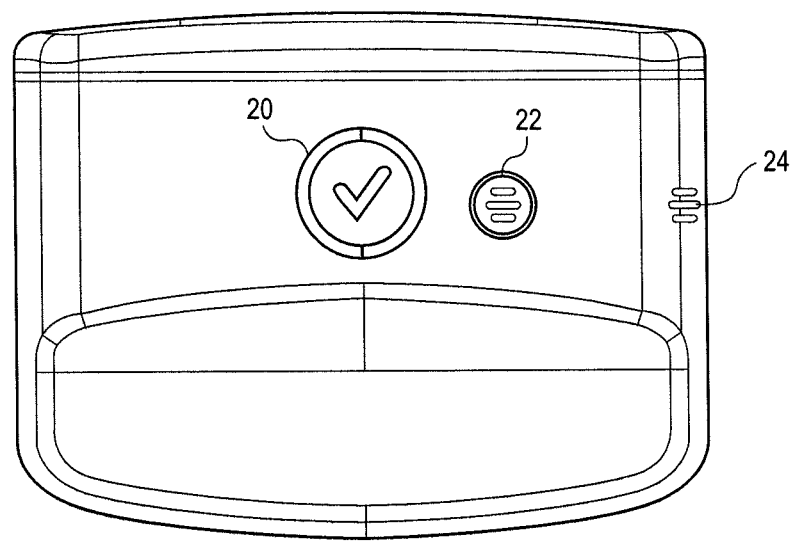
Figure 3D:
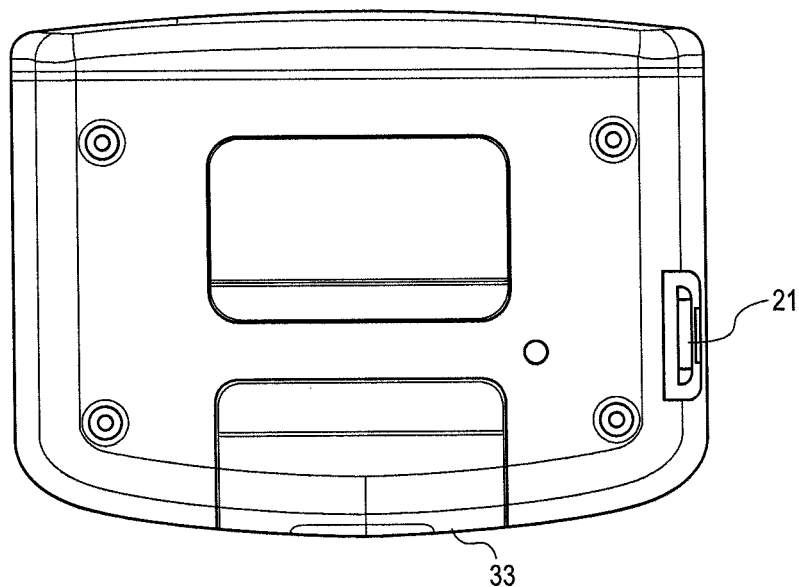

FIGS. 2A and 3A-3G illustrate an exemplary PAD 10 in accordance with the present invention. FIGS. 3A-3B are two isometric top views of the PAD 10, FIG. 3C is a front view, FIG. 3D is a back view, FIG. 3E is a first side view and FIG. 3F is a second side view, and FIG. 3G is a bottom view.

FIGS. 18A-18$S_g$ illustrate a number of different PAD designs and combinations of brain state indicators, system status indicators, and patient inputs, in accordance with other embodiments. While FIGS. 2A-2B, 3A-3G, and 18A-18$S_g$ illustrate a number of preferred embodiments, it should be appreciated that elements of the illustrated embodiments may mix and match with each other, and the present invention is not limited to the illustrated combination of elements. When these devices are used by patients who suffer from seizures, it is desirable for the PAD to be sufficiently rugged so as to withstand impacts when the patient falls, and sufficiently smooth so as to minimize the likelihood of injury caused to the patient if the patient were to fall on top of the PAD.

The PAD 10 will preferably comprise visual indicators, such as LEDs, notifying the patient of the determined brain state. As described above, in one preferred embodiment, the visual indicators for the brain state alerts will comprise a green light, a yellow light, and a red light. The green light will be illuminated when the PAD determines that the brain state is in a "safe" or "low propensity to seizure" state. The yellow light will be illuminated when the patient is in an "unknown" state. The PAD will emit a solid red light when the patient is in the "prediction" or "high propensity" state. The PAD will emit a blinking red light when the patient is in the "detection" state. The light colors or number of light indicators are not intended to be limiting. Any color may be used in order to provide the desired user communication, such as, e.g., a white light in place of the yellow light and a blue light in place of the green light. It may be desirable to include additional lights or colors (e.g., orange) to further delineate the patient's estimated condition. In yet other embodiments, it may be desirable to display only a green light and red light.

The lights may be physical lights (e.g., LEDS), colored icons on the LCD, or other conventional components for generating a visual indication to the patient. As will be described below, the brain state indicators 12 themselves may be positioned anywhere on the housing of the PAD.

FIGS. 2A, 3A-3G, 18B, 18C and 18N illustrate configurations of the PAD which include discrete brain state indicators that are separated from the system state indicators. The discrete brain state indicators have separate indicators for each of the different estimated brain states.

FIG. 2B illustrates an embodiment which includes three brain state indicators 12 that are positioned along an upper left portion of the top surface of the PAD 10. The brain state indicators 12 (green, yellow, red) are separated from each other. Furthermore, to increase differentiation between the system status information, the brain state indicators 12 are physically separated from the LCD 14 and the alert light 32.

Figure 18B:
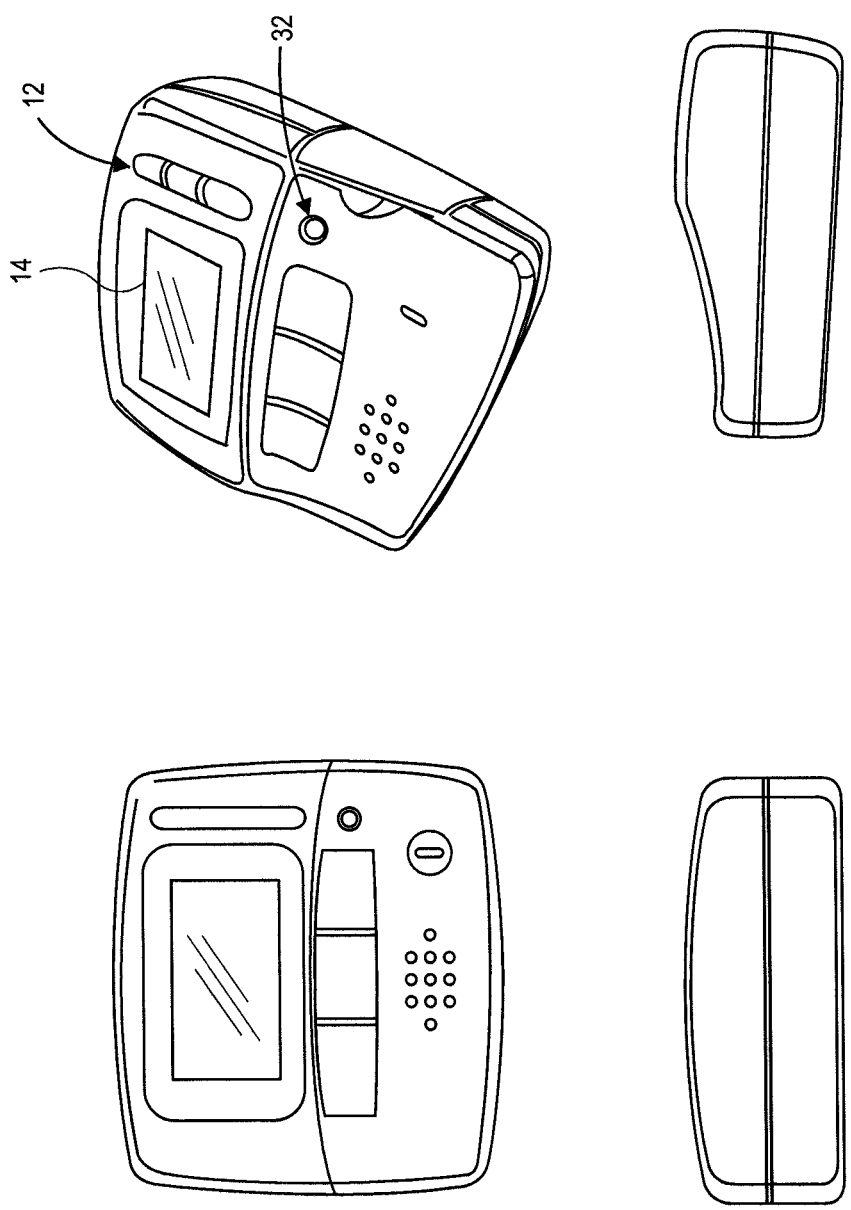
FIGS. 18A-18R and $18S_a$-$18S_a$ are examples of various designs of the patient advisory device.

FIG. 18B illustrates an embodiment in which the brain state indicators 12 are positioned in a vertical orientation adjacent the LCD 14. To reduce potential confusion, the brain state indicators are of a different shape and are separated from the alert light 32. In the embodiment of FIG. 18B, the brain state indicators are in a vertical orientation—similar to a stop light—in which red is on top, yellow in the middle, and green in the bottom.

Figure 18C:
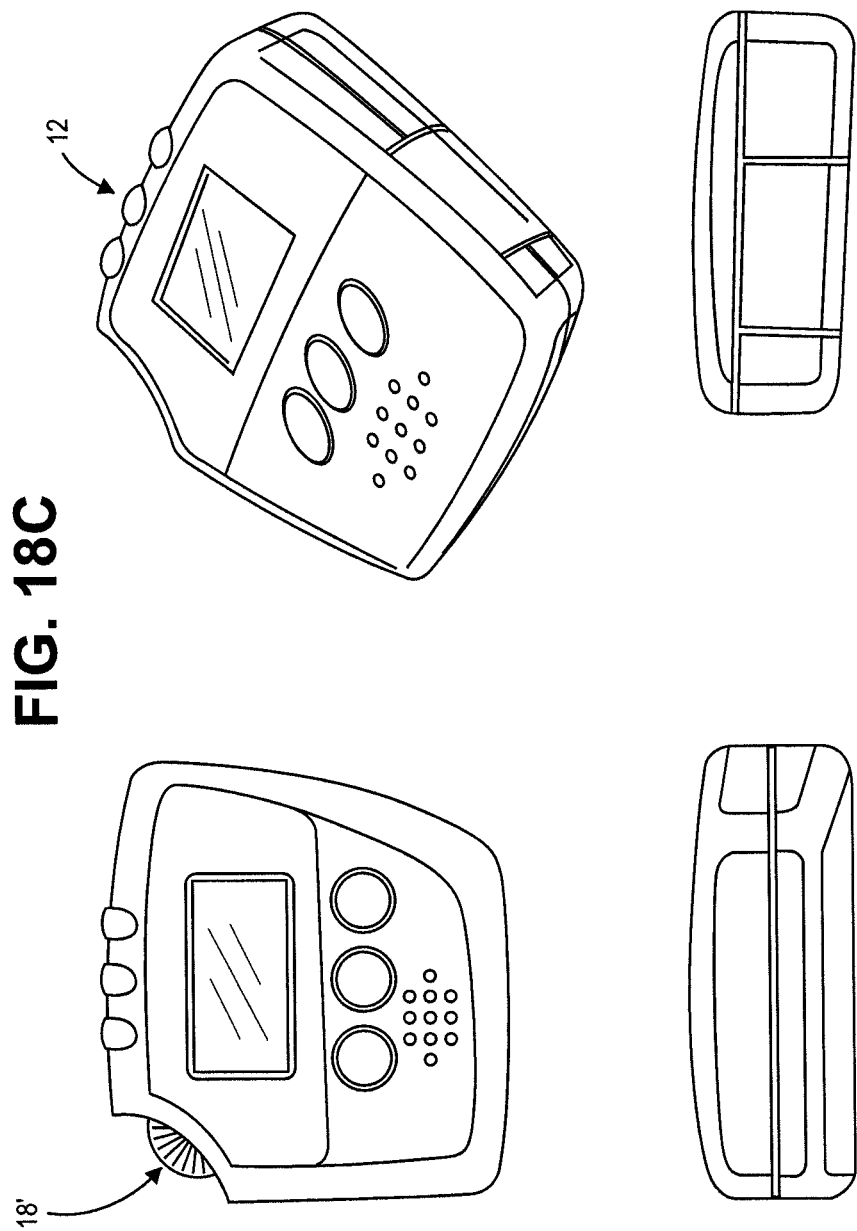
Figure 18K:
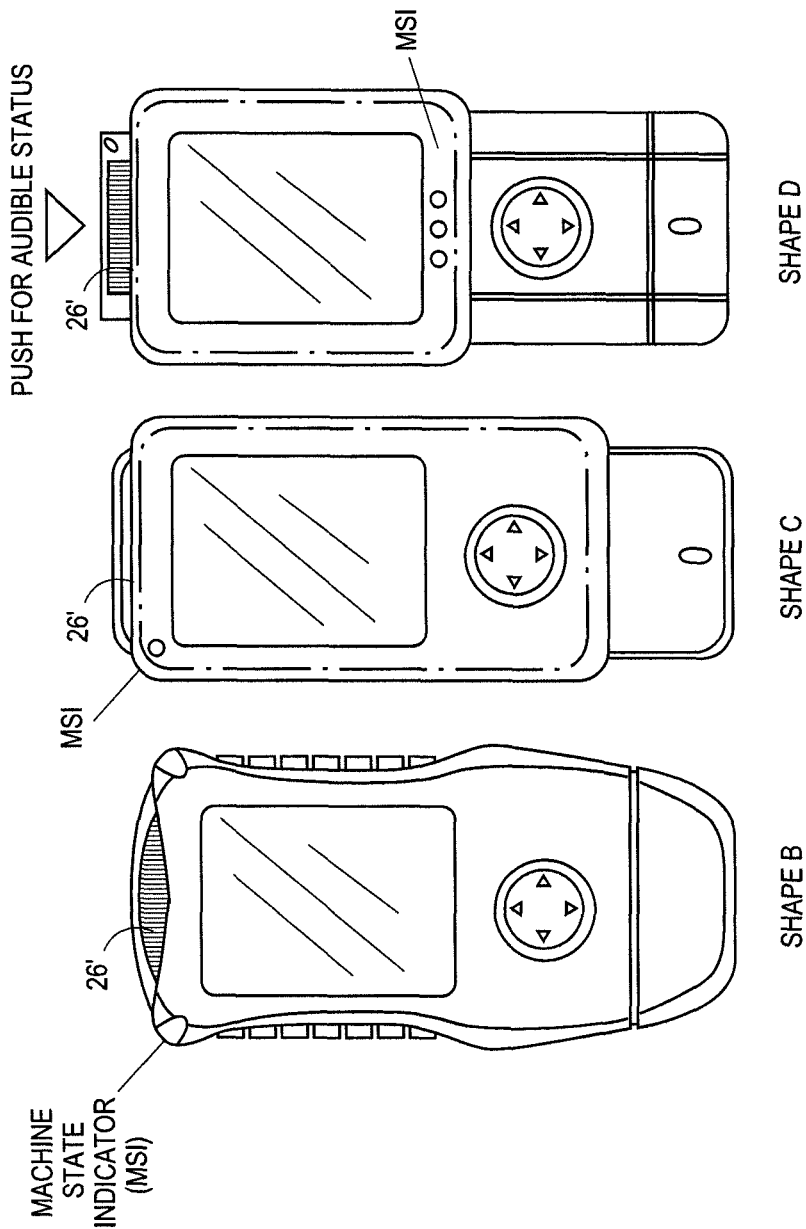
Figure 18L:
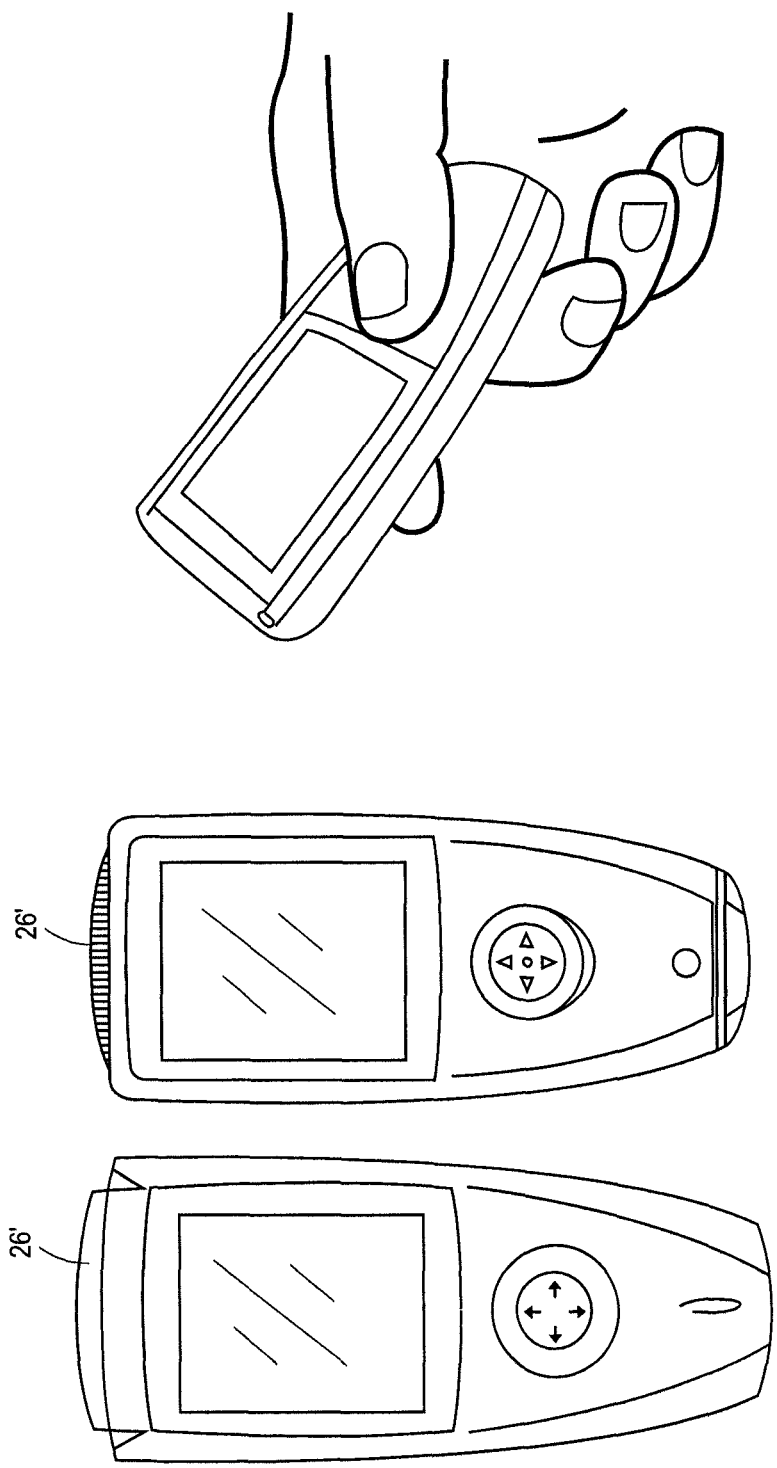

The brain state indicators 12 of FIGS. 18C and 18N are positioned at a junction between a front face and a top face of the PAD 10. Such a configuration is beneficial for patients who might attach the PAD to a belt clip, or the like. Such a configuration would allow the patient to view the brain state indicators 12 from a different number of vantage points.

Because some patients may not be able to sufficiently distinguish between the red, yellow, and green colors, the configuration of the embodiments of FIGS. 3A-3G, 18B, 18C, and 18N provide "positional indicators." As such, the patient will be able to know their brain state merely by seeing which brain state indicator is lit. For example, for the embodiment of FIGS. 3A-3G, the patient will know that the left most light 30 in the string of LEDs means "safe" or "low propensity," the middle light 28 in the LEDs means "unknown", the right most light 26 of the LEDs means "prediction" or "high propensity" and a blinking right-most light 26 of the LEDs means "detection."

In some configurations it may be desirable to provide iconic indicators having unique shapes for the different brain state indicators. In the embodiment shown in FIGS. 3A-3G, the left light 30 is an inverted triangle, the middle light 28 is a circle, and the right light 26 is upright triangle. FIGS. 18P and 18S$_b$ illustrate other embodiments. The circle, rectangle, and triangle (along with the different colored lights) may be used to indicate to the patient their brain state. If the different shapes are used, it may not be necessary to use different colored lights to indicate the different brain states. The use of positional indicators and/or iconic indicators may be helpful for patients who are visually impaired, e.g., colorblind.

In various embodiments, different mechanisms for user inputs may be used. In FIGS. 18C, 18M, the PAD 10 further includes a thumbwheel control input 18', which may be provided in place of the directional buttons 18a-18b shown in FIGS. 3A-3G. In FIG. 18G, three control options are provided: thumbwheel control input 18', four side buttons 19a-19d, and three front buttons 19e-19g.

As shown in FIGS. 18A, 18D, 18E, 18F, 18G, 18H, 18I, 18J, 18K, 18L, 18M, 18O, 18Q and 18R, the brain state indicator 12 includes a single panel 26' that can be illuminated in different ways to indicate the patient's estimated brain state. For example, a light pipe and multiple lights of different colors may be used to illuminate the panel 26' in different colors to indicate the brain state when the patient is in that particular brain state. In some embodiments, such as in FIG. 18A, the panel 26' may be integrated into a button that may be pressed by a user to provide an input to the PAD 10 (e.g., to acknowledge an alert).

FIGS. 18A, 18F, 18G, 18H, 18I, 18J, 18K, 18L, 18Q and 18R show embodiments which include a single brain state indicator panel 26' along a junction of a top surface and front surface of the PAD 10. As noted earlier, such a configuration allows for viewing of the patient's brain state by looking either at a top surface or a front surface of the PAD 10.

FIGS. 18G, 18M, and 18O have a brain state indicator panel 26' only on the front surface of the PAD.

In FIG. 18E, the brain state indicator 12 comprises two panels 26', 28', which are illuminated simultaneously using the same color to indicate the patient's estimated brain state. The embodiment of FIG. 18E has the advantage of having brain state indicators along three surfaces: a top surface, front surface, and bottom surface, so as to allow the patient to view their brain state from different angles.

In FIG. 18D, the single panel 26' comprises a panel 26' that extends around a portion or the entire perimeter of the front face of the PAD 10. This embodiment would allow the patient to quickly determine their brain state from almost any viewing angle.

FIGS. 18S$_a$-18S$_g$ illustrate a variety of different views of another embodiment of the PAD. FIGS. 18S$_a$ and 18S$_b$ are two alternative top plan views of the PAD. FIGS. 18S$_c$ and 18S$_e$ are opposing side views. FIG. 18S$_d$ is a bottom view. FIG. 18S$_f$ is a top view. FIG. 18S$_g$ is a rear view. The illustrated embodiment of FIG. 18S is a pager-style PAD that may be carried on a clip (not shown) that may be used to couple the PAD to the patient's belt or bag. The dimensions of this embodiment of the PAD may be, e.g., 1.00"×2.50"× 3.50", but may be larger or smaller as desired.

Similar to the other embodiments, the PAD of FIGS. 18S$_a$-18S$_g$ comprise a plurality of user inputs 16, 18, 20, brain state indicators 12 and outputs that indicate a state of the system (e.g., LCD 14). As shown in FIG. 18S$_b$, the LCD may comprise a plurality of different icons on the LCD 14 to indicate the state of the system. For example, the illustrated embodiment includes a PAD battery indicator 36, implanted device battery indicator 34, telemetry signal strength indicator 38, volume indicator 42, and a memory card status indicator 107. To differentiate between the implanted device system state and PAD system state, it may be desirable to provide a physical separation 35 between the icons. The physical separation element 35 could be a physical barrier that overlays the LCD, two separate LCDs that are spaced from each other, or simply a discernable separation between icons on the LCD.

The LCD 14 and brain state indicators 12 may be viewable by the patient when it is attached to the patient's belt. As such, the patient need only glance down onto the top surface of the PAD when an audible or tactile indication is provided that indicates a patient's brain state or change thereof.

In the embodiment of FIG. 18$S_a$, the brain state indicator lights 26, 28, 30 may be positioned along the junction of the top surface and front surface so as to be viewable from multiple angles. Therefore, the patient may be able to quickly see the lights 26, 28, 30 when looking at two different sides of the PAD. In another embodiment shown in FIG. 18$S_b$, either in addition to the brain state indicator lights 26, 28, 30 on the front surface (FIG. 18$S_f$) or as an alternative to the brain state indicator on the front surface, the top surface may have brain state indicator lights 26', 28', 30' that are viewable from the top surface. In the embodiment shown in FIG. 18$S_b$, the brain state indicator lights 26', 28', 30' on the top surface may have different colors and/or shapes to correspond with the brain state indicator lights 26, 28, 30. In both embodiments of FIGS. 18$S_a$ and 18$S_b$ the acknowledgement input 20 may be positioned along a top surface of the PAD so that the acknowledgement input 20 is readily accessible to the patient when the brain state indicator 12 is activated.

The top surface of the PAD may comprise one or more additional patient inputs 16, 18. In the illustrated embodiment, the "push to talk" input button 16 is positioned in between two volume toggle buttons 18 and may illuminate when depressed to indicate voice recording. One of the volume toggle buttons 18 may be used to scroll up through the output options, while the other volume toggle button 18 may be used to scroll down through the output options.

The junction between the top and rear surfaces of the PAD may also comprise a door 33 that houses the removable storage device (e.g., a FLASH memory data card) and/or an on/off input button (not shown). When the door 33 is opened, the patient may replace the full (or defective) storage device with a new storage device. Alternatively, if the patient desires to turn on or off the PAD, the patient may activate the on/off input. The patient may keep the PAD on at all times, but in instances which require the PAD to be off (e.g., on an airplane), the patient may have the ability to turn off the PAD and stop the transmission of the data signal from the implanted device—which may help to conserve battery power of the PAD and implanted device.

While the above Figures illustrate separate display devices for displaying the brain state indicators and system state indicators, it may instead be desirable to integrate the indicators into a single output display device, e.g., the LCD. However, even with a single LCD, it may be desirable to separate the LCD into different sections for providing the different information to the patient.

Figure 4A:
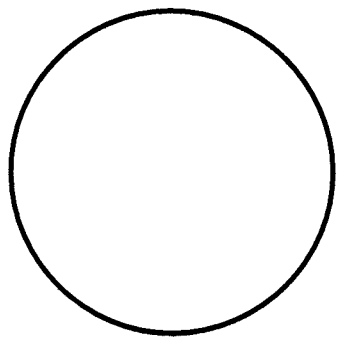
FIGS. 4A-4C show examples of icons that can be used to notify the patient of the patient's brain state.
Figure 4B:
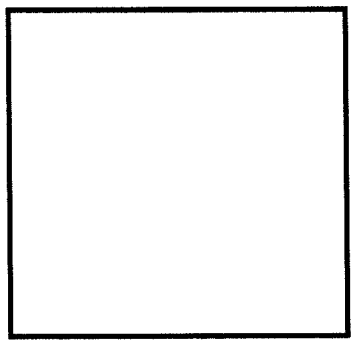
Figure 4C:
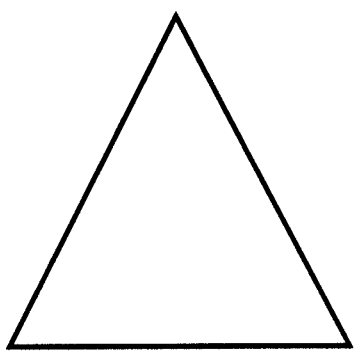

In one configuration, the brain state portion of the LCD output may comprise icons to indicate the patient's brain state. The icons could simply be a text message stating "green light," "yellow light," "red light." In other embodiments, the brain state indication could be a different shape to indicate the patient's brain state (either differently colored or a same color could be used for each of the shapes). FIGS. 4A-4C show some exemplary icons that can be used to notify the patient of brain state. These are exemplary shapes and are not intended to be limiting. Furthermore, instead of icons, it may be desirable to provide text and/or a number that is indicative of the patient's brain state.

Additionally or alternatively to the icons and/or brain state indicators, it may be useful to have the LCD provide a redundant indication to the patient to indicate their brain state. For example, the LCD may be backlit with a color to alert the patient of the brain state. For example, the LCD may have a background color of red, yellow, or green to indicate the brain state in the same manner as do the LED colors described above. The colors may also flash when there is a change in brain state, and/or the red color may flash to indicate that a seizure has been detected.

In addition to the visual indicators, the PAD can emit an audio alert with the speaker 22 (FIG. 1) such as a tone or voice when the brain state changes. For example, when the brain state changes from "low propensity" to "elevated propensity" or from "low propensity" to "unknown," the PAD may emit a beep that is indicative of the change in brain state. The brain states can also be categorized from the most desirable to the least desirable. The "safe" state would be the most desirable state, whereas the "detection" state would be the least desirable. The "unknown" state may be less desirable than "safe or low propensity" but more desirable than "prediction or high propensity." There may be distinctive audio alerts based on whether the brain state has changed from a more desirable brain state to a less desirable brain state, or whether it has changed from a less desirable state to a more desirable state. For example, when the patient's brain state changes from "unknown" or "prediction" to "safe," or from "prediction" to "unknown," the PAD may emit an audible output that indicates a positive change, such as a light chime. In contrast, when the patient's brain state changes from "safe" to "unknown", the PAD may emit a single beep or other audio output to indicate a negative change. When the brain state changes from "unknown" or "safe" to "prediction," the PAD may emit several louder beeps of longer duration or other sound to indicate a more significant negative change. And when the state changes to "detection," the PAD may emit several rapid beeps of short duration. Tactile and visual alerts may be used and can differ in the same manner.

In some social situations it may be desirable for the PAD to alert the patient in a discreet way, such as without the use of sounds and/or lights. In some embodiments the PAD may provide a tactile alert, such as a vibration to indicate a change in brain state. Similar to the changes in audio alerts, each change in brain state can be communicated using the same or different tactile alerts. For example, a change in state to the "elevated propensity," or "detection" states could be the most disruptive to the patient, such as with several long, forceful vibrations, which in a social situation could be assumed to be a cell phone vibration. Audio and visual alerts could be configured to closely resemble the sounds and visual indications of cell phones, PDAs, etc, to allow the PAD alerts to be more discreet.

As described above, in addition to providing a brain state indication, the user interface of the PAD may also provide information to the patient regarding the status of various aspects of the PAD, implanted device, electrodes, and communication link. FIGS. 5A-14F illustrate various examples of icons that may be displayed on the LCD of the PAD.

Figure 5A:
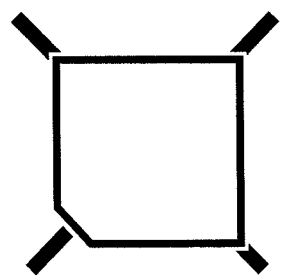
FIGS. 5A-5D illustrate examples of data card icons.
Figure 5B:
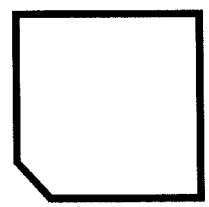
Figure 5C:
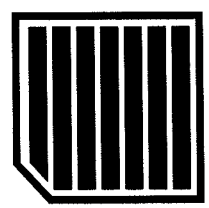
Figure 5D:
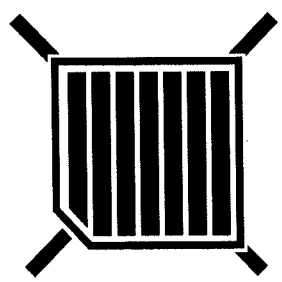

As described above, a storage device, such as a data card, hard drive, etc., may be provided in the PAD and is used to store monitored patient data (for example, EEG signals), inputs from the patient, etc. The PAD preferably monitors whether a storage device is present in the PAD and the remaining storage capacity of the storage device, and notifies the patient of the status. The patient generally knows to remove the storage device when it becomes full and insert a new data card or download the data from the storage device onto another computer or other storage device. In one embodiment a storage device becomes full of data after one week, and is then replaced with another storage device. Exemplary icons used to notify the patient of the storage device status are shown in FIGS. 5A-5D. In the figures, the icon can be divided into seven discrete segments or states (or more). In the illustrated embodiment, one segment corresponds to one day (or other period of time). But in other embodiments, the segment could correspond to a portion of the memory capacity. FIG. 5C indicates that the data card is full, or that seven days worth of data is stored on the card. FIG. 5B indicates that the data card is empty and does not yet contain any data. The four lines (i.e., a general "X" shape) in FIGS. 5A and 5D generally indicate an error with the card. FIG. 5A can indicate there is no storage device present in the PAD and that the patient should insert a storage device. FIG. 5D can indicate that the storage device is not functioning properly and should be reinserted or replaced with a new card. When the storage device is approaching the last day or is on the last day of storage (the icon comprising 7 bars is present), the icon shown in FIG. 5C may also begin to flash to alert the patient of the need to replace the storage device soon. There may also be a periodic audio indication, such as a beep, that the patient should replace the storage device. Coloring or text on the LCD may also be used to indicate the storage device status. In one embodiment a green colored icon indicates that there is a storage device present and indicates either 2 through 7 days of storage remaining. A yellow colored icon may indicate the storage device is on the last day of storage and/or is a reminder to replace the storage device. A red colored icon may indicate a storage device is absent or that there is an error with the storage device. In other embodiments, the storage device icon may include a number—which either indicates the number of days used or the number of days remaining.

As described above, the system state display 14 of the PAD may display icons to indicate the remaining battery power of the PAD 10 and the implanted device. The system state display 14 may have separate icons for the PAD 10 and implanted device (FIGS. 2A, 6A-6H, 7A-7H), or there may be a single icon to indicate the collective battery power for both (FIGS. 8A-8F).

Figure 6A:
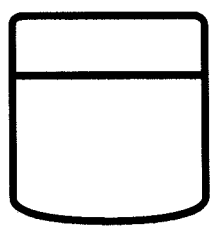
FIGS. 6A-6H show examples of patient advisory device battery strength icons.
Figure 6B:
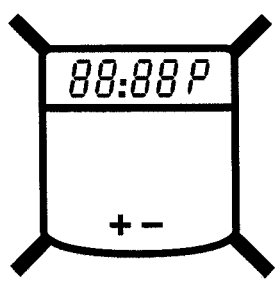
Figure 6C:
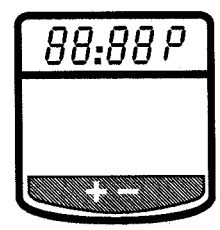
Figure 6D:
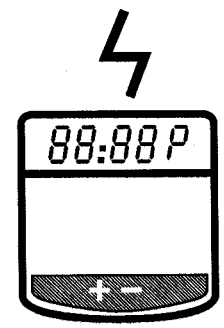
Figure 6E:
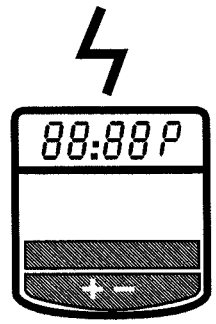
Figure 6F:
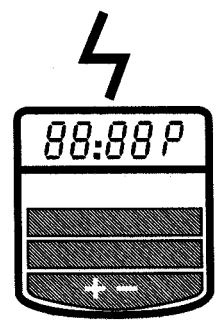
Figure 6G:
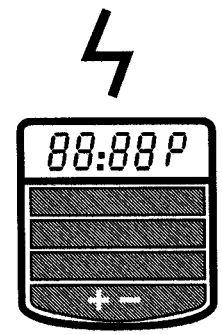
Figure 6H:
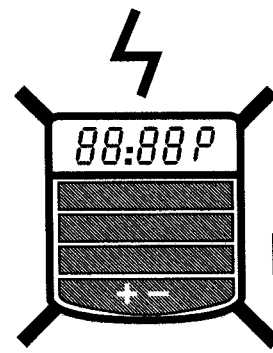

FIGS. 6A-6H illustrate some exemplary PAD battery icons. The more horizontal bars are shown, the more power is remaining. The absence of any bars in FIGS. 6A and 6B indicates the PAD is out of power and needs to be charged. The lightning symbol at the top of the icons is present when the battery is charging (and may flash while charging). The icons in FIGS. 6D-6F show the icon while the PAD battery is being charged. As can be seen, the number of bar increases while being charged, until charging is complete, as shown in FIG. 6G. The "X" through the empty icon as shown in FIG. 6B can indicate the battery power is critically low or a flashing icon (FIG. 6C) may also indicate lower battery power. In other embodiments, the "X" in the icon may be used to indicate there is an error with the PAD 10. In yet other embodiments, the "X" in the icon may be used to indicate that the battery should be replaced. A time indicator may be included in the battery icon, which indicates approximately how long the battery will provide power to the PAD. Audio alerts may also be used to indicate the status of the battery. For example, audio in the form of speech may indicate the battery is charging or that the charging is complete, or there may be a voice reminder to recharge the battery. In some embodiments, the battery status may also be indicated with lights. A green color can show the battery is charging, fully charged, and ⅔ full. A yellow color can indicate the battery is ⅓ full or act as a reminder to recharge the battery. A red color can be used to indicate the battery life is critically low.

The patient may also be alerted to the battery life of the implanted device. The same, similar, or different visual, audio, and/or tactile alerts can be used in the PAD to notify the patient of the implanted device's battery life.

Figure 7A:
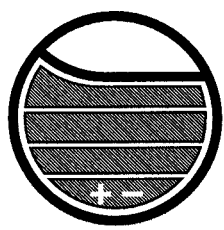
FIGS. 7A-7H show examples of implanted telemetry unit battery strength icons.
Figure 7E:
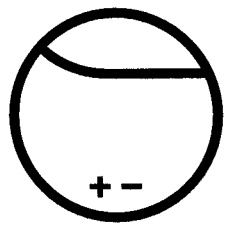
Figure 7B:
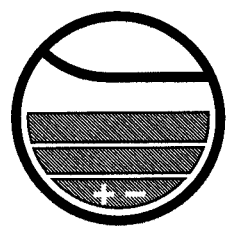
Figure 7F:
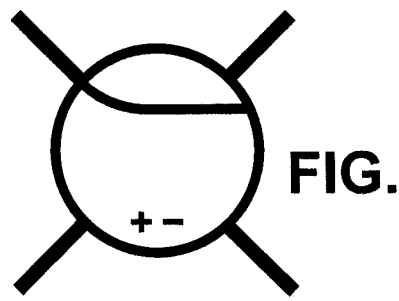
Figure 7C:
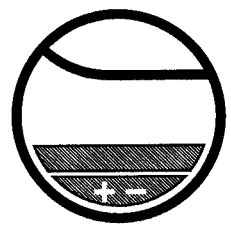
Figure 7G:
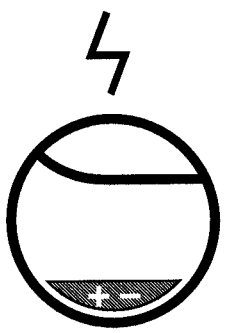
Figure 7D:
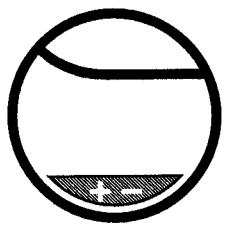
Figure 7H:
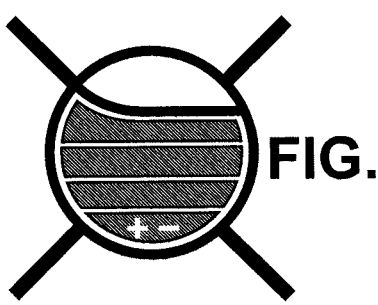

FIGS. 7A-7H show exemplary icons for the implanted device battery. FIGS. 7A-7E illustrate the different charge remaining levels of the battery of the implanted device—and ranges from being fully charged (FIG. 7A) to depleted (FIG. 7E). FIGS. 7F and 7H illustrate errors in the implanted device. FIG. 7G includes the lightning symbol and will be present when the implanted device is being charged.

The icon for the implanted device is preferably different than the icon for the PAD so that the patient can easily recognize which icon represents the device and will know which battery is low. The icons of FIG. 6A-6H have a shape similar to the PAD, while the icons of FIG. 7A-7H have a shape similar to the implanted device. In FIG. 2A, the system state display 14 is graphically divided into an implanted device status section 13 and a PAD status section 15. While the shapes are different than the PAD battery life icon, the bars, lightning symbol, "X", etc., have similar functions.

Figure 8A:
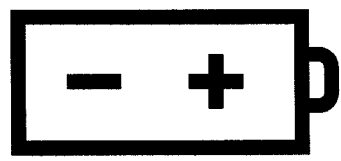
FIGS. 8A-8F show examples of battery life icons.
Figure 8B:
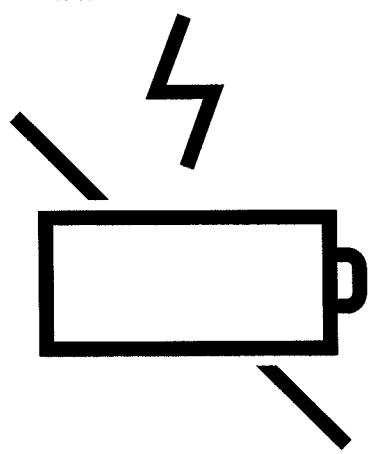
Figure 8C:
Figure 8D:
Figure 8E:
Figure 8F:
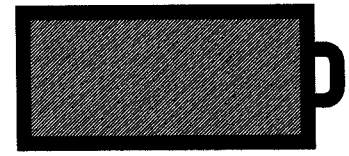

If it is only desired to use a single icon to indicate the battery life of both the power supplies of the implanted device and PAD, a single generic icon could be displayed on the user interface of the PAD. FIGS. 8A-8F show examples of icons that may be used to illustrate the battery life of the implanted device and the PAD. While the PAD and implanted device may have different battery lives, and hence each could have different levels of power remaining, the icon shown in the user interface will likely correspond to the lowest remaining power level of the two power supplies. FIG. 8A illustrates the battery in a charge mode. FIG. 8B illustrates an error associated with the battery. FIGS. 8C-8F illustrate the battery with different levels of charge. While not shown, the battery icon may also be colored to indicate the remaining battery power. A green color can show the battery is charging, fully charged, and ⅔ full. A yellow color can indicate the battery is ⅓ full or act as a reminder to recharge the battery. A red color can be used to indicate the battery life is critically low.

The PAD may also comprise an icon that notifies the patient of the communication signal strength between the implanted device and the PAD. If the signal strength is too weak, the data signals that are indicative of the patient's brain activity may not be received by the PAD, and the patient may not be informed of their estimated brain state. The signal strength icon can be used to inform the patient of the signal strength between the implanted device and the PAD to ensure that the PAD is never, or infrequently, out of telecommunication range with the implanted device. In FIG. 2A, the signal strength indicator 38 comprises a series of semi-circulator bars positioned between the implanted device status section 13 and PAD status section 15. The icons for the signal strength indicator 38 are preferably situated on the LCD such the signal strength indicator 38 is shown originating from the implanted device status section 13 and appears to be traveling to the PAD status section 15.

Figure 9A:
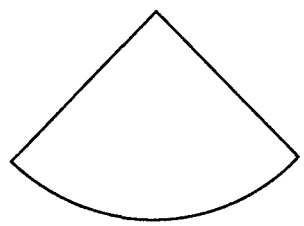
FIGS. 9A-9G show examples of icons showing signal strength between the implanted telemetry unit and the patient advisory device.
Figure 9B:
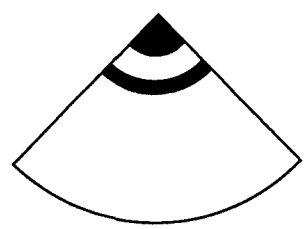
Figure 9C:
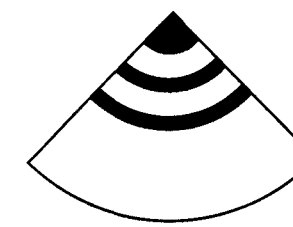
Figure 9D:
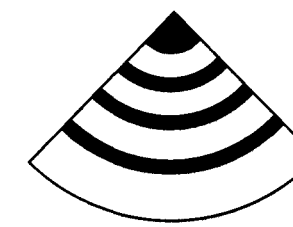
Figure 9E:
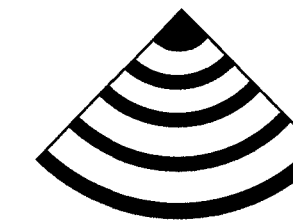
Figure 9F:
Figure 9G:
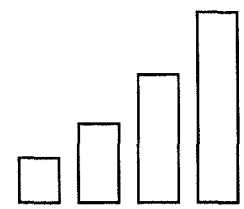

FIGS. 9A-9E show other embodiments of exemplary icons that may be used to indicate signal strength, ranging from zero signal strength in FIG. 9A to full signal strength in FIG. 9E. FIGS. 9F and 9G are alternative icons to indicate signal strength. As in FIG. 2A, the number of bars is related to the signal strength. Other visual indicators such as color may be used. A green color may be used to indicate medium signal strength through high signal strength. A yellow color may be used to indicate low signal strength. A red color may be used to indicate the signal has been lost.

Audio alerts may also be used to indicate a lost signal. For example, audio tones may be used to indicate a decrease in signal strength, or a voice alert may be used to indicate the signal has been lost, etc. Advantageously, such audio alerts may also act to remind the patient of the position of where the PAD is located. For example, many patients may set their PAD on their desk or in their purse. If they happen to walk out of the communication range of the implanted device/PAD, the audio alert will remind them to bring their PAD with them. Furthermore, the audio alert may also be helpful for patients when they misplace their PAD. The audio alert may be configured to continue to sound for a specific period of time (e.g., 10 seconds) even after the patient has returned into communication range with the PAD. Additional description of the distance alarm can be found in commonly owned U.S. patent application Ser. No. 12/020,507, filed Jan. 25, 2008, published as U.S. Patent Publication No. 2008/0183097, abandoned, the disclosure of which is incorporated by reference herein in its entirety.

Figure 10A:
FIGS. 10A-10D show icons indicating the patient advisory device's alert audio level.
Figure 10B:
Figure 10C:
Figure 10D:

The user interface may also provide an indication of the alert mode. In FIG. 2A, an alert mode indicator 42 is provided. FIGS. 10A-10D and 11A-11G illustrate exemplary icons which indicate the level of audio alerts for the PAD. FIG. 10A illustrates an icon that indicates that the audio alerts are muted. FIG. 10B is an icon that shows that the audio alerts are muted and alerts are provided with a vibratory output. FIG. 10C is an icon that shows that the audio alerts are in a medium audio range and FIG. 10D is an icon that shows that the audio alerts are in a higher audio range.

Figure 11A:
FIGS. 11A-11G show icons indicating the patient advisory device's sound level.
Figure 11B:
Figure 11C:
Figure 11D:
Figure 11E:
Figure 11F:
Figure 11G:

FIGS. 11A-11G illustrate additional alert mode icons. The icon of FIG. 11A illustrates that the audio alerts are muted. The icon of FIG. 11B indicates the PAD is muted but set to a vibration mode. The icons of FIGS. 11C and 11G indicate that there is both an audio alert and a vibratory alert. FIGS. 11D-11F illustrate the various volume levels for the audio alerts.

Figure 12A:
FIGS. 12A-12D show icons indicating the recording sound level.
Figure 13A:
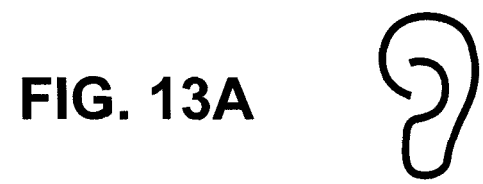
FIGS. 13A-13D show icons notifying the patient of the message sound level.
Figure 12B:
Figure 13B:
Figure 12C:
Figure 13C:
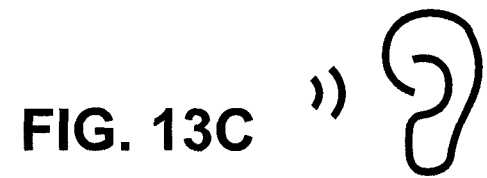
Figure 12D:
Figure 13D:
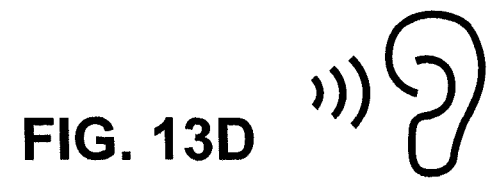

FIGS. 12A-12D show examples of an icon that may be used to indicate that the voice recording function has been activated. The icon may only be illuminated when the patient has depressed (and held down) the voice recording input. FIG. 12A shows the voice recording icon with the lowest level, up to the highest recording level in FIG. 12D. In other embodiments, it may be desirable to provide a ring around the voice recording input that illuminates when depressed by the patient. In the embodiment shown in FIG. 2A, these icons are omitted and a single recording notice light 31 is used.

Some embodiments of the PAD may provide voice instructions (e.g., "take a medication") or voice alerts (e.g., seizure predicted). For such embodiments, the patient may have the ability to adjust the volume of the voice alerts separately from the volume of the tone alerts. FIGS. 13A-13D shows the various icons that would be displayed to indicate the volume level of the voice alerts.

The icons illustrated in FIGS. 4-13 may be arranged in any desired configuration on the LCD or other output on the PAD. FIGS. 14A-14F show some other examples of configurations of the icons that may be used to notify the patient of the status of the system components.

Figure 14A:
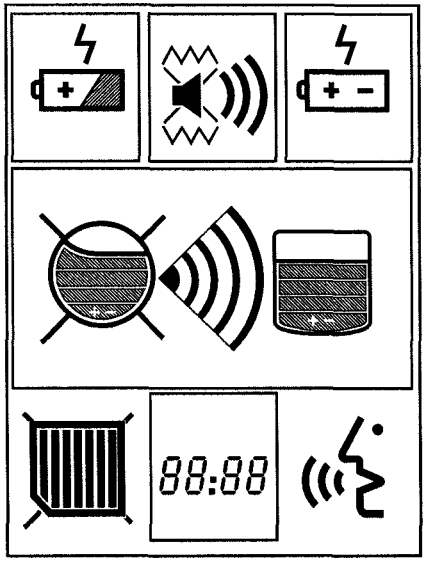
FIGS. 14A-14G illustrate examples of LCD displays that can be used to alert the patient of the state of the system's components.

FIG. 14A illustrates a display that comprises many of the aforementioned icons. A central portion illustrates the signal strength between the implanted device icon and the PAD icon. Remaining battery life for the PAD and implanted device are above each of the respective icons. Alert mode is positioned in an upper portion between the remaining battery life icons. A bottom portion of the display includes a clock icon—which may either provide a time of day indication, expected time to seizure, or expected safe period. The data card status icon and the voice recording icon are also in the bottom portion of the display.

Figure 14B:
Figure 14C:
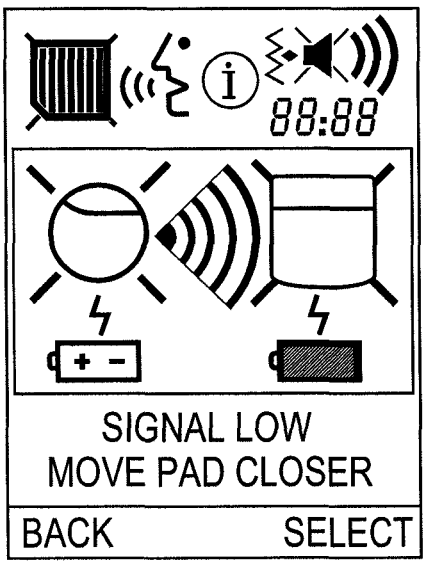

FIGS. 14B and 14C illustrate displays that include a text box for providing text output to the patient along with the icons. FIG. 14B illustrates various text outputs that may be provided to the patient. The outputs may include alerts (e.g., check data card, see user manual, etc.) and/or an acknowledgment that the patient has adjusted some aspect of the system (e.g., notification tone OFF, etc.). Also shown in FIGS. 14B and 14C is an information icon (i) that is meant to inform the patient that their attention is needed. The information icon (i) may flash and an audio beep may be emitted. The text that is associated with the information icon (i) alert may be displayed in the text box. The displays in FIGS. 14B and 14C may be displayed on a touch screen, in which the user can use a stylus or soft keys to navigate through screen options (as shown by the "Back" and "Select" icons).

Figure 14D:
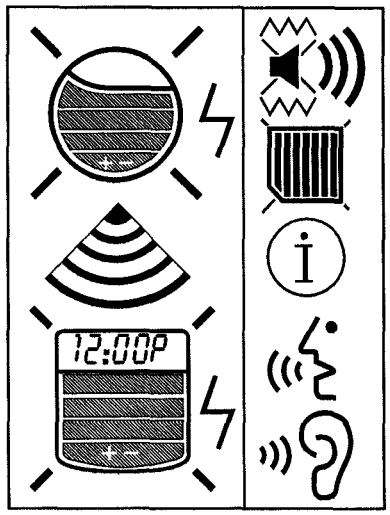
Figure 14E:
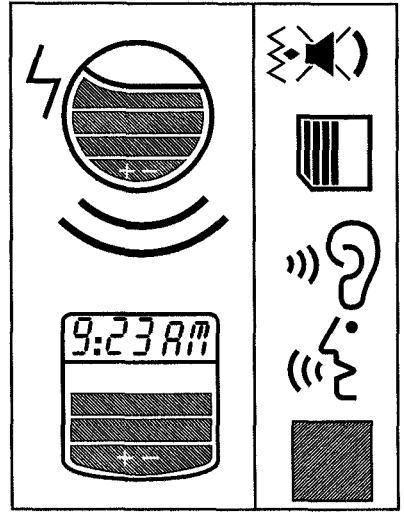

FIGS. 14D and 14E illustrate an alternative display in which the implanted device and PAD are in a vertical configuration along a left portion of the display and the other icons are displayed in a vertical configuration on a right portion of the display.

Figure 14F:
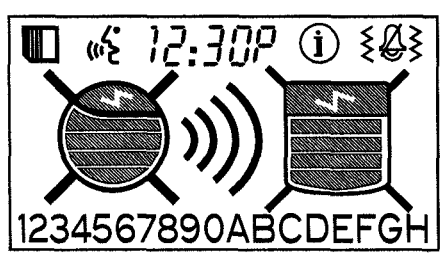
Figure 14G:
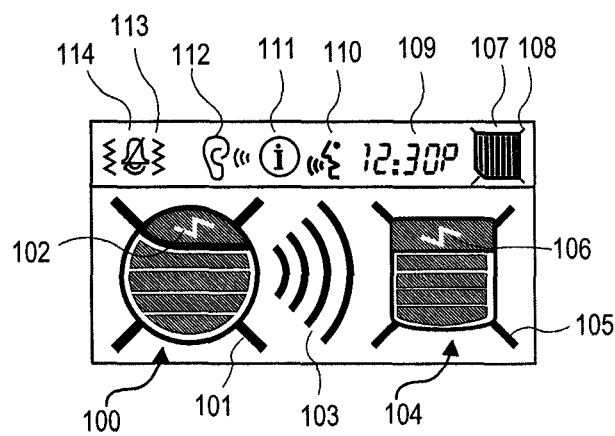

FIGS. 14F and 14G shows an implanted device icon 100 showing battery power, with implanted device error indicator 101, implanted device charge indicator 102. Also shown is signal strength 103 from implanted device to PAD. The PAD icon 104 shows battery power, PAD error indicator 105 and PAD charging indicator 106. Data storage icon 107 indicates how much space remains on the data storage device, and error indicator 108 notifies of a data storage device error. The display may include a clock 109 that shows the time. Recording icon 110 indicates the PAD is recording audio input from the patient. Information icon 111 instructs the user to refer to the user's manual. Audible instruction icon 112 indicates that the PAD is providing audible instructions, and indicates the volume of the instructions. Tactile icon 113 notifies the patient the vibratory mechanism is turned on and the PAD will vibrate based on the patient settings. Sound icon 114 shows the sound has been muted on the PAD.

As can be seen from the above, the PAD may take any number of configurations, and the layout, number, and types of indicators and inputs present on the PAD can vary. However, as patients with epilepsy may prefer to discretely use a device to monitor their brain state, it may be desirable to have the housing of the PAD 10 have a size and shape that is similar to a cellular phone, pager, MP3 player, personal digital assistant (PDA), or other commonly used consumer electronics device. To such end, if desired, the components of the PAD may be integrated into a cellular phone, PDA, or other portable computing device. For example, much of the hardware illustrated in FIG. 1 is already part of a standard cellular phone and/or PDA, and the primary addition to the hardware of the cellular phone/PDA would be the addition of the antenna and telemetry circuit, the DSP 54 (with algorithms) and the brain state indicators. The brain state indicators could be icons on the display of the phone or any of the physical light indicators as described above. Thus, for a standard cellular phone (e.g., a flip-phone), the keys and other inputs of the cellular phone could be used to provide any of the inputs described above, the LCD of the phone could be used to indicate the system status, and the brain state indicators could be positioned on any exposed surface of the phone (or one or more of the LCDs, if desired).

Figure 15:
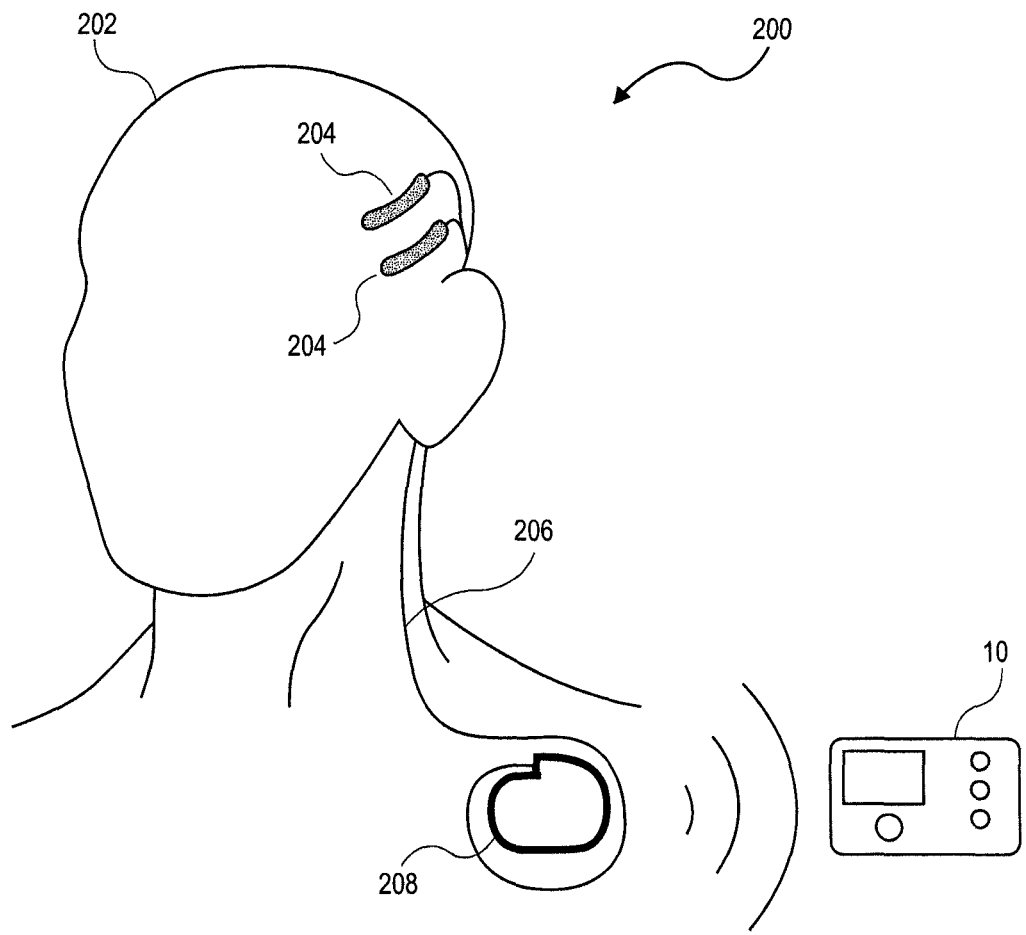
FIG. 15 illustrates an example of a system that includes the PAD.

FIG. 15 illustrates a simplified system that may include any of the above described PADs 10. The system 200 illustrated in FIG. 15 may be used to monitor a brain state of subject 202 for purposes of estimating a subject's propensity for transitioning into an ictal state. The system 200 of the illustrated embodiment provides for substantially continuous sampling and analysis of brain wave electrical signals.

The system 200 comprises one or more electrodes 204 configured to measure signals from the subject 202. The electrodes 204 may be located anywhere in or on the subject. In the exemplary embodiment, the electrodes 204 are configured in one or more arrays and are positioned to sample electrical activity from the subject's brain. The electrodes 204 may be attached to the surface of the subject's body (e.g., scalp electrodes), attached to the skull (e.g., subcutaneous electrodes, bone screw electrodes, sphenoidal electrodes, and the like), or, may be implanted intracranially in the subject 202. The electrode arrays include one or more macroelectrodes that are configured to monitor groups of neurons, or one or more microelectrodes that are configured to monitor a single neuron. In one embodiment, one or more of the electrodes 204 will be implanted adjacent a previously identified epileptic focus, a portion of the brain where such a focus is believed to be located, or adjacent a portion of a seizure network.

Any number of electrodes 204 may be employed, but the electrodes 204 will preferably include between 1 electrode and 16 electrodes. The electrodes may take a variety of forms. In one embodiment, the electrodes comprise grid electrodes, strip electrodes and/or depth electrodes which may be permanently implanted through burr holes in the head. In addition to measuring brain activity, other sensors (not shown) may be employed to measure other physiological signals from the subject 202.

In an embodiment, the electrodes 204 will be configured to substantially continuously sample the brain activity in the immediate vicinity of the electrodes 204. The sensors could be one or more microelectrodes that are configured to sense the activity of a single neuron, or the electrodes could be macroelectrodes that are configured to sense activity of a group of neurons in the subject's brain. The electrodes 204 are electrically joined via cables 206 to the implanted device 208, but could be wirelessly coupled to the implanted device 208 or other external device. In one embodiment, the cables 206 and implanted device 208 will be implanted in the subject 202. For example, the implanted device 208 may be implanted in a sub-clavicular cavity or abdominal cavity of the subject 202. In alternative embodiments, the cables 206 and implanted device 208 may be implanted in other portions of the subject's body (e.g., in the head) or attached to the subject 202 externally.

The implanted device 208 is configured to facilitate the sampling of low frequency and high frequency signals from the electrodes 204. Sampling of brain activity may be carried out at a rate above about 200 Hz, and preferably between about 200 Hz and about 1000 Hz, and most preferably at or above about 400 Hz. The sampling rates could be higher or lower, depending on the specific features being monitored, the subject 202, and other factors. Each sample of the subject's brain activity may be encoded using between about 8 bits per sample and about 32 bits per sample, and preferably about 16 bits per sample. In alternative embodiments, the implanted device 208 may be configured to measure the signals on a non-continuous basis. In such embodiments, signals may be measured periodically or aperiodically.

PAD 10 receives and stores patient data, including measured EEG signals and possibly other physiological signals, from the implanted device 208. PAD 10 could also receive and store extracted features, classifier outputs, subject inputs, and the like. Communication between the PAD 10 and the implanted device 208 may be carried out through wireless communication, such as a radiofrequency link, infrared link, optical link, ultrasonic link, or other conventional or proprietary wireless link. The wireless communication link between the PAD 10 and the implanted device 208 may provide a one-way or two-way communication link for transmitting data. In alternative embodiments, it may be desirable to have a direct communications link from the PAD 10 to the implanted device 208, such as, for example, via an interface device positioned below the subject's skin. The interface (not shown) may take the form of a magnetically attached transducer that would enable power to be continuously delivered to the implanted device 208 and would provide for relatively higher rates of data transmission. Error detection and correction methods may be used to help insure the integrity of transmitted data. If desired, the wireless data signals can be encrypted prior to transmission to the PAD 10.

In use, the electrode arrays are used to sample brain activity (e.g., EEG signals) from the patient's brain. The sampled brain activity is transmitted from the electrode arrays 204 through the cable leads 206 to the implanted device 208 (FIG. 15). The implanted device 208 processes (e.g., filters, amplifies, digitizes, compresses, extracts features, and/or encrypts) the sampled brain activity signals and then wirelessly transmits a data signal with patient data to the PAD. As shown in FIG. 1, the antenna and telemetry circuit 58 in the PAD 10 receive the wireless signal from the implanted device with the patient data and transmits the patient data to the main processor 52 and/or DSP 54. The patient data may be stored in the external storage device 62 for subsequent download to a physician computer (not shown). The DSP 54 may process the patient data in substantially real time with one or more brain state algorithms to estimate the patient's brain state.

Figure 16:
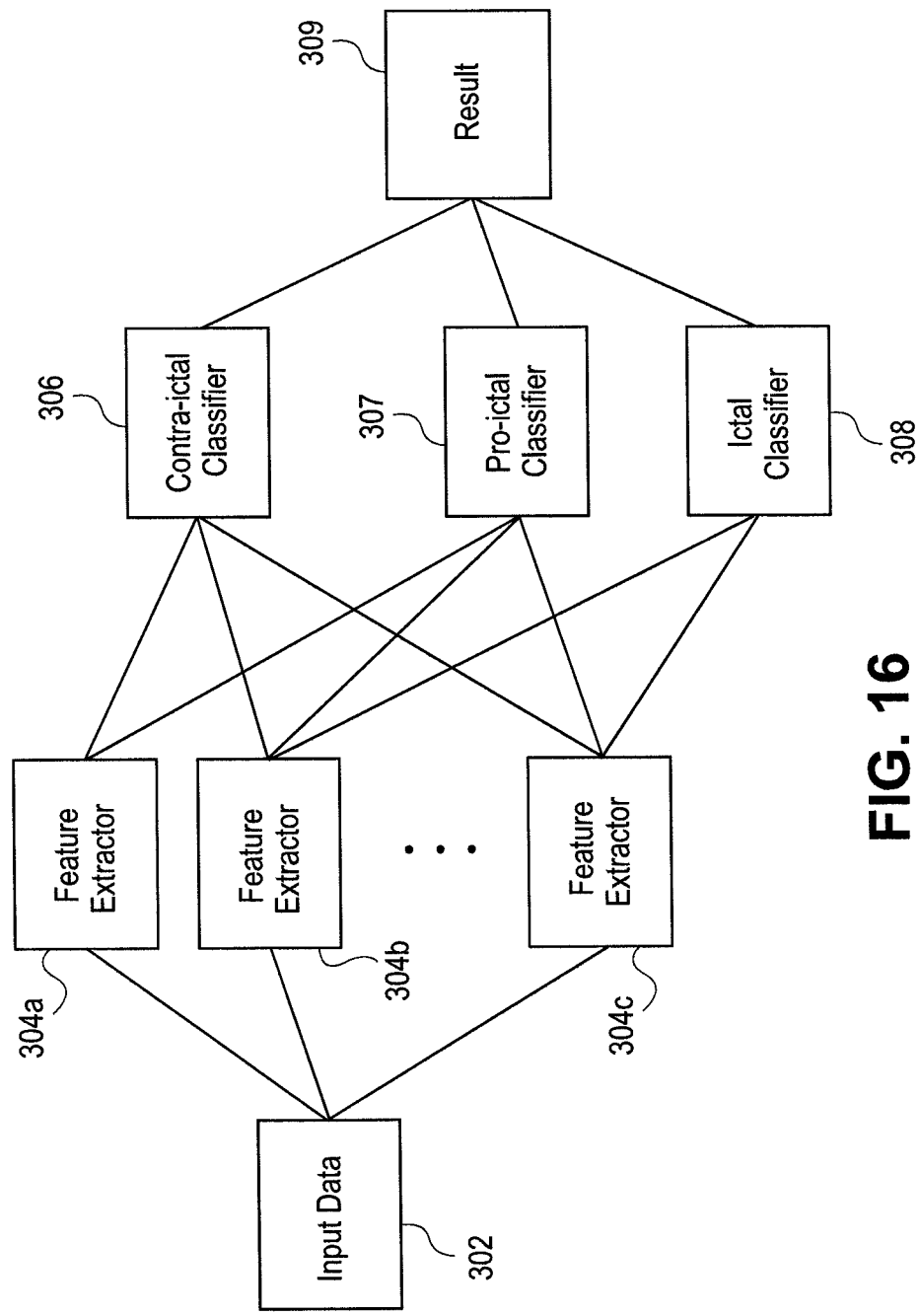
FIG. 16 illustrates a plurality of algorithms that may be useful with the system of FIG. 15.

In preferred embodiments, a plurality of brain state algorithms (e.g., safety algorithm, prediction algorithm, and detection algorithm) are optimized for different purposes. While each of the algorithms will be optimized for different purposes, the algorithms may use one or more of the same features. For example, as shown in FIG. 16, the DSP 54 may comprise a plurality of brain state algorithms which include one or more feature extractors and classifiers. The feature extractors 304*a*, 304*b*, 304*c* are each configured to extract the relevant features from the EEG signals (shown generically in FIG. 16 as "input data 302"). The different brain state algorithms may take the features and use an optimized classifier 306, 307, 308 and attempt to classify the feature vector. For example, the contra-ictal classifier 306 will attempt to determine if the patient is in a brain state in which the patient is highly unlikely to transition into an ictal state within a predetermined time period. The pro-ictal classifier 307 will attempt to determine if the patient is in a pro-ictal brain state in which the patient has an elevated propensity for transitioning into the ictal state. The ictal classifier 308 will attempt to determine if the patient has already transitioned into the ictal state. While the above examples describe three separate algorithms to analyze the patient's brain state, it should be appreciated that a single algorithm may be used to perform the same function of the aforementioned algorithms.

The outputs of the three different algorithms may be combined in a logical manner to determine the type of output communication that is provided to the patient. FIG. 17 illustrates one example of how the output from the three different brain state algorithms may be used to generate the communication output. In the illustrated embodiment, the output from the algorithms is illustrated as either "0" or "1". A "1" for the safety algorithm would mean that the safety algorithm determined that the patient was "safe" and unlikely to transition into the ictal state within a predetermined time period, whereas a "0" for the safety algorithm means that the patient is not "safe"—but that does not necessarily mean that the patient has an increased propensity for transitioning into the ictal state. A "1" for the prediction algorithm would mean that the prediction algorithm determined that the patient has an elevated propensity for transitioning into the ictal state (e.g., is in a pro-ictal state), whereas a "0" for the prediction algorithm means that the patient does not have an increased propensity for transitioning into the ictal state. A "1" for the detection algorithm would mean that the detection algorithm determined that the patient was in the ictal state, whereas a "0" for the detection algorithm means that the patient is determined to not be in the ictal state.

In the illustrated example of FIG. 17, the possible brain state indicator outputs include a green light (safe brain state), a yellow light (unknown brain state), a solid red light (pro-ictal brain state), and a flashing red light (ictal brain state). Of course, any type of output could be provided to indicate the patient's brain state, and the present invention is not limited to such an output. For example, as described above, the green light may be replaced with a blue light, and the yellow light may be replaced with a white light. Other configurations are possible.

In the upper left corner of the chart in FIG. 17 is the combination of the outputs from the three algorithms in which the output of all three of the algorithms are "0". In such case, none of the algorithms are able to provide a positive determination and the patient's brain state would fall in the unknown state. Hence, the output to the patient would be the yellow light.

In the bottom left square of the left-most column, where the safety algorithm determines that the patient is safe (safety algorithm output is "1") and neither the prediction algorithm nor the detection algorithm determine that the patient is in a pro-ictal brain state or an ictal brain state (e.g., both are "0"), the patient is deemed to be in a safe brain state and the output to the patient is the green light.

In the middle four boxes—in which the seizure detection algorithm output is a "1", all of the output combinations are determined to be seizure detection and a red flashing light would be provided to the patient. In this configuration, the seizure detection algorithm would take precedent over the seemingly inconsistent results from the safety algorithm and the prediction algorithm. Of course, in other configurations, where the results from the different algorithms are inconsistent, it may be desirable to estimate the patient to be in an "unknown" brain state and provide a yellow light (or similar output).

The right column of the chart shows the situation where the seizure prediction algorithm has determined that the patient is in a pro-ictal brain state and the detection algorithm has determined that the patient is not yet in the ictal brain state. In such situations, the output from the prediction algorithm would take precedent over the output from the safety algorithm and the output to the patient would be that of "seizure predicted" and a red flashing light would be provided. Of course, in other configurations, in the situation where the safety algorithm is inconsistent with the prediction algorithm (e.g., both are "1"), it may be desirable to estimate the patient to be in an "unknown" brain state and provide a yellow light (or similar output).

Thus, depending on the outputs from the brain state algorithms, the appropriate brain state indicator is lit and an audible or tactile alert is provided to the patient when the patient's brain state changes. The alerts can be programmed to occur and stop after a certain amount of time, or to continue until there is some user intervention, such as an acknowledgement that the user is aware of the alert. The user intervention can be accomplished by any of the user input techniques described herein, such as pressing the talk button 16 or acknowledgement button 20 on the PAD. The PAD may also include an "alert" or "information" indicator (such as an LED, or tone) that alerts the patient that a change in brain state or system component state has occurred, or that user intervention is required. This alert indicator may occur in conjunction with another alert, and may simply be used as a universal indicator to the patient that the user needs to pay attention to the PAD and/or intervene.

The brain state indicators on the PAD 10 allow the patient to substantially continuously monitor the brain state on a real-time basis. Such brain state indicators may be used by the patient to assess which activities "triggers" their brain to move them from a "safe" state to an "unknown" or "pro-ictal state." Consequently, over time the patient may be able to avoid the particular triggers.

In some embodiments, the communication assembly in the implanted device may include a therapy assembly that is adapted to automatically initiate therapy to the patient when the patient has an elevated propensity to a seizure.

One treatment for epilepsy that has demonstrated some utility is open loop Vagus Nerve Stimulation (VNS). This is a reversible procedure which introduces an electronic device which employs a pulse generator and an electrode to alter neural activity. The vagus nerve is a major nerve pathway that emanates from the brainstem and passes through the neck to control visceral function in the thorax and abdomen. VNS uses open looped, intermittent stimulation of the left vagus nerve in the neck in an attempt to reduce the frequency and intensity of seizures. See Fisher et al., "Reassessment: Vagus nerve stimulation for epilepsy, A report of the Therapeutics and Technology Assessment Subcommittee of the American Academy of Neurology," Neurology 1999; 53:666-669. While not highly effective, it has been estimated that VNS reduces seizures by an average of approximately 30-50% in about 30-50% of subjects who are implanted with the device.

Another recent alternative electrical stimulation therapy for the treatment of epilepsy is deep brain stimulation (DBS). Open-loop deep brain stimulation has been attempted at several anatomical target sites, including the anterior nucleus of the thalamus, the centromedian nucleus of the thalamus, and the hippocampus.

Another type of electrical stimulation therapy for the treatment of epilepsy has been proposed by NeuroPace, Inc., in which an implanted device is designed to detect abnormal electrical activity in the brain and respond by delivering electrical stimulation to the brain.

There have also been a number of proposals described in the patent literature regarding the use of predictive algorithms that purportedly can predict the onset of a seizure. When the predictive algorithm predicts the onset of a seizure, some type of warning is provided to the subject regarding the oncoming seizure or some sort of therapy is initiated. For example, see U.S. Pat. No. 3,863,625 to Viglione, U.S. Pat. No. 5,995,868 to Dorfmeister/Osorio, and U.S. Pat. No. 6,658,287 to Litt et al., the complete disclosures of which are incorporated herein by reference, which describe a variety of proposed seizure prediction systems. However, to date, none of the proposed seizure prediction systems have shown statistically significant results. While most seizures are short-lasting events that last only a few minutes, the seemingly random nature of the occurrence of seizures is what overshadows and destroys a subject's quality of life.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A system for monitoring a patient's brain activity, the system comprising:
   an electrode for detecting physiological signals from the patient;
   a communication assembly coupled to the electrode, the communication assembly configured to wirelessly transmit a data signal that is encoded with data that is indicative of the detected physiological signals; and
   an external patient advisory device configured to receive the data signal from the communication assembly, the patient advisory device comprising:
   a processing assembly comprising one or more brain state algorithms that process the data signal to estimate the patient's brain state;
   a brain state indicator configured to provide the estimated brain state, wherein the brain state indicator indicates:
   when the estimated brain state is a contra-ictal brain state comprising a protected state in which the patient has a risk of transitioning from a non-ictal state to an ictal state within an upcoming time period below a first risk level; and
   when the estimated brain state is a pro-ictal brain state comprising a prediction state in which the patient has a risk of transitioning from a non-ictal state to an ictal state within an upcoming time period above a second risk level, wherein the second risk level is higher than the first risk level; and
   an output assembly comprising a first indicator that provides an indication of a status of the patient advisory device, a second indicator that provides an indication of a status of the communication assembly, and a failure alert indicator that provides an indication that a failure has occurred with the patient advisory device or the communication assembly.

2. The system of claim 1 wherein the output assembly further comprises a third indicator that provides an indication when there is a problem with transmission of the data signal from the communication assembly or receipt of the data signal at the patient advisory device.

3. The system of claim 1 wherein the communication assembly is programmed to substantially continuously transmit the data signal to the patient advisory device.

4. The system of claim 1 wherein the patient advisory device comprises a memory assembly for storing the data signal.

5. The system of claim 1 wherein the brain state indicator comprises a plurality of brain state indicators that differentiate between the contra-ictal state, a pro-ictal state, and an ictal state.

6. The system of claim 1, the system further comprising:
   a therapy delivery device, wherein the therapy delivery device is adapted to automatically initiate therapy to the patient when the patient has an elevated propensity of seizure.

7. The system of claim 1 wherein the output assembly further comprises a communication indicator that provides an indication that the patient advisory device is out of communication range with the communication assembly.

8. The system of claim 1 wherein the output assembly further comprises a data indicator that provides an indication that data is not being received by the patient advisory device.

9. The system of claim 1 wherein the communication assembly further comprises a processor programmed to encrypt the detected physiological signals from the patient.

10. The system of claim 1 wherein the communication assembly further comprises a processor programmed to compress the detected physiological signals from the patient.

11. The system of claim 1, the system further comprising:
    an electrical stimulator adapted to automatically initiate stimulation therapy to the patient when the patient has an elevated propensity of seizure.

12. A patient advisory device comprising:
    a housing; and
    a user interface on the housing comprising:
    a first portion providing system status information including a failure alert indicator that provides an indication that a failure has occurred with the patient advisory device; and
    a second portion comprising a brain state indicator that provides a substantially continuous indication of a patient's propensity for a seizure, wherein the brain state indicator indicates:
    when an estimated brain state is a contra-ictal brain state comprising a protected state in which the patient has a risk of transitioning from a non-ictal state to an ictal state within an upcoming time period below a first risk level; and
    when the estimated brain state is a pro-ictal brain state comprising a prediction state in which the patient has a risk of transitioning from a non-ictal state to an ictal state within an upcoming time period above a second risk level, wherein the second risk level is higher than the first risk level.

13. The device of claim 12 wherein the brain state indicator comprises a plurality of brain state indicators that differentiate between the contra-ictal state, a pro-ictal state, and an ictal state.

14. A patient advisory device comprising:
a communication assembly configured to wirelessly receive a substantially continuously transmitted data signal that is encoded with brain activity data from a detection device disposed to detect a physiological signal from a patient;
a digital signal processor that executes a plurality of brain activity algorithms on the substantially continuously transmitted data signal to estimate the patient's brain state;
a brain state indicator that is activated to report the estimated brain state estimated by at least one of the plurality of brain activity algorithms, wherein the brain state indicator indicates:
when the estimated brain state is a contra-ictal brain state comprising a protected state in which the patient has a low risk of transitioning from a non-ictal state to an ictal state within an upcoming time period is below a first risk level; and
when the estimated brain state is a pro-ictal brain state comprising a prediction state in which the patient has a risk of transitioning from a non-ictal state to an ictal state within an upcoming time period above a second risk level, wherein the second risk level is higher than the first risk level;
a first status indicator that indicates an operational status of the patient advisory device;
a second status indicator that indicates an operational status of the detection device; and
a failure alert indicator that provides an indication that a failure has occurred with the patient advisory device or the detection device.

15. The patient advisory device of claim 14 further comprising:
a communication indicator configured to issue an alert when the patient advisory device is out of communication range from the detection device.

16. The patient advisory device of claim 14 wherein the plurality of brain activity algorithms comprise a seizure detection algorithm, a seizure prediction algorithm, and a safety algorithm.

17. The patient advisory device of claim 14 further comprising: a system state indicator that indicates a signal strength of the substantially continuously transmitted data signal that is encoded with the brain activity data from the detection device.

18. The patient advisory device of claim 14 wherein the brain state indicator comprises a plurality of brain state indicators that differentiate between the contra-ictal state, a pro-ictal state, and an ictal.

19. The patient advisory device of claim 16 wherein the safety algorithm is configured to report the estimated brain state to be a contra-ictal state, wherein the contra-ictal state comprises a protected state in which the patient has a low risk of transitioning from a non-ictal state to an ictal state within an upcoming time period.

* * * * *